United States Patent
Murphy et al.

(10) Patent No.: US 6,808,873 B2
(45) Date of Patent: Oct. 26, 2004

(54) SCREENING ASSAYS USING INTRAMITOCHONDRIAL CALCIUM

(75) Inventors: Anne N. Murphy, Encinitas, CA (US); Amy K. Stout, Atlanta, GA (US)

(73) Assignee: MitoKor, Inc., San Diego, CA (US)

( * ) Notice: Subject to any disclaimer, the term of this patent is extended or adjusted under 35 U.S.C. 154(b) by 0 days.

(21) Appl. No.: 09/765,104

(22) Filed: Jan. 16, 2001

(65) Prior Publication Data

US 2001/0046664 A1 Nov. 29, 2001

Related U.S. Application Data

(60) Provisional application No. 60/176,384, filed on Jan. 14, 2000.

(51) Int. Cl.[7] .............................. C12Q 1/00; C12Q 1/68; C07H 21/07; C07H 21/04; A01N 61/00
(52) U.S. Cl. ................................ 435/4; 435/6; 435/7.1; 435/91.1; 435/91.7; 536/22.1; 536/23.1; 536/24.3; 536/24.31; 536/24.32; 536/24.53; 514/1
(58) Field of Search ............................ 435/6, 7.1, 91.1, 435/91.2; 536/22.1, 23.1, 24.3–33

(56) References Cited

U.S. PATENT DOCUMENTS

| | | | |
|---|---|---|---|
| 5,049,673 A | 9/1991 | Tsien et al. | 546/107 |
| 5,459,251 A | 10/1995 | Tsujimoto et al. | 536/23.5 |
| 5,501,980 A | 3/1996 | Katerinopoulos et al. | 436/74 |
| 5,888,498 A | 3/1999 | Davis et al. | 424/93.21 |
| 6,183,948 B1 * | 2/2001 | Marban et al. | |

OTHER PUBLICATIONS

Litsky et al Biochemistry vol. 26 pp. 7071–7080 1997.
Griffin and Segall, "Effects of the Pyrrolizidine Alkaloid Senecionine and the Alkenals trans–4–OH–Hexenal and trans–2–Hexenal on Intracellular Calcium Compartmentation in Isolated Hepatocytes," *Biochemical Pharmacology* 38(3):391–397, 1989.
Heng et al., "Ethambutol is Toxic to Retinal Ganglion Cells via an Excitotoxic Pathway," *Investigative Ophthalmology & Visual Science* 40(1):190–196, Jan. 1999.
Selak and Smith, "Platelet–activating Factor–induced Calicum Mobilization in Human Platelets and Neutrophils: Effects of PAF–acether Antagonists," *J. Lipid Mediators* 1(2):125–137, 1989.
Aizu et al., "Anthralin, A Non–TPA Type Tumor Promoter, Synergistically Enhances Phorbol Ester–Caused Prostaglandin $E_2$ Release From Primary Cultured Mouse Epidermal Cells," *Japan. J. Pharmacol.* 60(1):9–17, Sep. 1992.
Antoniu et al., "Inhibition of $Ca^{2+}$ Release From The Isolated Sacroplasmic Reticulum. I. $Ca^{2+}$ Channel Blockers," *Biochem. Biophys. Acta* 816(1):9–17, Jun. 11, 1985.

(List continued on next page.)

*Primary Examiner*—Jeffrey Siew
(74) *Attorney, Agent, or Firm*—Seed Intellectual Property Law Group PLLC

(57) ABSTRACT

The invention provides methods for screening for agents that modulate mitochondrial function and in particular mitochondrial regulation of intracellular calcium. The methods may be used to detect agents that bind to a mitochondrial calcium uniporter and may also detect inhibitors or uncouplers of mitochondrial respiration. Agents identified using the screens provided herein have application in the prevention and treatment of a variety of diseases associated with abnormal mitochondrial function.

71 Claims, 11 Drawing Sheets

OTHER PUBLICATIONS

Ashkenazi et al., "Death Receptors: Signaling and Modulation," *Science* 281(5381):1305–1308, Aug. 28, 1998.

Badaoui et al., "Effects of Cyclopiazonic Acid on Membrane Currents, Contraction and Intracellular Calcium Transients in Frog Heart," *J. Mol. Cell. Cardiol.* 27(11):2495–2505, Nov. 1995.

Begum et al., "Stimulation of Protein Phosphatase–1 Activity by Insulin in Rat Adipocytes. Evaluation of the role of mitogen–activated protein kinase pathway," *J. Biol. Chem.* 270(2):709–714, Jan. 13, 1995.

Bernardi et al., "Modulation of the Mitochondrial Cyclosporin A–Sensitive Permeability Transition Pore. I. Evidence of two separate $Me^{2+}$ binding sites with opposing effects on the pore open probability," *J. Biol. Chem.* 268(2):1006–1010, Jan. 15, 1993.

Bernardi et al., "Modulation of the Mitochondrial Permeability Transitioin Pore. Effect of Protons and Divalent Cations," *J. Biol Chem* 267(5):2934–2939, Feb. 15, 1992.

Berridge et al., "Cytosolic calcium oscillators," *FASEB J.* 2(15):3074–3082, Dec. 1988.

Beutner et al., "Complexes Between Porin, Hexokinase, Mitochondrial Creatine Kinase and Adenylate Translocator Display Properties of the Pemerability Transition Pore, Implication for Regulation of Permeability Transition by the Kinases," *Biochim. Biophys. Acta* 1368:7–18, 1998.

Brini et al., "A Calcium Signaling Defect in the Pathogenesis of a Mitochondrial DNA Inherited Oxidative Phosphorylation Deficiency," *Nature Medicine* 5(8):951–954, Aug. 1999.

Budd, et al., "A Reevaluation of the Role of Mitochondria in Neuronal $Ca^{2+}$ Homeostasis," *J. Neurochemistry* 66(1):403–411, Jan. 1996.

Chen et al., "Molecular Identification of the Ryanodine Receptor $Ca^{2+}$ Sensor," *J. Biol. Chem.* 273(24):14675–14678, Jun. 12, 1998.

Chiesi et al., "Inhibition of Rapid Ca–Release from Isolated Skeletal and Cardiac Sarcoplasmic Reticulum (SR) Membranes," *Biochemical and Biophysical Research Communications* 154(1):1–8, Jul. 15, 1988.

Cromptom et al., "On the Involvement of a Mitochondrial Pore in Reperfusion Injury," *Basic Research in Cardiology* 88(5): 513–523, Sep.–Oct. 1993.

Darley–Usmar et al., "Mitochondria, Oxygen and Reperfusion Damage," *Annals of Medicine* 23:583–588, 1991.

Dykens, "Free Radicals and Mitochondrial Dysfunction in Excitotoxicity and neurodegenerative Disease," in V. E. Koliatos and R.R. Ratan, eds., *Cell Death and Diseases of the Nervous System*, Humana Press, New Jersey, 1999, pp. 45–68.

Dykens, "Isolated Cerebral and Cerebellar Mitochondria Produce Free Radicals when Exposed to Elevated $CA^{2+}$ and $Na^+$:Implications for Neurodegneration," *J. Neurochemistry* 63(2):584–591, Aug. 1994.

Dykens, "Mitochondrial Radical Production and Mechanisms of Oxidative Excitotoxicity" in K.J.A. Davies, and F. Ursini, eds., *The Oxygen Paradox*, Cleup Press, U. of Padova, 1995, pp. 453–467.

Dykens, *Mitochondria and Free Radicals in Neurodegenerative Diseases*, Beal, Howell and Bodis–Wollner, Eds., Wiley–Liss Inc., New York, 1997, Chapter 3, "Mitochondrial Free Radical Production and Oxidative Pathophysiology: Implications for Neurodegenerative Disease," pp. 29–55.

Ellerby et al., "Establishment of a Cell–Free System of Neuronal Apoptosis: Comparison of Premitochondrial, Mitochondrial, and Postmitochondrial Phases," *J. Neuroscience* 17(16):6165–6178, Aug. 15, 1997.

Emerson et al., "The Component of "Ruthenium Red" Responsible for Inhibition of Mitochondrial Calcium Ion Transport. Spectra, Electrochemistry, and Aquation Kinetics. Crystal Structure of $\mu$—O—$[(HCO_2)(NH_3)_4Ru]_2Cl_3$," *J. Amer. Chem. Soc.* 115:11799–11805, 1993.

Ernster et al., "Mitochondria: A Historical Review," *J. of Cell Biology* 91(3Pt.2):227s–255s, Dec. 1981.

Fiskum et al., "The Cytoskeleton of Digitonin–Treated Rat Hepatocytes," *Proc. Nat. Acad. Sci. USA* 77(6):3430–3434, Jun. 1980.

Green et al., "Mitochondria and Apoptosis," *Science* 281:1309–1312, Aug. 28, 1998.

Green, "Apoptotic Pathways: The Roads to Ruin," *Cell* 94:695–698, Sep. 18, 1998.

Guerini, "Calcineurin: Not Just a Simple Protein Phosphatase," *Biochem. Biophys. Res. Commun.* 235:271–275, 1997.

Gunter and Gunter, "Transport of Calcium by Mitochondria," *J. Bioenergetics and Biomembranes* 26(5): 471–485, 1994.

Gunter et al., "The $Ca^{2+}$ Transport Mechanisms of Mitochondria and $Ca^{2+}$ Uptake From Physiological–Type $Ca^{2+}$ Transients," *Biochim. Biophys. Acta* 1366:5–15, 1998.

Gunter et al., "Mechanisms by Which Mitochondria Transport Calcium." *Am. J. Physiol.*258 *(Cell Physiol. 27):* C755–C786, May 1990.

Gunter et al., "Mitochondrial Calcium Transport: Physiological and Pathological Relevance," *Am. J. Physiol.* 267*(Cell Physiol. 36):*C313–C339, Aug. 1994.

Hatanaka et al., "A Role of Peroxides in $Ca^{2+}$ Ionophore–Induced Apoptosis in Cultured Rat Cortical Neurons," *Biochem. Biophys. Res. Commun.* 227(2):513–518, Oct. 14, 1996.

Hepworth et al., "Okadaic Acid Induces the Release of $Ca^{2+}$ from Intracellular Stores in ECV304 Endothelial Cells," *Cell Calcium* 21(6):461–467, Jun. 1997.

Heytler, "Uncouplers of Oxidative Phosphorylation," *Pharmacol. Ther.* 10(3):461–472, 1980.

Heytler, "Uncouplers of Oxidative Phosphorylation," *Methods of Enzymology* 55:462–472, 1979.

Hockerman et al., "Molecular Determinants of Drug Binding and Action on L–Type Calcium Channels," *Annu. Rev. Pharmacol. Toxicol.* 37:361–369, 1997.

Hurley, "Kinetics of High–Affinity $Ca^{2+}$ Sequestration in Permeabilized Rat Pancreatic Acini," *Am. J. Physiol.* 254*(Cell Physiol. 23):*C621–C627, May 1988.

Ikura, "Calcium Binding and Conformation Response in EF–Hand Proteins," *TIBS* 21:14–17, Jan. 1996.

Jan and Jan, "Tracing the Roots of Ion Channels," *Cell* 69:715–718, May 29, 1992.

Jürgensmeier et al., "Bax Directly Induces Release of Cytochrome c from Isolated Mitochondria," *Proc. Natl. Acad. Sci. USA* 95:4997–5002, Apr. 1998.

Jurkowitz–Alexander et al., "Cell Swelling, Blebbing, and Death Are Dependent on ATP Depletion and Independent of Calcium During Chemical Hypoxia in a Glial Cell Line (ROC–1)," *J. Neurochemistry* 59:344352, 1992.

Kakalis et al., "Characterization of the Calcium–Binding Sites of Calcineurin B," *FEBS Letters* 362:55–58, 1995.

Kapùs et al., "Is the Mitochondrial Ca$^{2+}$ Uniporter a Voltage–Modulated Transport Pathway?," *FEBS Lett.* 282(1):61–64, Apr. 22, 1991.

Kroemer et al., "The Mitochondrial Death/Life Regulator in Apoptosis and Necrosis," *Annu. Rev. Physiol.* 60:619–642, 1998.

Kroemer, "The Proto–Oncogene Bcl–2 and Its Role in Regulating Apoptosis," *Nature Medicine* 3(6):614–620, Jun. 1997.

Leist and Nicotera, "Calcium and Neuronal Death," *Rev. Physiol. Biochem. Pharmacol.* 132:79, 1998.

Levy et al., "Alkali Cation Transport Through Liposomes by the Antimicrobial Fusafungine and its Constitutive Enniatins," *Biochem. Pharmacol.* 50(12):2105–2107, Dec. 22, 1995.

Li et al., "Amelioration by Cyclosporin A of Brain Damage Following 5 or 10 min of Ischemia in Rats Subjected to Preischemic Hyperglycemia," *Brain Research* 753(1):133–140, Apr. 4, 1997.

Liu et al., "Induction of Apoptotic Program in Cell–Free Extracts: Requirement for dATP an Cytochrome c," *Cell* 86:147–157, Jul. 12, 1996.

Low et al., "Effects of Thapsigargin and Ryanodine on Vascular Contractility: Cross–talk Between Sacroplasmic Reticulum and Plasmalemma," *Eur. J. Pharmacol.* 230(1):53–62, Jan. 5, 1993.

Matlib et al., "Oxygen–Bridged Dinuclear Ruthenium Amine Complex Specifically Inhibits Ca$^{2+}$ Uptake into Mitochondria In Vitro and In Situ in Single Cardiac Myocytes," *J. Biol. Chem.* 273(17):10223–10231, Apr. 24, 1998.

McCormack et al., "Studies on Mitochondrial Ca$^{2+}$–Transport and Matrix Ca$^{2+}$ Using Fura–2–Loaded Rat Heart Mitochondria," *Biochim. Biophys. Acta* 973:420–427, 1989.

Møller et al., "Charge Screening by Cations Affects the Conformation of the Mitochondrial Inner Membrane. A Study of Exogenous MAD(P)H Oxidation in Plant Mitochondria," *Biochem. J* 195(3):583–588, Jun. 1, 1981.

Murphy et al., "Bcl–2 Potentiates the Maximal Calcium Uptake Capacity of Neural Cell Mitochondria," *Proc. Natl. Acad. Sci. USA* 93:9893–9898, Sep. 1996.

Murphy et al., *Mitochondria and Free Radicals in Neurodegenerative Diseases,* Beal, Howell and Bodis–Wollner, Eds., Wiley–Liss, New York, 1998, Chapter 8, "Mitochondria, Reactive Oxygen Species, and Apoptosis," pp. 159–186.

Muscari et al., "Mitochondrial Function and Superoxide Generation from Submitochondrial Particles of Aged Rat Hearts," *Biochim. Biophys. Acta* 1015(2):200–204, Feb. 2, 1990.

Newmeyer et al., "Cell–Free Apoptosis in Xenopus Egg Extracts: Inhibition by Bcl–2 and Requirement for an Organelle Fraction Enriched in Mitochondria," *Cell* 79:353–364, Oct. 12, 1994.

Obatomi and Bach, "Inhibition of Mitochondrial Respiration and Oxygen Uptake in Isolated Rat Renal Tubular Fragments by Atractyloside," *Toxicol. Lett.* 89:155–161, 1996.

Orrenius and Nicotera, "The Calcium Ion and Cell Death," *J. Neural. Transm.* 43[Suppl.]:1–11, 1994.

Pereschini et al., "The EF–Hand Family of Calcium–Modulated Proteins," *TINS* 12(11):462–467, 1989.

Petronilli et al., "Transient and Long–Lasting Openings of the Mitochonrial Permeability Transaction Pore Can Be Monitored Directly in Intact Cells by Changes in Mitochondrial Calcein Fluorescence," *Biophysical Journal* 76:725–734, Feb. 1999.

Radi et al., *Mitochondria and Free Radicals in Neurodegenerative Diseases,* Beal, Howell and Bodis–Wollner, Eds., Wiley–Liss, New York, 1998, Chapter 4, "Free Radical Damage to Mitochondria," pp. 57–89.

Raff, "Cell Suicide for Beginners," *Nature* 396(6707):119–122, Nov. 12, 1998.

Reed et al., "The Inhibition of Mitochondrial Calcium Transport by Lanthanides and Ruthenium Red," *Biochem. J.* 140(2):143–155, May 1974.

Ridgley et al., "Reactive Oxygen Species Activate a Ca$^{2+}$–Depenedent Cell Death Pathway in the Unicellualr Organism *Trypanosoma brucei brucei,*" *Biochem. J.* 340:33–40, 1999.

Rottenberg et al., "Regulation of Ca$^{2+}$ Transport in Brain Mitochondria. II. The Mechanism of the Adenine Nucleotides Enhancement of Ca$^{2+}$ Uptake and Retention," *Biochim. Biophys. Acta* 1016(1):87–98, Mar. 15,1990.

Salvador et al., "Characterization of the Intracellular and the Plasma Membrane Ca$^{2+}$–ATPases in Fractionated Pig Brain Membranes Using Calcium Pump Inhibitors," *Arch. Biochem. Biophys.* 351(2):272–278, Mar. 15, 1998.

Sastrasinh et al., "Glutamine Transport in Submitochondrial Particles," *Am. J. Physiol. 257(Renal Fluid Electrolyte Physiol. 26)*:F1050–F1058, Dec. 1989.

Scorrano et al., "Chloromethyltetramethylrosamine (Mitotracker Orange™) Induces the Mitochondrial Permeability Transition and Inhibits Respiratory Complex I. Implications for the Mechanism of Cytochrome c Release," *J. Biol. Chem.* 274(35):24567–24663, Aug. 27, 1999.

Srivastava et al., "Atovaquone, a Broad Spectrum Antiparasitic Drug, Collapses Mitochondrial Membrane Potential in a Malarial Parasite," *J. Biol. Chem.* 272(7):3961–3966, Feb. 14, 1997.

Stout et al., "Glutamate–Induced Neuron Death Requires Mitochondrial Calcium Uptake," *Nature Neuroscience* 1(5):366–373, Sep. 1998.

Streb et al., "Release of Ca$^{2+}$ from a Nonmitochondrial Intracellular Store in Pancreatic Acinar Cells by Inositol–1, 4,5–Trisphosphate," *Nature* 306(5938):67–69, Nov. 3–9. 1983.

Susin et al., "Mitochondria as Regulators of Apoptosis: Doubt No More," *Biochemica et Biophysica Acta* 1366:151–165, 1998.

Szabó et al., "Modulation of the Mitochondrial Megachannel by Divalent Cations and Protons," *J. Biol. Chem.* 267(5):2940–2946, Feb. 15, 1992.

Takei et al., "Ca$^{2+}$ Ionophore–Induced Apoptosis on Cultured Embryonic Rat Cortical Neurons," *Brain Research* 652(1):65–70, 1994.

Takemura et al., "Activation of Calcium Entry by the Tumor Promoter Thapsigargin in Parotid Acinar Cells. Evidence that an Intracellular Calcium Pool and not an Inositol Phosphate Regulates Calcium Fluxes at the Plasma Membrane," *J. Biol. Chem.* 264(21):12266–12271, Jul. 25, 1989.

Tencé et al., "Synergistic Effects of Acetylcholine and Glutamate on the Release of Arachidonic Acid from Cultured Striatal Neurons," *J. Neurochem.* 64(4):1605–1613, Apr. 1995.

Thastrup et al., "Thapsigargin, a Novel Molecular Probe for Studying Intracellular Calcium Release and Storage," *Agents Actions* 27(1/2):17–23, Apr. 1989.

Tong et al., "Synaptic Desensitization of NMDA Receptors by Calcineurin," *Science* 267:1510–1512, Mar. 10, 1995.

White and Reynolds, "Miotochondrial Depolarization in Glutamine–Stimulated Neurons: An Early Signal Specific to Excitotoxin Exposure," *J. of Neuroscience* 16(18):5688–5697, Sep. 15, 1996.

Williams et al., "Structure and Functional Expression of an ω–Conotoxin–Sensitive Human N–type Calcium Channel," *Science* 257:389–395, Jul. 17, 1992.

Won et al., "Role of Inositol Trisphosphate–Sensitive Calcium Stores in the Regulation of Adrenocorticotropin Secretion by Perifused Rat Anterior Pituitary Cells," *Endocrinology* 136(12):5399–5408, Dec. 1995.

Xie et al., "Structure of the Regulatory Domain of Scallop Myosin at 2.8 Å Resolution," *Nature* 368:306–312, Mar. 24, 1994.

Yan et al., "Activation of Muscarinic Cholinergic Receptors Blocks Apoptosis of Cultured Cerebellar Granule Neurons," *Molecular Pharmacology* 47(2):248–257, Feb. 1995.

Ying et al., "Inhibition of Mitochondrial Calcium Ion Transport by an Oxo–Bridged Dinuclear Ruthenium Amine Complex," *Biochemistry* 30(20):3939–4952, May 21, 1991.

Zoratti and Szaboò, "The Mitochondrial Permeability Transition," *Biochimica et Biophysica Acta* 1241:139–176, 1995.

* cited by examiner

SCREENING ASSAYS USING INTRAMITOCHONDRIAL CALCIUM

CROSS-REFERENCES TO RELATED APPLICATIONS

This application claims the benefit of U.S. Provisional Application No. 60/176,384 filed Jan. 14, 2000, which is incorporated herein by reference in its entirety.

TECHNICAL FIELD

The invention relates generally to assays for screening for agents that affect mitochondrial activity. More specifically, the invention is directed to screening methods for use in identifying agents that alter mitochondrial regulation of intracellular calcium. An assay for the presence of extramitochondrial calcium and for factors that influence levels of intramitochondrial and/or extramitochondrial calcium, such as the calcium uniporter (CaUP), is provided herein.

BACKGROUND OF THE INVENTION

Mitochondria are organelles that are the main energy source in cells of higher organisms. These organelles provide direct and indirect biochemical regulation of a wide array of cellular respiratory, oxidative and metabolic processes, including metabolic energy production, aerobic respiration and intracellular calcium regulation. For example, mitochondria are the site of electron transport chain (ETC) activity, which drives oxidative phosphorylation to produce metabolic energy in the form of adenosine triphosphate (ATP), and which also underlies a central mitochondrial role in intracellular calcium homeostasis. These processes require the maintenance of a mitochondrial membrane electrochemical potential, and defects in such membrane potential can result in a variety of disorders.

In addition to their role in energy production in growing cells, mitochondria (or at least mitochondrial components) participate in programmed cell death (PCD), also known as apoptosis (see Newmeyer et al., *Cell* 79:353–364, 1994; Liu et al., *Cell* 86:147–157, 1996). Apoptosis is apparently required for normal development of the nervous system and functioning of the immune system. Some disease states are associated with insufficient apoptosis (e.g., cancer and autoimmune diseases) or excessive levels of apoptosis (e.g., stroke and neurodegeneration). For general reviews of apoptosis, and the role of mitochondria therein, see Green and Reed, *Science* 281:1309–1312, 1998; Green, *Cell* 94:695–698, 1998; and Kromer, *Nature Medicine* 3:614–620, 1997.

Mitochondria contain an outer mitochondrial membrane that serves as an interface between the organelle and the cytosol, a highly folded inner mitochondrial membrane that appears to form attachments to the outer membrane at multiple sites, and an intermembrane space between the two mitochondrial membranes. The subcompartment within the inner mitochondrial membrane is commonly referred to as the mitochondrial matrix (for review, see, e.g., Emster et al., *J. Cell Biol.* 91:227s, 1981). While the outer membrane is freely permeable to ionic and non-ionic solutes having molecular weights less than about ten kilodaltons, the inner mitochondrial membrane exhibits selective and regulated permeability for many small molecules, including certain cations, and is impermeable to large (greater than about 10 kD) molecules.

Four of the five multisubunit protein complexes (Complexes I, III, IV and V) that mediate ETC activity are localized to the inner mitochondrial membrane. The remaining ETC complex (Complex II) is situated in the matrix. In at least three distinct chemical reactions known to take place within the ETC, protons are moved from the mitochondrial matrix, across the inner membrane, to the intermembrane space. This disequilibrium of charged species creates an electrochemical membrane potential of approximately 220 mV referred to as the "protonmotive force" (PMF). The PMF, which is often represented by the notation $\Delta p$, corresponds to the sum of the electric potential ($\Delta\Psi m$) and the pH differential ($\Delta pH$) across the inner membrane according to the equation $$\Delta p = \Delta\Psi m - Z\Delta pH$$

wherein Z stands for $-2.303$ RT/F. The value of Z is $-59$ at 25° C. when $\Delta p$ and $\Delta\Psi m$ are expressed in mV and $\Delta pH$ is expressed in pH units (see, e.g., Emster et al., *J. Cell Biol.* 91:227s, 1981, and references cited therein).

$\Delta\Psi m$ provides the energy for phosphorylation of adenosine diphosphate (ADP) to yield ATP by ETC Complex V, a process that is coupled stoichiometrically with transport of a proton into the matrix. $\Delta\Psi m$ is also the driving force for the influx of cytosolic $Ca^{2+}$ into the mitochondrion. Under normal metabolic conditions, the inner membrane is largely impermeable to proton movement from the intermembrane space into the matrix, leaving ETC Complex V as the primary means whereby protons can return to the matrix. When, however, the integrity of the inner mitochondrial membrane is compromised, as occurs during mitochondrial permeability transition (MPT) that accompanies certain diseases associated with altered mitochondrial function, protons are able to bypass the conduit of Complex V without generating ATP, thereby uncoupling respiration (i.e., ETC activity) from ATP production. During MPT, $\Delta\Psi m$ collapses and mitochondrial membranes lose the ability to selectively regulate permeability to solutes both small (e.g., ionic $Ca^{2+}$, $Na^+$, $K^+$ and $H^+$) and large (e.g., proteins). Loss of mitochondrial potential also appears to be a critical event in the progression of diseases associated with altered mitochondrial function, including degenerative diseases such as Alzheimer's Disease; diabetes mellitus; Parkinson's Disease; Huntington's disease; dystonia; Leber's hereditary optic neuropathy; schizophrenia; mitochondrial encephalopathy, lactic acidosis, and stroke (MELAS); cancer; psoriasis; hyperproliferative disorders; mitochondrial diabetes and deafness (MIDD) and myoclonic epilepsy ragged red fiber syndrome.

Normal alterations of intramitochondrial $Ca^{2+}$ are associated with normal metabolic regulation (Dykens, 1998 in *Mitochondria & Free Radicals in Neurodegenerative Diseases*, Beal, Howell and Bodis-Wollner, Eds., Wiley-Liss, New York, pp. 29–55; Radi et al., 1998 in *Mitochondria & Free Radicals in Neurodegenerative Diseases*, Beal, Howell and Bodis-Wollner, Eds., Wiley-Liss, New York, pp. 57–89; Gunter and Pfeiffer, 1991, *Am. J. Physiol.* 27: C755; Gunter et al., *Am. J. Physiol.* 267:313, 1994). For example, fluctuating levels of mitochondrial free $Ca^{2+}$ may be responsible for regulating oxidative metabolism in response to increased ATP utilization, via allosteric regulation of enzymes (reviewed by Crompton and Andreeva, *Basic Res. Cardiol.* 88:513–523, 1993); and the glycerophosphate shuttle (Gunter and Gunter, *J. Bioenerg. Biomembr.* 26:471, 1994).

Normal mitochondrial function includes regulation of cytosolic free calcium levels by sequestration of excess $Ca^{2+}$ within the mitochondrial matrix. Depending on cell type, cytosolic $Ca^{2+}$ concentration is typically 50–100 nM. In normally functioning cells, when $Ca^{2+}$ levels reach 200–300 nM, mitochondria begin to accumulate $Ca^{2+}$ as a function of the equilibrium between influx via a $Ca^{2+}$ uniporter in the inner mitochondrial membrane and $Ca^{2+}$ efflux via both $Na^+$ dependent and $Na^+$ independent calcium carriers. The low affinity of this rapid uniporter mechanism suggests that the primary uniporter function may be to lower cytosolic $Ca^{2+}$ in response to pathological elevation of cytosolic free calcium levels, which may result from ATP depletion and/or abnormal calcium influx across the plasma membrane (Gunter and Gunter, *J. Bioenerg. Biomembr.* 26:471, 1994; Gunter et al., *Am. J. Physiol.* 267:313, 1994). In certain instances, such perturbation of intracellular calcium homeostasis is a feature of diseases associated with altered mitochondrial function, regardless of whether the calcium regulatory dysfunction is causative of, or a consequence of, altered mitochondrial function including MPT.

In view of the significance of mitochondrial regulation of intracellular calcium and the relationship of this mitochondrial activity to several disease states, there is clearly a need for improved compositions and methods to control mitochondrial calcium homeostasis. To provide improved therapies for such diseases, agents that alter mitochondrial calcium regulation may be beneficial, and assays to specifically detect such agents are needed. The present invention fulfills these needs and further provides other related advantages.

SUMMARY OF THE INVENTION

The present invention is directed in part to methods for identifying agents that alter mitochondrial regulation of intracellular calcium. Thus, in one aspect the invention provides a method of identifying an agent that alters mitochondrial function, comprising (a) contacting, in each of a plurality of reaction vessels in a high throughput screening array, (i) a biological sample comprising a cell containing cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cytosol; (b) detecting in each reaction vessel the signal generated by the calcium indicator molecule at a plurality of time points; and (c) comparing the signal generated by the calcium indicator molecule at one or more of the time points in the absence of a candidate agent, to the signal generated by the calcium indicator molecule at one or more of the time points in the presence of the candidate agent, and therefrom identifying an agent that alters mitochondrial function. In one embodiment the step of contacting is repeated at least once. In another embodiment the sample contains at least one compound that alters intracellular distribution of a calcium cation. In a further embodiment the compound that alters intracellular calcium cation distribution is thapsigargin or Ru360. In another embodiment the compound that alters intracellular calcium cation distribution is a calcium ionophore or a membrane permeable compound that alters intracellular calcium distribution. In another embodiment the sample contains at least one compound that uncouples oxidative phosphorylation from ATP production. In another embodiment the candidate agent is membrane permeable, and in another embodiment the calcium indicator molecule is membrane permeable. In another embodiment the source of calcium cations is exogenous to the cell. In another embodiment the sample contains at least one compound that uncouples oxidative phosphorylation from ATP production. In another embodiment the cell comprises at least one polypeptide that is a member of the Bcl-2 family. In another embodiment the cell expresses a gene encoding a polypeptide that regulates cytosolic calcium. In another embodiment the gene encodes a mitochondrial calcium uniporter. In another embodiment the gene is a transfected gene. In another embodiment the gene encodes a mitochondrial calcium uniporter. In another embodiment the cell is a permeabilized cell. In certain embodiments the cell adheres to a solid substrate and in certain other embodiments the cell is a non-adherent cell.

It is another aspect of the present invention to provide a method of identifying an agent that uncouples oxidative phosphorylation from ATP production, comprising (a) contacting, in each of a plurality of reaction vessels in a high throughput screening array, (i) a biological sample comprising a cell containing cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cytosol; (b) detecting in each reaction vessel the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent, to (ii) the signal generated by the calcium indicator molecule at one or more of the time points prior to and following at least one of the contacting steps in the presence of the candidate agent, wherein an increased level of calcium in the cytosol at a time point prior to a contacting step in the presence of the agent, compared to the level of calcium in the cytosol prior to a contacting step in the absence of the agent, indicates an agent that uncouples oxidative phosphorylation from ATP production.

In another aspect the invention provides a method of identifying an agent that that is a respiratory inhibitor, comprising: (a) contacting, in each of a plurality of reaction vessels in a high throughput screening array, (i) a biological sample comprising a cell containing cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cytosol; (b) detecting in each reaction vessel the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent, to (ii) the signal generated by the calcium indicator molecule at one or more of the time points prior to and following at least one of the contacting steps in the presence of the candidate agent, wherein an increased level of calcium in the cytosol at a time point prior to a contacting step in the presence of the agent, compared to the level of calcium in the cytosol prior to a contacting step in the absence of the agent, indicates an agent that is a respiratory inhibitor.

In another embodiment the invention provides a method of identifying an agent that alters a mitochondrial calcium uniporter, comprising: (a) contacting, in each of a plurality of reaction vessels in a high throughput screening array, (i) a biological sample comprising a cell containing cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cytosol; (b) detecting in each reaction vessel the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent, to (ii) the signal generated by the calcium indicator molecule at one or more of the time points prior to and following at least one of the contacting steps in the presence of the candidate agent, wherein an increased level of calcium in the cytosol at a time point following a contacting step in the presence of the agent, compared to the level of calcium in the cytosol following a contacting step in the absence of the agent, indicates that the agent alters a mitochondrial calcium uniporter.

In another embodiment there is provided a method of identifying an agent that alters mitochondrial function, comprising (a) contacting (i) a biological sample comprising a cell containing cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cytosol; (b) detecting the signal generated by the calcium indicator molecule at a plurality of time points; and (c) comparing the signal generated by the calcium indicator molecule at one or more of the time points in the absence of the candidate agent, to the signal generated by the calcium indicator molecule at one or more of the time points in the presence of the candidate agent, and therefrom identifying an agent that alters mitochondrial function. In one embodiment the step of contacting is repeated at least once. In another embodiment the sample contains at least one compound that alters intracellular distribution of a calcium cation. In another embodiment the compound that alters intracellular calcium cation distribution is thapsigargin or Ru360. In another embodiment the compound that alters intracellular calcium cation distribution is selected from the group consisting of a calcium ionophore and a membrane permeable compound that alters intracellular calcium distribution. In another embodiment the sample contains at least one compound that uncouples oxidative phosphorylation from ATP production. In another embodiment the candidate agent is membrane permeable. In another embodiment the calcium indicator molecule is membrane permeable. In another embodiment the source of calcium cations is exogenous to the cell. In another embodiment the sample contains at least one compound that uncouples oxidative phosphorylation from ATP production. In another embodiment the cell comprises at least one polypeptide that is a member of the Bcl-2 family. In another embodiment the cell expresses a gene encoding a polypeptide that regulates cytosolic calcium. In another embodiment the gene encodes a mitochondrial calcium uniporter. In another embodiment the gene is a transfected gene. In another embodiment the gene encodes a mitochondrial calcium uniporter. In another embodiment the cell is a permeabilized cell. In another embodiment the cell adheres to a solid substrate. In another embodiment the cell is a non-adherent cell.

In still another embodiment the invention provides a method of identifying an agent that uncouples oxidative phosphorylation from ATP production, comprising: (a) contacting (i) a biological sample comprising a cell containing cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cytosol; (b) detecting the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent, to (ii) the signal generated by the calcium indicator molecule at one or more of the time points prior to and following at least one of the contacting steps in the presence of the candidate agent, wherein an increased level of calcium in the cytosol at a time point prior to a contacting step in the presence of the agent, compared to the level of calcium in the cytosol prior to a contacting step in the absence of the agent, indicates an agent that uncouples oxidative phosphorylation from ATP production.

In another embodiment the invention provides a method of identifying an agent that is a respiratory inhibitor, comprising: (a) contacting (i) a biological sample comprising a cell containing cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cytosol; (b) detecting the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent, to (ii) the signal generated by the calcium indicator molecule at one or more of the time points prior to and following at least one of the contacting steps in the presence of the candidate agent, wherein an increased level of calcium in the cytosol at a time point prior to a contacting step in the presence of the agent, compared to the level of calcium in the cytosol prior to a contacting step in the absence of the agent, indicates an agent that is a respiratory inhibitor.

In another embodiment the invention provides a method of identifying an agent that alters a mitochondrial calcium uniporter, comprising (a) contacting, (i) a biological sample comprising a cell containing cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cytosol; (b) detecting the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent, to (ii) the signal generated by the calcium indicator molecule at one or more of the time points prior to and following at least one of the contacting steps in the presence of the candidate agent, wherein an increased level of calcium in the cytosol at a time point following a contacting step in the presence of the agent, compared to the level of calcium in the cytosol following a contacting step in the absence of the agent, indicates that the agent alters a mitochondrial calcium uniporter.

In another embodiment the invention provides a method of identifying an agent that alters mitochondrial function, comprising: (a) contacting, in each of a plurality of reaction vessels in a high throughput screening array, (i) a biological sample comprising a cell containing a mitochondrion, cytosol and a calcium indicator molecule, under conditions that permit maintenance of mitochondrial membrane potential, and wherein the calcium indicator molecule is membrane permeable and capable of generating a detectable signal that is proportional to the level of calcium in the cytosol, with (ii) a calcium ionophore, under conditions and for a time sufficient to increase calcium levels within the cell; (b) detecting in each reaction vessel the signal generated by the calcium indicator molecule at a plurality of time points; and (c) comparing the signal generated by the calcium indicator molecule at one or more of the time points in the absence of the candidate agent, to the signal generated by the calcium indicator molecule at one or more of the time points in the presence of the candidate agent, and therefrom identifying an agent that alters mitochondrial function.

In another embodiment the calcium ionophore is ionomycin, A23187, NMDA or a cell depolarization signal. In another embodiment the step of contacting is repeated at least once. In another embodiment the sample contains at least one compound that alters intracellular distribution of a calcium cation. In another embodiment the compound that alters intracellular calcium cation distribution is thapsigargin or Ru360. In another embodiment the compound that alters intracellular calcium cation distribution is a calcium ionophore or a membrane permeable compound that alters intracellular calcium distribution. In another embodiment the sample contains at least one compound that uncouples oxidative phosphorylation from ATP production. In another embodiment the candidate agent is membrane permeable. In another embodiment the source of calcium cations is exogenous to the cell. In another embodiment the sample contains at least one compound that uncouples oxidative phosphorylation from ATP production. In another embodiment the cell comprises at least one polypeptide that is a member of the Bcl-2 family. In another embodiment the cell expresses a gene encoding a polypeptide that regulates cytosolic calcium. In certain further embodiments the gene encodes a mitochondrial calcium uniporter, and in certain other embodiments the gene is a transfected gene. In certain further embodiments the gene encodes a mitochondrial calcium uniporter. In another embodiment the cell adheres to a solid substrate, and in certain other embodiments the cell is a non-adherent cell.

In another embodiment the invention provides a method of identifying an agent that uncouples oxidative phosphorylation from ATP production, comprising (a) contacting (i) a biological sample comprising a cell containing cytosol, a mitochondrion and a calcium indicator molecule, under conditions that permit maintenance of mitochondrial membrane potential, and wherein the calcium indicator molecule is membrane permeable and capable of generating a detectable signal that is proportional to the level of calcium in the cytosol, with (ii) a calcium ionophore, under conditions and for a time sufficient to increase calcium levels within the cell; (b) detecting the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent to (ii) the signal generated by the calcium indicator molecule at one or more of the time points prior to and following at least one of the contacting steps in the presence of the candidate agent, wherein an increased level of calcium in the cytosol at a time point prior to a contacting step in the presence of the agent, compared to the level of calcium in the cytosol prior to a contacting step in the absence of the agent, indicates an agent that uncouples oxidative phosphorylation from ATP production.

In another embodiment the invention provides a method of identifying an agent that is a respiratory inhibitor, comprising: (a) contacting (i) a biological sample comprising a cell containing cytosol, a mitochondrion and a calcium indicator molecule, under conditions that permit maintenance of mitochondrial membrane potential, and wherein the calcium indicator molecule is membrane permeable and capable of generating a detectable signal that is proportional to the level of calcium in the cytosol, with (ii) a calcium ionophore, under conditions and for a time sufficient to increase calcium levels within the cell; (b) detecting the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent to (ii) the signal generated by the calcium indicator molecule at one or more of the time points prior to and following at least one of the contacting steps in the presence of the candidate agent, wherein an increased level of calcium in the cytosol at a time point prior to a contacting step in the presence of the agent, compared to the level of calcium in the cytosol prior to a contacting step in the absence of the agent, indicates an agent that is a respiratory inhibitor.

In another embodiment the invention provides a method of identifying an agent that alters a mitochondrial calcium uniporter, comprising (a) contacting (i) a biological sample comprising a cell containing cytosol, a mitochondrion and a calcium indicator molecule, under conditions that permit maintenance of mitochondrial membrane potential, and wherein the calcium indicator molecule is membrane permeable and capable of generating a detectable signal that is proportional to the level of calcium in the cytosol, with (ii) a calcium ionophore, under conditions and for a time sufficient to increase calcium levels within the cell; (b) detecting the signal generated by the calcium indicator molecule at a plurality of time points; (c) repeating steps (a) and (b) at least once; and (d) comparing (i) the signal generated by the calcium indicator molecule at one or more of the time points prior to and following at least one of the contacting steps in the absence of the candidate agent to (ii) the signal generated by the calcium indicator molecule at one or more of the time points prior to and following at east one of the contacting steps in the presence of the candidate agent, wherein an increased level of calcium in the cytosol at a time point following a contacting step in the presence of the agent, compared to the level of calcium in the cytosol following a contacting step in the absence of the agent, indicates that the agent alters a mitochondrial calcium uniporter.

It is another aspect of the invention to provide a method of identifying an agent that alters mitochondrial function, comprising (a) contacting (i) a biological sample comprising a permeabilized cell depleted of cytosol, a mitochondrion and a calcium indicator molecule, under conditions that permit maintenance of mitochondrial membrane potential, with (ii) a source of calcium cations, wherein the calcium indicator molecule is capable of generating a detectable signal that is proportional to the level of calcium in the cell;

(b) detecting the signal generated by the calcium indicator molecule at a plurality of time points; and (c) comparing the signal generated by the calcium indicator molecule at one or more of the time points in the absence of a candidate agent, to the signal generated by the calcium indicator molecule at one or more of the time points in the presence of the candidate agent, and therefrom identifying an agent that alters mitochondrial function. In another related embodiment there is provided such a method in a high throughput screening format, wherein the step of contacting is performed in each of a plurality of reaction vessels in a high throughput screening array, and the step of detecting is performed in each reaction vessel.

According to certain further embodiments, the calcium indicator molecule is capable of generating a detectable signal that is proportional either to the level of calcium in the mitochondrion or to the level of calcium outside of the mitochondrion. In certain other further embodiments the step of contacting is repeated at least once. In certain other further embodiments the sample contains at least one compound that alters intracellular distribution of a calcium cation. In a still further embodiment the compound that alters intracellular calcium cation distribution is thapsigargin or Ru360. In another embodiment the sample contains at least one compound that uncouples oxidative phosphorylation from ATP production. In another embodiment the source of calcium cations is exogenous to the cell, and in another embodiment the sample contains at least one compound that uncouples oxidative phosphorylation from ATP production. In certain embodiments the cell comprises at least one polypeptide that is a Bcl-2 family member, and in certain other embodiments the cell expresses a gene encoding a polypeptide that regulates cytosolic calcium. In a further embodiment the gene encodes a mitochondrial calcium uniporter, and in a distinct further embodiment the gene is a transfected gene. In a still further embodiment the gene encodes a mitochondrial calcium uniporter. According to certain embodiments the cell adheres to a solid substrate, while in certain other embodiments the cell is a non-adherent cell.

In another embodiment the present invention provides a method of identifying an agent that alters mitochondrial function, comprising (a) contacting (i) a biological sample comprising one or more isolated mitochondria and a calcium indicator molecule in a medium, under conditions that permit maintenance of mitochondrial membrane potential, with (ii) a source of calcium cations, wherein the calcium indicator molecule is capable of generating a detectable signal that is proportional to the level of calcium in the biological sample; (b) detecting the signal generated by the calcium indicator molecule at a plurality of time points; and (c) comparing the signal generated by the calcium indicator molecule at one or more of the time points in the absence of a candidate agent, to the signal generated by the calcium indicator molecule at one or more of the time points in the presence of the candidate agent, and therefrom identifying an agent that alters mitochondrial function. In another related embodiment there is provided such a method in a high throughput screening format, wherein the step of contacting is performed in each of a plurality of reaction vessels in a high throughput screening array, and the step of detecting is performed in each reaction vessel.

In certain further embodiments the calcium indicator molecule is capable of generating a detectable signal that is proportional to the level of calcium in the mitochondrion, and in certain other further embodiments the calcium indicator molecule is capable of generating a detectable signal that is proportional to the level of calcium outside of the mitochondrion. In certain embodiments the step of contacting is repeated at least once. In another embodiment the sample contains at least one compound that alters distribution of a calcium cation in the sample, which in certain further embodiments is thapsigargin or Ru360. In another embodiment the sample contains at least one compound that uncouples oxidative phosphorylation from ATP production, and in another embodiment the isolated mitochondria are derived from a cell that comprises at least one polypeptide that is a Bcl-2 family member. In certain other embodiments the isolated mitochondria are derived from a cell that expresses a gene encoding a polypeptide that regulates cytosolic calcium, and in certain further embodiments the gene encodes a mitochondrial calcium uniporter. In certain other embodiments the gene is a transfected gene, and in certain further embodiments the gene encodes a mitochondrial calcium uniporter.

In certain further embodiments of invention methods described above, subsequent to the step of contacting the biological sample with the source of calcium cations and prior to the step of comparing signals, the biological sample is contacted (i) with at least one compound that uncouples oxidative phosphorylation from ATP production, and (ii) with at least one agent that alters mitochondrial function. In some embodiments the agent that alters mitochondrial function is cyclosporin A, and in certain other embodiments the agent is cyclosporin A, rotenone, oligomycin, succinate or Bcl-2. In certain embodiments the compound that uncouples oxidative phosphorylation from ATP production is FCCP or CCCP.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
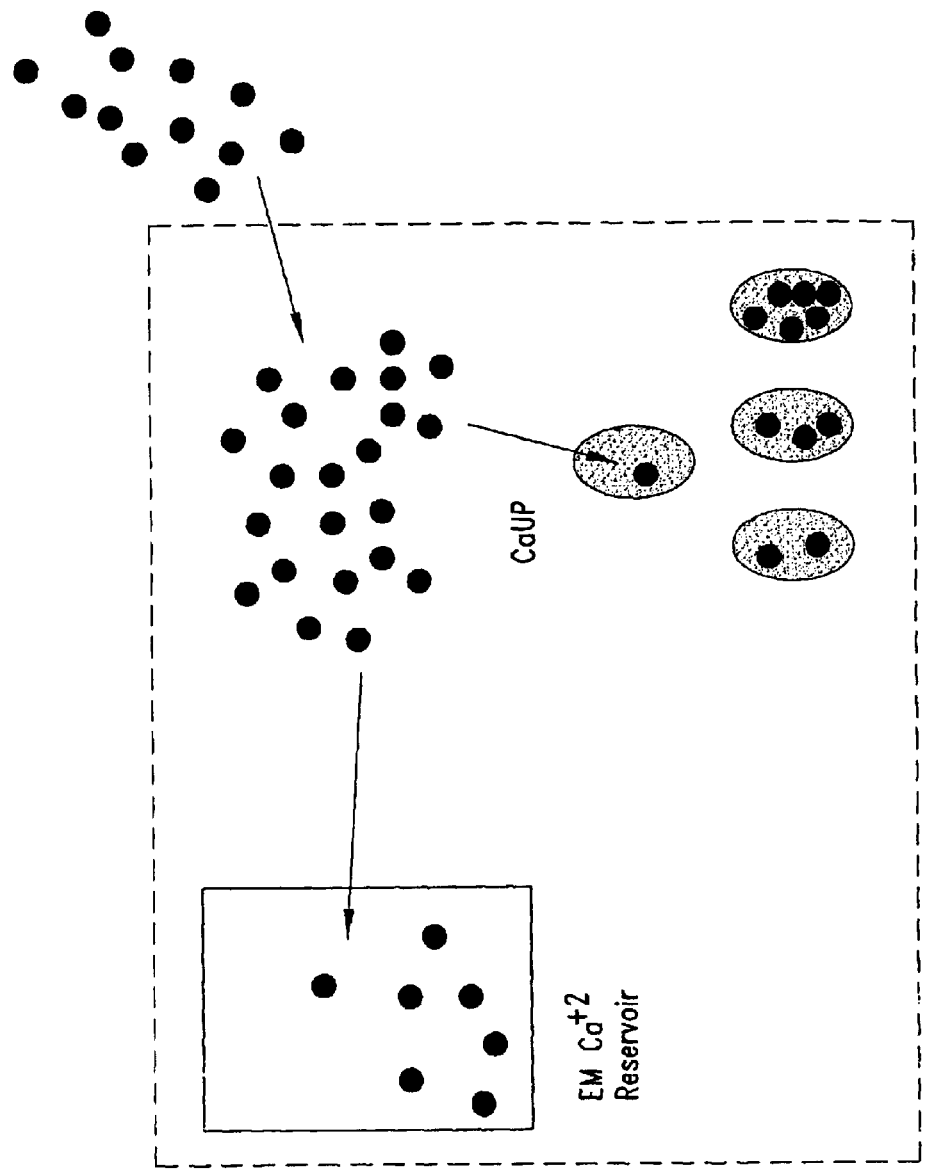
FIG. 1 depicts the entry and distribution of calcium ions ($Ca^{2+}$, represented as "●" in the figure) into permeabilized cells. Other symbols and abbreviations: dashed line, permeabilized cell membrane; ovals, mitochondria; rectangle with solid border, extramitochondrial (EM) calcium reservoir; CaUP, mitochondrial calcium uniporter.

The present invention provides methods for identifying compounds that alter mitochondrial function, and in particular, that influence mitochondrial regulation of intracellular calcium levels, including high throughput screening assays for the detection of the physiological or pharmacological effect of a candidate agent. The invention is based in part on the unexpected adaptability of sensitive, cell-based metric techniques to a high throughput format, and on the ability to modify these techniques for screening panels of candidate agents such as drugs and pharmacophores. Additionally, the invention is based in part on the surprising observation that, through the use of a compound that alters intracellular calcium cation distribution, selective conditions can be devised for monitoring regulation by mitochondria of intracellular calcium in cell-based assays such as high throughput drug screening.

According to the present invention, a cell that contains cytosol, a mitochondrion and a calcium indicator molecule (or in certain embodiments, a permeabilized cell containing mitochondria, or a permeabilized cell containing mitochondria and depleted of cytosol, or a suspension of isolated mitochondria, in each case containing a calcium indicator molecule) is contacted one or more times with a source of calcium cations ($Ca^{2+}$) under conditions that permit maintenance of mitochondrial membrane potential, and a signal generated by the calcium indicator molecule, which signal is proportional to the level of calcium in the cytosol, is detected at a plurality of time points. Mitochondria that are capable of maintaining a membrane potential can regulate cytosolic free calcium levels, such that monitoring cytosolic calcium levels as described herein permits screening for and identification of agents that alter this and related mitochondrial functions, including mitochondrial calcium uniporter activity. By comparing the signal generated in the presence of the candidate agent to the signal generated in the absence of the agent, detection of an alteration (e.g., an increase or decrease) in the signal that accompanies the introduction of the agent can signify that the agent may usefully alter mitochondrial function.

Thus, as described in greater detail below, the present invention relates to compositions and methods for screening compounds that may alter mitochondrial function, including high throughput screening assays, by detecting changes in intracellular calcium levels that are regulated by mitochondrial activity. The screening assays of the present invention include assays that are performed using intact cells, and also include assays performed using permeabilized cells. As provided herein, in certain embodiments the present invention provides a method for identifying an agent that alters mitochondrial function, and in certain other embodiments the invention provides a method for identifying an agent that is a respiratory inhibitor. In certain other embodiments the invention provides a method for identifying an agent that uncouples oxidative phosphorylation from ATP production. In certain other embodiments the invention provides a method for identifying an agent that inhibits a mitochondrial calcium uniporter. Moreover, as disclosed herein, the subject invention methods permit distinguishing between certain types of agents that alter mitochondrial function. For example, based on the teachings herein, by detecting the signal generated over a period of time by a calcium indicator molecule as provided herein, a person having ordinary skill in the art can determine whether an agent inhibits a mitochondrial calcium uniporter or whether, alternatively, an agent may be a respiratory inhibitor or an uncoupler of oxidative phosphorylation from ATP production.

According to the present invention, and as described in greater detail below, a biological sample comprising a cell comprising cytosol, a mitochondrion and a calcium indicator molecule (or in certain embodiments, a permeabilized cell containing mitochondria, or a permeabilized cell containing mitochondria and depleted of cytosol, or in preferred embodiments a suspension of isolated mitochondria, in each case containing a calcium indicator molecule), is contacted with a source of calcium cations under conditions that permit maintenance of mitochondrial membrane potential, and a detectable signal generated by the calcium indicator molecule and proportional to the level of cytosolic calcium is detected at a plurality of time points. The step of contacting with a source of calcium cations may be optionally repeated at least once or a plurality of times, and the signal generated by the calcium indicator molecule at one or more of the time points in the absence of a candidate agent is compared to the signal generated by the calcium indicator molecule at one or more of the time points in the presence of the candidate agent.

According to non-limiting theory, an initial calcium-contacting step induces a transient elevation of detectable cytosolic calcium that, under control conditions, dissipates as calcium is imported into the mitochondria (FIG. 1A). If a candidate agent has no effect on mitochondrial function, a subsequent step of contacting with a source of calcium would similarly result in a transient rise in cytosolic calcium that dissipates as mitochondrial uptake of this cytosolic calcium proceeds (FIG. 1C). Depending on the particular biological sample and the quantity of calcium present, after one, two or more calcium-contacting steps, mitochondrial capacity for calcium uptake may be supra-saturated such that collapse of mitochondrial membrane potential and mitochondrial membrane permeability transition (MPT) are induced, leading to a detectable, spontaneous release of calcium from mitochondria into the cytosol. In preferred embodiments of the invention, at least two or three calcium-contacting steps would be required to induce this type of spontaneous calcium release.

If a candidate agent is present that uncouples oxidative phosphorylation from ATP production (i.e., a "respiratory uncoupler"), mitochondrial membrane potential dissipates and mitochondria release calcium back into the cytosol (e.g., via the calcium uniporter), generating a detectable increase in the signal produced by the calcium indicator molecule (FIG. 1B). If, however, a candidate agent is present that is an inhibitor of the calcium uniporter, mitochondrial uptake of cytosolic calcium is completely or partially impaired following one or several calcium-contacting steps, resulting in higher levels of detectable cytosolic calcium (FIG. 1D). Conversely, if a candidate agent is present that stimulates, augments or otherwise enhances calcium uniporter activity, mitochondrial uptake of calcium from the cytosol following a calcium-contacting step is detected as a decreased signal generated by the calcium indicator molecule (FIG. 1D). In certain embodiments of the invention, a compound that alters intracellular distribution of calcium cations may optionally be present, for example thapsigargin, ruthenium red (e.g., Ying et al., *Biochem.* 30:4949, 1991; Matlib et al., *J. Biol. Chem.* 273:10223, 1998), Ru360 (e.g., Emerson et al., *J. Am. Chem. Soc.* 115:11799, 1993), Bcl-2 (e.g., Murphy et al., *Proc. Nat. Acad. Sci. USA* 93:9893, 1996; U.S. Pat. No. 5,459,251) or one or more other suitable compounds. Optionally, additional compounds that may alter mitochondrial function may also be present, for example, chloromethyltetramethylrosamine (e.g., Scorrano et al., *Proc. Nat. Acad. Sci. USA* 274:24567, 1999), cyclosporin A (e.g., Petronilli et al., *Biophys. Jl.* 76:725, 1999; Murphy et al., *Proc. Nat. Acad. Sci. USA* 93:9893), rotenone, oligomycin or succinate (Murphy et al., 1996).

"Altered mitochondrial function" may refer to any condition or state, including those that accompany a disease associated with altered mitochondrial function, where any structure or activity that is directly or indirectly related to a mitochondrial function has been changed in a statistically significant manner relative to a control or standard. Altered mitochondrial function may have its origin in extramitochondrial structures or events as well as in mitochondrial structures or events, in direct interactions between mitochondrial and extramitochondrial genes and/or their gene products, or in structural or functional changes that occur as the result of interactions between intermediates that may be formed as the result of such interactions, including metabolites, catabolites, substrates, precursors, cofactors and the like.

Additionally, altered mitochondrial function may include altered respiratory, metabolic or other biochemical or biophysical activity in one or more cells of a biological sample or a biological source. As non-limiting examples, markedly impaired ETC activity may be related to altered mitochondrial function, as may be generation of increased reactive oxygen species (ROS) or defective oxidative phosphorylation. As further examples, altered mitochondrial membrane potential, induction of apoptotic pathways and formation of atypical chemical and biochemical crosslinked species within a cell, whether by enzymatic or non-enzymatic mechanisms, may all be regarded as indicative of altered mitochondrial function. These and other non-limiting examples of altered mitochondrial function are contemplated by the present invention.

Without wishing to be bound by theory, altered mitochondrial function may be related to altered intracellular calcium regulation that may, for example, accompany loss of mitochondrial membrane electrochemical potential by intracellular calcium flux, by mechanisms that include free radical oxidation, defects in transmitochondrial membrane shuttles and transporters such as the adenine nucleotide transporter or the malate-aspartate shuttle, by defects in ATP biosynthesis, by impaired association with porin of hexokinases and/or other enzymes or by other events. Altered intracellular calcium regulation and/or collapse of mitochondrial inner membrane potential may result from direct or indirect effects of mitochondrial genes, gene products or related downstream mediator molecules and/or extramitochondrial genes, gene products or related downstream mediators, or from other known or unknown causes. Thus, an "indicator of altered mitochondrial function" may be any detectable parameter that directly relates to a condition, process, pathway, dynamic structure, state or other activity involving mitochondria and that permits detection of altered mitochondrial function in a biological sample from a subject or biological source. According to non-limiting theory, altered mitochondrial function therefore may also include altered mitochondrial permeability to calcium or to mitochondrial molecular components involved in apoptosis (e.g., cytochrome c), or other alterations in mitochondrial respiration.

Certain aspects of the present invention as it relates to monitoring the activity of mitochondrial molecular components that bind, transport or otherwise regulate intracellular calcium involve the relationship between mitochondrial $\Delta\Psi$ and intracellular calcium homeostasis. The invention thus relates in part to detecting, in a biological sample comprising a cell containing cytosol, a mitochondrion and a calcium indicator molecule as provided herein, a signal generated by the calcium indicator molecule. Accordingly, in certain preferred embodiments altered mitochondrial function may be manifest as altered mitochondrial regulation of intramitochondrial and extramitochondrial calcium levels, as altered mitochondrial calcium uniporter activity, as altered mitochondrial membrane potential, as altered coupling of mitochondrial oxidative phosphorylation to mitochondrial ATP production, as altered mitochondrial respiration, or as an alteration (e.g., a statistically significant change relative to a control) in any other mitochondrial function or activity as provided herein and as known to the art.

By way of background, fluctuations in mitochondrial calcium are normal occurrences that are part of intracellular calcium homeostasis, as also noted above. Additionally, mitochondrial calcium levels may reflect transient low cytosolic calcium concentrations, which, in combination with reduced ATP or other conditions associated with mitochondrial pathology can yield mitochondrial permeability transition (MPT, see, e.g., Gunter et al., Biochim. Biophys. Acta 1366:5, 1998; Rottenberg et al., Biochim. Biophys. Acta 1016:87, 1990). Generally, under resting conditions the extramitochondrial (i.e., cytosolic) level of $Ca^{2+}$ is greater than that present within mitochondria. In the case of certain diseases or disorders, including diseases associated with altered mitochondrial function, mitochondrial or cytosolic calcium levels may vary from the above ranges and may range from, e.g., about 1 nM to about 500 mM, more typically from about 10 nM to about 100 $\mu$M and usually from about 20 nM to about 1 $\mu$M, where "about" indicates ±10%.

Because loss of membrane potential causes mitochondria to release sequestered $Ca^{2+}$ into the cytosol, the $Ca^{2+}$ load on nearby mitochondrial is increased, setting up a chain reaction (Darley-Usmar et al., Ann. Med. 23:583, 1991). Independent of the pathological sequelae of PT collapse, which include increased radical production from uncoupled electron transfer, the ensuing loss of ATP per se may be lethal to aerobically poised cells (Jurkowitz-Alexander et al., J. Neurochem. 59:344, 1992). In addition to a reduced metabolic energy supply, the lack of ATP may exacerbate $\Delta\Psi$m collapse.

MPT may also be induced by compounds that bind one or more mitochondrial molecular components. Such compounds include, but are not limited to, atractyloside and bongkrekic acid. Methods of determining appropriate amounts of such compounds to induce MPT are known in the art (see, e.g., Beutner el al., Biochim. Biophys. Acta 1368:7, 1998; Obatomi and Bach, Toxicol. Lett. 89:155, 1996; Green and Reed, Science 281:1309, 1998; Kroemer et al., Annu. Rev. Physiol. 60:619, 1998; and references cited therein).

Under certain conditions, a mitochondrial state which can feature altered mitochondrial regulation of intracellular calcium (e.g., altered mitochondrial membrane permeability to calcium) may be induced by exposing a biological sample to compositions referred to as "apoptogens" that induce programmed cell death, or "apoptosis". A variety of apoptogens are known to those familiar with the art (see, e.g, Green et al., Science 281:1309, 1998, and references cited therein) and may include by way of illustration and not limitation: tumor necrosis factor-alpha (TNF-α); Fas ligand; glutamate; N-methyl-D-aspartate (NMDA); interleukin-3 (IL-3); herbimycin A (Mancini et al., J. Cell. Biol. 138:449–469, 1997); paraquat (Costantini et al., Toxicology 99:1–2, 1995); ethylene glycols; protein kinase inhibitors, such as staurosporine, calphostin C, caffeic acid phenethyl ester, chelerythrine chloride, genistein; 1-(5-isoquinolinesulfonyl)-2-methylpiperazine; N-[2-((p-bromocinnamyl)amino)ethyl]-5-5-isoquinolinesulfonamide; KN-93; quercitin; d-erythro-sphingosine derivatives, for example, ceramide; UV irradiation; inophores such as ionomycin and valinomycin; MAP kinase inducers such as anisomycin, anandamine; cell cycle blockers such as aphidicolin, colcemid, 5-fluorouracil, homoharringtonine; acetylcholinesterase inhibitors such as berberine; antiestrogens such as, tamoxifen; pro-oxidants, such as tert-butyl peroxide, hydrogen peroxide; free radicals such as nitric oxide; inorganic metal ions, such as cadmium; DNA synthesis inhibitors, including, for example, actinomycin D and also including DNA topoisomerase inhibitors, for example, etoposide; DNA intercalators such as doxorubicin, bleomycin sulfate, hydroxyurea, methotrexate, mitomycin C, camptothecin, daunorubicin; protein synthesis inhibitors such as cycloheximide, puromycin, rapamycin; agents that affect microtubulin formation or stability, for example, vinblastine, vincristine, colchicine, 4-hydroxyphenylretinamide, paclitaxel; Bad protein, Bid protein and Bax protein (see, e.g., Jurgenmeier et al., Proc. Nat. Acad. Sci. USA 95:4997–5002, 1998, and references cited therein); calcium and inorganic phosphate (Kroemer et al., Ann. Rev. Physiol. 60:619, 1998).

As noted above, the invention thus pertains in part to detecting a signal generated by a calcium indicator molecule in a biological sample as provided herein. The calcium indicator molecule may be endogenous to (e.g., naturally occurring in) the sample or it may be exogenous, which includes at least one calcium indicator molecule that does not occur naturally in the biological sample but that has been loaded, administered, admixed, expressed (including expression as the product of a genetically engineered nucleic acid construct), targeted, contacted, exposed or otherwise artificially introduced into the sample, as long as the calcium indicator molecule is capable of generating a detectable signal that is proportional to the level of calcium in the cytosol or mitochondria. In preferred embodiment the calcium indicator molecule is exogenous and the detectable signal is a fluorescent signal.

It is therefore contemplated by the present invention to provide a method for assaying a cytosolic calcium level in a biological sample, in pertinent part, by contacting a biological sample comprising a cell containing cytosol, a mitochondrion and a calcium indicator molecule as provided herein, under conditions that permit maintenance of mitochondrial membrane potential, with a source of calcium cations, and detecting a signal generated by the calcium indicator molecule at a plurality of time points, for example, to generate a time-course of detected signal levels. Where the calcium indicator molecule is a fluorescent indicator, the signal generated by the indicator molecule, which signal is proportional to the level of calcium in the cytosol, may be detected by exposing the sample to light having an appropriate wavelength to excite the indicator, and determining resultant fluorescence with a suitable instrument for detecting a fluorescent light emission at an appropriate wavelength. Those having ordinary skill in the art can readily determine the manner by which the sample is contacted with the source of calcium cations based on the teachings provided herein, in view of the properties of the sample (including the calcium indicator molecules selected) and those of the source of calcium ions selected. As discussed in greater detail below, the method of the present invention may be used to identify an agent that alters mitochondrial function, that uncouples oxidative phosphorylation from ATP production, that is a respiratory inhibitor or that alters a mitochondrial calcium uniporter.

Thus, in preferred embodiments the calcium indicator molecule may be a light emission molecule, for example a fluorescent, phosphorescent, or chemiluminescent molecule or the like, which emits a detectable signal in the form of light when excited by excitation light of an appropriate wavelength. "Fluorescence" refers to luminescence (emission of light) that is caused by the absorption of radiation at one wavelength ("excitation"), followed by nearly immediate re-radiation ("emission"), usually at a different wavelength, that ceases almost at once when the incident radiation stops. At a molecular level, fluorescence occurs as certain compounds, known as fluorophores, are taken from a ground state to a higher state of excitation by light energy; as the molecules return to their ground state, they emit light, typically at a different wavelength. "Phosphorescence," in contrast, refers to luminescence that is caused by the absorption of radiation at one wavelength followed by a delayed re-radiation that occurs at a different wavelength and continues for a noticeable time after the incident radiation stops. "Chemiluminescence" refers to luminescence resulting from a chemical reaction, and "bioluminescence" refers to the emission of light from living organisms or cells, organelles or extracts derived therefrom.

A variety of calcium indicators are known in the art and are suitable for generating a detectable intracellular signal, for example, a signal that is proportional to the level of calcium in the cytosol or in the mitochondria, depending on a variety of factors pertaining to assay configuration, such as the particular biological sample and assay reagents that are selected. Suitable calcium indicators include but need not be limited to fluorescent indicators such as fura-2 (McCormack et al., 1989 Biochim. Biophys. Acta 973:420); mag-fura-2; BTC (U.S. Pat. No. 5,501,980); fluo-3, fluo-4, fluo-5F and fluo-5N (U.S. Pat. No. 5,049,673); fura-4F, fura-5F, fura-6F, and fura-FF; rhod-2, rhod-5F; Calcium Green™ 5N; benzothiaza-1 and benzothiaza-2; and others, which are available from Molecular Probes, Inc., Eugene, Oreg. (see also, e.g., Calcium Signaling Protocols—Meths. In Mol. Biol.—Vol. 114), Lambert, D. (ed.), Humana Press, 1999). In certain embodiments wherein calcium can be directly measured, a free calcium ion may itself act as a calcium indicator molecule. Such embodiments are directed to a detectable signal that is proportional to the level of calcium that is present, as determined, for example, using a calcium sensitive electrode (commercially available from, e.g., World Precision Instrument, Inc., Sarasota, Fla.) connected to an appropriate meter (e.g., a pH meter); preferably such direct calcium measurements are made when the biological sample comprises a permeabilized cell, a permeabilized cell depleted of cytosol, or one or more isolated mitochondria in a medium.

Calcium Green™ 5N is a particularly preferred calcium indicator molecule for use according to the present invention. Depending, however, on the particular assay conditions to be used, a person having ordinary skill in the art can select a suitable calcium indicator from those described above or from other calcium indicators, according to the teachings herein and based on known properties (e.g., solubility, stability, etc.) of such indicators. For example by way of illustration and not limitation, whether a cell permeant or cell impermeant indicator is needed (e.g., whether a sample comprises a permeabilized cell), affinity of the indicator for calcium (e.g., dynamic working range of calcium concentrations within a sample as provided herein) and/or fluorescence spectral properties such as a calcium-dependent fluorescence excitation shift, may all be factors in the selection of a suitable calcium indicator.

A variety of instruments can be used in methods of the invention to excite a calcium indicator molecule as provided herein that is a fluorescent compound, and to detect the signal generated by the calcium indicator molecule that is proportional to the level of calcium in the cytosol, e.g., to measure the resulting emission therefrom. Selection of a suitable instrument, light source, filter set, etc. may depend on factors known to those familiar with the art, such as (i) application of energy (i.e., light) at a wavelength that will excite the calcium indicator molecule, preferably at or near the optimum excitation wavelength of the indicator molecule ($\lambda max_{(ex)}$); (ii) detection of energy (i.e., light) within the emission spectrum of the acceptor compound, preferably at or near the optimum emission wavelength of the indicator molecule ($\lambda max_{(em)}$); (iii) the type of samples to be assayed; and (iv) the number and formatting of samples to be assayed in a given program, for example, a high throughput screening format.

With regard to factors (i) and (ii), the spectra of energy being applied to, and the spectra of energy being emitted by the samples will determine, in general, what type of instrument will be used. For example, although $\lambda(ex)$ should not be identical to $\lambda(em)$, the minimal acceptable amount of difference between these two values will be influenced by, among other factors, the instrumentation being used. That is, as $\lambda(ex)$ approaches $\lambda(em)$, instruments capable of resolving closely-spaced wavelengths are required, and an assay wherein the difference between $\lambda(ex)$ and $\lambda(em)$ is less than about 3 to about 5 nm requires a high resolution instrument. Conversely, an assay wherein the difference between $\lambda(ex)$ and $\lambda(em)$ is greater than about 50 to about 75 nm requires an instrument having relatively medium to low resolution.

Thus, with specific regard to factor (ii), the type of energy being emitted by an excited fluorophore and measured in samples will determine, in general, what type of instrument will be used. A fluorometer, for instance, is a device that measures fluorescent energy and should therefore be part of the instrumentation. A fluorometer may be anything from a relatively simple, manually operated instrument that accommodates only a few reaction vessels (e.g., sample tubes) at a time, to a somewhat more complex manually operated or robotic instrument that accommodates a larger number of samples in a format having a plurality of reaction vessels, such as a 96-well microplate (e.g., an fmax™ fluorimetric plate reader, Molecular Devices Corp., Sunnyvale, Calif.; or a Cytofluor™ fluorimetric plate reader, model #2350, Millipore Corp., Bedford, Mass.), or a complex robotic instrument (e.g., a FLIPR™ instrument; see infra) that accommodates a multitude of samples in a variety of formats such as 96-well microplates, 384-well microplates or other high throughput screening formats wherein, for example, detection of signals from a calcium indicator molecule in a plurality or reaction vessels may be automated.

With regard to factor (iii), the type of samples to be assayed in a given program, different formats will be appropriate for different types of samples. For example, 96-well or 384-well microplates may be suitable in instances where the cells of interest adhere to the microplate substrate, or to some material applied to the wells of the microplate (e.g., a natural or synthetic coating with which the wells have been treated, such as collagen, fibronectin, vitronectin, RGD peptide, poly-L-lysine, CelTak™, or the like). Interfering fluorescence derived from certain common plastic multiwell plate materials, however, may result in a large artifactual background component at excitation wavelengths below about 400 nm. Accordingly, for measurements involving nonadherent cells such as suspension cells, or suspensions of adherent cells that have been dislodged from a growth substrate, or suspension of adherent cells on microcarriers or the like, an instrument capable of reading fluorescent signals in glass or polymeric tubes or tubing, or another suitable non-interfering vessel, may be preferred. Regardless of what type of format is used, assay reaction vessels should allow for the introduction of biological samples, candidate agents, a source of calcium cations, control reagents and optionally additional compounds that may influence cytosolic calcium levels, as well as the ability to detect the signal generated by the calcium indicator molecule at a plurality of appropriate points in time.

Factor (iv), the number of samples to be assayed in a given program, may influence the degree of automation that can be implemented by the instrument selected. For example, when high throughput (HTS) screening, (i.e., assaying a large number of samples in a relatively brief time period) is desired, robotic or semi-robotic instruments are preferred. Alternatively, samples may be processed manually, even where formats that accommodate large sample numbers (e.g., 96-well microplates) are used.

As noted above, the present invention provides assays for use in identifying agents that alter mitochondrial regulation of intracellular calcium. Such assays are designed to detect an agent that alters mitochondrial function, a calcium uniporter inhibitor, a respiratory inhibitor and/or an uncoupler of oxidative phosphorylation from ATP production. The invention thus provides efficient methods of identifying agents, compounds or lead compounds for agents active at the level of a mitochondrial calcium regulatory function. Generally, these screening methods involve assaying for compounds which alter intracellular cytosolic free calcium levels under conditions that facilitate determination of mitochondrial involvement in regulating cytosolic calcium and, in preferred embodiments, such methods may be directed to determination of the involvement of a mitochondrial calcium uniporter. The methods are amenable to automated, cost-effective high throughput screening of chemical libraries for lead compounds.

The term "screening" refers to the use of the invention to identify agents, for instance, from among large collections of candidate agents, that alter mitochondrial regulation of intracellular calcium in a negative or positive fashion. Briefly, cells or portions thereof that comprise cytosol, one or more mitochondria and a calcium indicator molecule as provided herein are treated with a candidate agent under conditions that permit detection of intracellular calcium levels, including the use of pharmacologic inhibitors (or potentiators) or other assay reaction components having potentially relevant biological activities, to determine uptake or release of intracellular calcium by mitochondria. The effect of the candidate agent on detectable intracellular calcium levels is then monitored and compared to a control sample that has been treated identically except for omission of the candidate agent (e.g., with only the vehicle used to deliver the agent). Detection employs a calcium-sensitive reporter molecule (e.g., a calcium indicator molecule as provided herein) capable of generating a detectable signal that corresponds to the local calcium concentration.

It is contemplated that the present invention will be of major value in high throughput screening; i.e., in automated screening of a large number of candidate compounds for activity against one or more cell types. It has particular value, for example, in screening synthetic or natural product libraries for active compounds. The methods of the present invention are therefore amenable to automated, cost-effective high throughput drug screening and have immediate application in a broad range of pharmaceutical drug development programs. In a preferred embodiment of the invention, the compounds to be screened are organized in a high throughput screening format such as a 96-well plate format, or other regular two dimensional array, such as a 384-well, 48-well or 24-well plate format or an array of test tubes. For high throughput screening the format is therefore preferably amenable to automation. It is preferred, for example, that an automated apparatus for use according to high throughput screening embodiments of the present invention is under the control of a computer or other programmable controller. The controller can continuously monitor the results of each step of the process, and can automatically alter the testing paradigm in response to those results.

Depending on the assay, a Fluorometric Imaging Plate Reader (FLIPR™) instrument (Molecular Devices, Sunnyvale, Calif.) is often the instrument of choice for fluorescence-based assays of the invention. The FLIPR™ system (Molecular Devices, Sunnyvale, Calif.) has the following desirable features: (i) It uses a combination of a water-cooled, argon-ion laser illumination and cooled CCD camera as an integrating detector that accumulates detectable signal over the period of time in which it is exposed to the image and, as a result, its signal-to-noise characteristics are generally superior to those of conventional imaging optics; (ii) it also makes use of a proprietary cell-layer isolation optics that allow signal discrimination on a cell monolayer, thus reducing undesirable extracellular background fluorescence; (iii) it provides data in real-time, and can also provide kinetic data (i.e., readings at a plurality of timepoints); (iv) it has the ability to simultaneously excite fluorophores in, and read emissions from, all 96 wells of a 96-well microplate; (v) it provides for precise control of temperature and humidity of samples during analysis; (vi) it includes an integrated state-of-the-art 96-well pipettor, which uses dispensable tips to eliminate carryover between experiments, and that can be used to aspirate, dispense and mix precise volumes of fluids from microplates; and, (vii) in the case of the FLIPR[384] instrument, it can be adapted to run sample assays in a robotic or semi-robotic fashion, thus providing for rapid HTS analysis of large numbers of samples (e.g., up to about a hundred 96-well microplates per day).

As also described above, $Ca^{2+}$ influx into mitochondria appears to be largely dependent, and may be completely dependent, upon the negative transmembrane electrochemical potential ($\Delta\Psi$) established by electron transfer, and such influx fails to occur in the absence of $A\Delta\Psi$ even when an eight-fold $Ca^{2+}$ concentration gradient is imposed (Kapus et al., FEBS Lett. 282:61, 1991). In preferred embodiments of the invention, therefore, a biological sample as provided herein is contacted with a source of calcium cations under conditions that permit maintenance of mitochondrial membrane potential, as described in greater detail below. Accordingly, mitochondria may release $Ca^{2+}$ via the calcium uniporter described herein when the membrane potential is dissipated, as occurs, for example, with uncouplers of oxidative phosphorylation (i.e., uncouplers of the mitochondrial ETC from ATP production by ADP phosphorylation) such as 2,4-dinitrophenol (DNP) and carbonyl cyanide p-trifluoromethoxyphenylhydrazone (FCCP).

A compound that may be a source of calcium cations, according to certain embodiments of the invention, induces increased intracellular, cytoplasmic, cytosolic and/or mitochondrial concentrations of $Ca^{2+}$ by effecting a redistribution of calcium that is present in the extracellular milieu and/or that is present in one or more of the various intracellular compartments. Such compounds, including calcium ionophores, are well known to those having ordinary skill in the art. Also provided herein and known to the art are methods for measuring intracellular calcium (see, e.g., Gunter et al., J. Bioenerg. Biomembr. 26:471, 1994; Gunter et al., Biochim. Biophys. Acta 1366:5, 1998; McCormack et al., Biochim. Biophys. Acta 973:420, 1989; Orrenius et al., J. Neural. Transm. Suppl. 43:1, 1994; Leist et al., Rev. Physiol. Biochem. Pharmacol. 132:79, 1998; and Haugland, 1996, supra). Examples of useful calcium ionophores include A23187, ionomycin, CA 1001, enniatin B from Fusarium orthoceras var. enniatum (e.g., Levy et al., Biochem. Pharmacol. 50:2105, 1995), palytoxin from Palythoa toxica (e.g., Aizu et al., Japan. Jl. Pharmacol. 60:9, 1992), and in appropriate cell types, N-methyl-D-aspartic acid (NMDA) or other cell depolarization signals as known in the art (e.g., Brini et al., *Nature Medicine* 5:951, 1999) and described herein.

Accordingly, a person skilled in the art may readily select an appropriate procedure for detecting intracellular calcium and a suitable ionophore for use as a source of calcium cations in certain embodiments of the present invention, according to the instant disclosure and to well known methods, including the use of suitable calcium-containing buffers, media and similar reagents. In addition to ionophores, other compounds that induce increased intracellular (e.g., cytosolic) concentrations of $Ca^{2+}$ include but are not limited to the sesquiterpene lactone, thapsigargin, which is believed to inhibit sequestration of cytosolic free calcium in the endoplasmic reticulum (ER), possibly by inhibiting endoplasmic reticular $Ca^{2+}$-ATPase, without blocking calcium release by the ER into the cytosol (see, e.g., Takemura et al., *J. Biol. Chem.* 264:12266, 1989; Thastrup et al., *Agents Actions* 27:17, 1989; Won et al., *Endocrinol.* 136:5399, 1995; Begum et al., *J. Biol. Chem.* 268:3552, 1995; Low et al., *Eur. J. Pharmacol.* 250:53, 1993). Additional compounds capable of increasing or effecting the redistribution of intracellular calcium include carbachol (e.g., Jence et al., *J. Neurochem.* 64:1605, 1995; Yan et al., *Mol. Pharmacol.* 47:248, 1995), BHQ (2,5-Di-(t-butyl)-1,4-hydroquinone; e.g., Salvador et al., *Arch. Biochem. Biophys.* 351:272, 1998), CPA (cyclopiazonic acid, e.g., Badaoui et al., *J. Mol. Cell. Cardiol.* 27:2495, 1995) and, in the case of cells having appropriate receptors, amino acid neurotransmitters such as glutamate or NMDA.

As will therefore be appreciated by those familiar with the art, the particular cells that are exposed to a given compound (e.g., glutamate) reqaire a specific receptor therefor (e.g., glutamate receptor), in order for the compound to influence intracellular $Ca^{2+}$ levels. For example, NT-2 teratocarcinoma cells express glutamate receptors, whereas SH-SY5Y neuroblastoma cells do not. Thus, the choice of cell line in which it may be desirable to increase intracellular calcium levels will determine which compounds are most appropriate.

For example, by way of illustration and not limitation, in certain preferred embodiments of the invention related to determination of mitochondrial regulation of intracellular calcium, ionomycin (Toeplitz et al., *J. Amer. Chem. Soc.* 101:3344, 1979) may be used as a calcium ionophore that provides a source of calcium cations and Fura-2 or Rhod-2 (Haugland, 1996 *Handbook of Fluorescent Probes and Research Chemicals—Sixth Ed.*, Molecular Probes, Eugene, Oreg., pp. 266–274) may be a fluorescent calcium indicator molecule for detecting cytosolic or intramitochondrial calcium, respectively. In general, any combination of at least one suitable compound that provides a source of calcium cations (i.e., resulting in increased intracellular concentrations of $Ca^{2+}$) and at least one calcium indicator molecule (i.e., for detecting intracellular calcium levels) that permits measuring mitochondrial regulation of calcium homeostasis in a biological sample may be used. It is known in the art how to determine suitable concentrations of such compounds for the uses contemplated herein (see, e.g., Takei et al., *Brain Res.* 652:65, 1994; Hatanaka et al., *Biochem. Biophys. Res. Commun.* 227:513, 1996).

Additionally, pharmacologically active compounds that alter (e.g., increase or decrease) mitochondrial functions such as ETC activity (e.g., rotenone, oligomycin), or that alter intracellular distribution of $Ca^{2+}$ (e.g., thapsigargin), and with which those skilled in the art will be familiar, may be optionally employed to assess their effects on mitochondrial regulation of cytosolic calcium. According to non-limiting theory, such pharmacologically agents may be employed to functionally isolate calcium pools that are regulated by mitochondria, thereby permitting detection of a relationship between mitochondrial function and cytosolic calcium levels. For example, a suitable concentration of thapsigargin may be selected as disclosed herein and known in the art, such that calcium uptake by the endoplasmic reticulum is inhibited, thereby providing detection via the calcium indicator molecule of mitochondrial calcium loading from extramitochondrial (e.g., cytosolic) pools and/or mitochondrial release of calcium into the cytosol. Numerous variations in these and related methods and compositions, within the scope of the appended claims, will occur to those skilled in the art, in light of the present disclosure.

As used herein, mitochondria are comprised of "mitochondrial molecular components", which may be a protein, polypeptide, peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like; or another biological molecule that is a constituent of a mitochondrion. "Mitochondrial molecular components" includes but is not limited to "mitochondrial pore components". A "mitochondrial pore component" is any mitochondrial molecular component that regulates the selective permeability characteristic of mitochondrial membranes as described above, including those that bind calcium, transport calcium or are otherwise involved in the maintenance of calcium and/or other ion levels on either side of the mitochondrial membrane. Mitochondrial pore components also include mitochondrial molecular components responsible for establishing $\Delta\Psi m$ and those that are functionally altered during MPT.

Isolation and, optionally, identification and/or characterization of the mitochondrial pore component or components with which an agent that affects mitochondrial pore activity interacts may also be desirable and are within the scope of the invention. Once an agent is shown to alter a mitochondrial activity such as mitochondrial permeability properties, for example, mitochondrial binding, transport or regulation of calcium as provided herein and in U.S. application Ser. Nos. 09/161,172, 09/338,122 and 09/434,3564 or, for example, MPT according to the methods provided herein and in U.S. Ser. No. 09/161,172, those having ordinary skill in the art will be familiar with a variety of approaches that may be routinely employed to isolate the molecular species specifically recognized by such an agent and involved in regulation of MPT, where to "isolate" as used herein refers to separation of such molecular species from the natural biological environment.

Techniques for isolating a mitochondrial molecular component may include any biological and/or biochemical methods useful for separating the component from its biological source, and subsequent characterization may be performed according to standard biochemical and molecular biology procedures. Those familiar with the art will be able to select an appropriate method depending on the biological starting material and other factors. Such methods may include, but need not be limited to, radiolabeling or otherwise detectably labeling cellular and mitochondrial components in a biological sample, cell fractionation, density sedimentation, differential extraction, salt precipitation, ultrafiltration, gel filtration, ion-exchange chromatography, partition chromatography, hydrophobic chromatography, electrophoresis, affinity techniques or any other suitable separation method that can be adapted for use with the agent with which the mitochondrial pore component interacts. Antibodies to partially purified components may be developed according to methods known in the art and may be used to detect and/or to isolate such components.

A "biological sample comprising a cell containing cytosol, a mitochondrion and a calcium indicator molecule" may comprise any tissue or cell preparation in which cells are present that contain (i) cytosol, i.e., any or all intracellular but extraorganellar (e.g., extramitochondrial, extranuclear, etc.) material, which may include preferably intracellular sols, cell sap or other solutions, and which may also include exogenously derived materials that have been introduced into an intracellular but extraorganellar localization, for example, in the case of permeabilized cells, material that by virtue of the permeabilized state of the cells may come to occupy an intracellular site; (ii) a calcium indicator molecule as described herein, and (iii) intact mitochondria capable of maintaining a membrane potential when supplied with one or more oxidizable substrates, for example, glucose, malate, glutamate, pyruvate or galactose.

Mitochondrial membrane potential may be determined according to methods with which those skilled in the art will be readily familiar, including but not limited to detection and/or measurement of detectable compounds such as fluorescent indicators, optical probes and/or sensitive pH and ion-selective electrodes. (See, e.g., Bernardi et al., *Eur. J. Biochem.* 264:687, 1999; Bernardi, *Physiol. Rev.* 79:1127, 1999; Emster et al., *J. Cell Biol.* 91:227s, 1981, and references cited therein; see also Haugland, 1996 *Handbook of Fluorescent Probes and Research Chemicals—Sixth Ed.*, Molecular Probes, Eugene, Oreg., pp. 266–274 and 589–594.) By "capable of maintaining a potential" it is meant that such mitochondria have a membrane potential that is sufficient to permit the accumulation of a detectable, potential-sensitive or potentiometric compound, for example, the fluorescent dyes rhodamine 123, DASPMI [2-,4-dimethylaminostyryl-N-methylpyridinium], TMRM [tetramethyl rhodamine methyl ester] or other suitable compounds (see, e.g., Scheffler, *Mitochondria,* 1999 Wiley-Liss, NY, pp. 198–202; see also Haugland, 1996).

A biological sample comprising a cell containing cytosol and a mitochondrion may be derived from a subject or biological source as provided herein, and subsequently contacted with a calcium indicator molecule as described herein to provide a biological sample comprising a cell containing cytosol, a mitochondrion and a calcium indicator molecule. As described in greater detail below, the cell may in certain embodiments be a permeabilized cell, and in certain other embodiments may be a permeabilized cell depleted of cytosol.

According to certain other embodiments, and as described in greater detail below, a "biological sample comprising one or more isolated mitochondria and a calcium indicator molecule in a medium" (e.g., a respiratory medium) may be a liquid suspension containing mitochondria that are derived from a subject or biological source as provided herein. In preferred embodiments the isolated mitochondria may be prepared and subsequently contacted with a calcium indicator molecule to provide a biological sample comprising at least one isolated mitochondrion and a calcium indicator molecule in a medium or inside the mitochondrion, which in preferred embodiments refers to a liquid medium and may include, for example, any of a wide variety of aqueous biological buffers or liquid culture media. In certain other embodiments the calcium indicator molecule may be present in the isolated mitochondria at the time of isolation (e.g., recombinantly expressed, mitochondrially targeted aequorin). In either instance, the biological sample comprising one or more isolated mitochondria is preferably providing as a liquid suspension, according to these and related embodiments, such that intramitochondrial and/or extramitochondrial levels of calcium in the sample may be determined.

Thus, for example, a biological sample may be derived from a normal (i.e., healthy) individual or from an individual having a disease associated with altered mitochondrial function. Biological samples may be derived by obtaining a blood sample, biopsy specimen, tissue explant, organ culture or any other tissue or cell preparation from a subject or a biological source. The subject or biological source may be a biological organism such as a human or non-human animal, a prokaryote or a eukaryote, a plant, a unicellular organism or a multicellular organism. According to certain embodiments, the invention contemplates a biological sample comprising in pertinent part a calcium indicator molecule that is a polypeptide, cofactor, metabolite or the like which is present in the sample as a biosynthetic product, either naturally or as the result of genetic engineering, such that a suitable biological sample may be derived from a biological source without the need for a subsequent step of being contacted with an independently derived calcium indicator molecule.

The subject or biological source may also be a primary cell culture or culture adapted cell line including but not limited to genetically engineered cell lines that may contain chromosomally integrated or episomal recombinant nucleic acid sequences (including but not limited to a nucleic acid sequence encoding a polypeptide that may be a calcium indicator molecule as provided herein, for example, a green fluorescent protein (GFP), a FLASH protein or an aequorin-derived polypeptide or fusion protein as provided, for example, in U.S. Ser. No. 09/434,354 and references cited therein), immortalized or immortalizable cell lines, somatic cell hybrid or cytoplasmic hybrid "cybrid" cell lines (e.g., U.S. Pat. No. 5,888,498), differentiated or differentiatable cell lines, transformed cell lines and the like.

In certain embodiments, for example, a biological sample cell may be transfected with a gene encoding and expressing a biological receptor of interest, which may be a receptor having a known ligand (e.g., a cytokine, hormone or growth factor) or which may be an "orphaned" receptor for which no ligand is known. Further to such embodiments, one or more known ligands or other compounds suspected of being able to interact with the receptor of interest may be optionally included in the subject invention method, for example, a cytokine, hormone, growth factor, antibody, neurotransmitter, receptor activator, receptor inhibitor, ion channel modulator, ion pump modulator, irritant, drug, toxin or any other compound known to have, or suspected of having, a biologically relevant activity.

In certain other embodiments, a biological sample cell may express, may be induced to express or may be transfected with a gene encoding and expressing a calcium regulatory protein. Calcium regulatory proteins include any naturally occurring or artificially engineered polypeptide or protein that directly or indirectly alter (e.g., increase or decrease) intracellular or intraorganellar calcium levels. Examples of calcium regulatory proteins include calmodulin, calsequestrin, calpains I and II, calpastatin, calbindin-$D_{9k}$, osteocalcin, osteonectin, S-100 protein, troponin C and numerous transmembrane calcium channels.

Calcium regulatory proteins also include the mitochondrial calcium uniporter and the mitochondrial sodium-dependent and sodium-independent calcium transporters that mediate calcium efflux from mitochondria. Calcium uniporter function may play a role in a variety of normal metabolic processes, in apoptosis and in certain disease mechanisms. Although the mitochondrial calcium uniporter calcium transport activity has thus been characterized, including its activation by ADP, inhibition by ATP, $Mg^{2+}$, ruthenium red and its derivative Ru360 (Matlib et al., *J. Biol. Chem.* 273:10223, 1998; Emerson et al., *J. Amer. Chem. Soc.* 115:11799, 1993) and competitive inhibition by $Sr^{2+}$, $Mn^{2+}$ and $La^{3+}$, no specific polypeptide has been identified and confirmed as an authentic mitochondrial calcium uniporter, nor has a gene encoding such a uniporter been determined. A candidate uniporter polypeptide that, inter alia, localizes to mitochondria and is capable of calcium binding, calcium transport and/or other regulation of or by calcium is disclosed in U.S. application Ser. No. 09/427,867.

For example, some transmembrane calcium channels contain functional polypeptide domains related to intracellular binding, transport or regulation of free calcium, for instance, calcium-binding, EFHAND, ion transport, ligand channel and/or calmodulin-binding IQ-domains. EFHAND, Ion Channel, Ligand Channel and IQ. For information on ion transport, see, e.g.: Williams et al., *Science* 257:3898–395, 1992; Jan et al., *Cell* 69:715–718, 1992. For information on calcium binding/transport, see, e.g.: RyRs (ryanodine receptors) Chen et al., *J. Biol. Chem.* 273:14675–14678, 1998. For information on L-type $Ca^{2+}$ channels, see, e.g.: Hockerman et al., *Annu. Rev. Pharmcol. Toxicol.* 37:361–396, 1997. For information on ligand channels, see, e.g.: Tong, *Science* 267:1510–1512, 1995; regarding IQ, see, e.g., Xie et al., *Nature* 368:306–312, 1994. For information on EFHAND, see, e.g., Persechini et al., *Trends Neurosci.* 12:462, 1989; Ikura, *Trends Biochem. Sci.* 21:14, 1996; Guerini, *Biochem. Biophys. Res. Commun.* 235:271; Kakalis et al., *FEBS Lett.* 362:55, 1995. Thus, these or other calcium regulatory proteins may be expressed in a cell present in a biological sample as provided herein.

Accordingly, cells for use according to the present invention may be provided as freshly prepared cells derived from a subject or biological source or as cultured cells, and in certain preferred embodiments the cells are cultured cells. As provided herein and known in the art, cultured cells may be adherent cells that naturally adhere to a solid substrate, or may be non-adherent cells that may further be maintained as cells in a suspension of freely growing cells by cultivation in an appropriate cell culture system. In certain preferred embodiments of the present invention, the biological sample comprises a cell that is a suspension cell. In other preferred embodiments, populations of naturally adherent cells, which may require attachment to a solid substrate for growth, are expanded as adherent cells in suitable culture flasks and subsequently detached from the flask wall with an appropriate detaching reagent, for use in the assays described herein. In another preferred embodiment of the invention, the naturally adherent cells are grown on suspension microcarriers, for example, microspherical beads to which the cells adhere during the growth, or another appropriate cell cultivating system that permits maintenance and/or assay of adherent cells in a suspension. Microcarriers and other products for handling adherent cells as cell suspensions are known to those familiar with the art and are commercially available from a variety of sources.

According to certain embodiments contemplated by the present invention, a cell may be a permeabilized cell, which includes a cell that has been treated in a manner that results in loss of plasma membrane selective permeability. For example, it may be desirable to permeabilize a cell in a manner that permits calcium cations in the extracellular milieu to diffuse into the cell, as an alternative to the use of a calcium ionophore. As another example, certain calcium indicator molecules as provided herein may not be readily permeable through the plasma membrane, such that they may efficiently gain entry to the cytosol only following permeabilization of the cell. As yet another example, certain candidate agents being tested according to the method of the present invention may not be able to pass through the plasma membrane, such that a permeabilized cell provides a suitable test cell for the potential effects of such agent. Those having ordinary skill in the art are familiar with methods for permeabilizing cells, for example by way of illustration and not limitation, through the use of surfactants, detergents, phospholipids, phospholipid binding proteins, enzymes, viral membrane fusion proteins and the like; through the use of osmotically active agents; by using chemical crosslinking agents; by physicochemical methods including electroporation and the like, or by other permeabilizing methodologies.

Thus, for instance, cells may be permeabilized using any of a variety of known techniques, such as exposure to one or more detergents (e.g., digitonin, Triton X-100™, NP-40™, octyl glucoside and the like) at concentrations below those used to lyse cells and solubilize membranes (i.e., below the critical micelle concentration). Certain common transfection reagents, such as DOTAP, may also be used. ATP can also be used to permeabilize intact cells, as may be low concentrations of chemicals commonly used as fixatives (e.g., formaldehyde). Accordingly, in certain embodiments of the invention, it may be preferred to use intact cells and in certain other embodiments the use of permeabilized cells may be preferred.

According to certain embodiments of the present invention there are provided methods for identifying an agent that alters mitochondrial function, for identifying an agent that uncouples oxidative phosphorylation from ATP production, for identifying a respiratory inhibitor and for identifying a compound that alters a mitochondrial calcium uniporter, each of said methods comprising in pertinent part the use of a sample comprising a mitochondrion contained within a cell that is permeabilized and that is depleted of cytosol. Determination of when a cell is depleted of cytosol may be accomplished by any of a variety of methods well known in the art, for example, those described in Fiskum et al. (1980 *Proc. Nat. Acad. Sci. USA* 77:3430–3434), including quantitative methods for monitoring the degree of cytosolic depletion by determining any of a number of known cytosolic markers, for example, the enzyme lactate dehydrogenase (LDH), or by monitoring the effects of the depletion method on cellular architecture. Preferably, a cell depleted of cytosol is essentially completely depleted of cytosol, which refers to depletion of cytosol that results in there being no remaining detectable cytosolic marker associated with the cell, according to criteria such as those described Fiskum et al. (1980). In other embodiments, a cell that is depleted of cytosol may be substantially depleted of cytosol, which may include a cell from which greater than 40 percent, preferably greater than 60 percent, and more preferably greater than 75 percent of at least one detectable cytosolic marker (e.g., LDH) is no longer associated with the cell using criteria known to the art, relative to control cells from which cytosol has not been depleted.

Accordingly, it will be appreciated that the invention also contemplates compositions and methods for detecting agents that alter (e.g., increase or decrease in a statistically significant manner) mitochondrial function, that alter a mitochondrial calcium uniporter, that uncouple oxidative phosphorylation from ATP production or that inhibit respiration, and for detecting compounds that alter the activity of such agents, which methods may relate to reintroducing to a sample comprising a mitochondrion (e.g., a cytosol depleted cell as provided herein, or an isolated mitochondrion) one or more cytosolic molecular components. Without wishing to be bound by theory, differences in the results obtained when cytosol is present and when cytosol has been depleted as observed in assays for mitochondrial function as described herein, may be attributable to the presence or activity of one or more cytosolic molecular components. Such cytosolic components may include, for example, ATP or other biolochemical molecules such as metabolites, catabolites, intermediates, cofactors, substrates, catalysts and the like. Such cytosolic components may also include, for example, one or more of a protein, peptide, glycopeptide or glycoprotein, nucleic acid or polynucleotide (including, for example, DNA or RNA), lipid including a glycolipid, proteolipid or phospholipid, or a carbohydrate, or any combination of such species, that may be present in cytosol. Isolation of cytosolic molecular components may be achieved according to any of a number of well known biochemical and chemical separation strategies known to the art, including but not limited to radiolabeling or otherwise detectably tagging cytosolic components in a biological sample, or to cell fractionation, density sedimentation, differential extraction, salt precipitation, ultrafiltration, gel filtration, ion-exchange chromatography, partition chromatography, hydrophobic chromatography, electrophoresis, affinity techniques or any other suitable separation method. Antibodies to partially purified components may be developed according to methods known in the art and may be used to detect and/or to isolate such components.

Affinity techniques may be particularly useful in the context of the present invention, and may include any method that exploits a specific binding interaction between a cytosolic component and an agent identified according to the invention that interacts with the cytosolic component. For example, because agents that influence mitochondrial function (or that uncouple oxidative phosphorylation from ATP production, or that alter a mitochondrial calcium uniporter, or that inhibit respiration) can be immobilized on solid phase matrices, an affinity binding technique for isolation of the cytosolic component(s) may be particularly useful. Alternatively, affinity labeling methods for biological molecules, in which such a mitochondrial functionally-active agent may be modified with a reactive moiety, are well known and can be readily adapted to the interaction between the agent and a cytosolic component, for purposes of introducing into the cytosolic component a detectable and/or recoverable labeling moiety. (See, e.g., *Pierce Catalog and Handbook,* 1994 Pierce Chemical Company, Rockford, Ill.; Scopes, R.K., *Protein Purification: Principles and Practice,* 1987, Springer-Verlag, New York; and Hermanson, G. T. et al., *Immobilized Affinity Ligand Techniques,* 1992, Academic Press, Inc., Calif.; for details regarding techniques for isolating and characterizing biological molecules, including affinity techniques.

Characterization of cytosolic component molecular species, isolated by affinity techniques described above or by other biochemical methods, may be accomplished using physicochemical properties of the cytosolic component such as spectrometric absorbance, molecular size and/or charge, solubility, peptide mapping, sequence analysis and the like. (See, e.g., Scopes, supra.) Additional separation steps for biomolecules may be optionally employed to further separate and identify molecular species that co-purify with such cytosolic components that influence mitochdondrial or related functions such as those described herein. These are well known in the art and may include any separation methodology for the isolation of proteins, lipids, nucleic acids, carbohydrates, or other biological molecules of interest, typically based on physicochemical properties of the newly identified components of the complex. Examples of such methods include RP-HPLC, ion exchange chromatography, hydrophobic interaction chromatography, hydroxyapatite chromatography, native and/or denaturing one- and two-dimensional electrophoresis, ultrafiltration, capillary electrophoresis, substrate affinity chromatography, immunoaffinity chromatography, partition chromatography or any other useful separation method.

For example, sufficient amounts of a cytosolic protein may be obtained for partial structural characterization by microsequencing. Using the sequence data so generated, any of a variety of well known suitable strategies for further characterizing the cytosolic components may be employed. For example, nucleic acid probes may be synthesized for screening one or more appropriately chosen cDNA libraries to detect, isolate and characterize a cDNA encoding such component(s). Other examples may include use of the partial sequence data in additional screening contexts that are well known in the art for obtaining additional amino acid and/or nucleotide sequence information. See, e.g., *Molecular Cloning: A Laboratory Manual, Third Edition*, edited by Sambrook, Fritsch & Maniatis, Cold Spring Harbor Laboratory, 1989. Such approaches may further include nucleic acid library screening based on expression of library sequences as polypeptides, such as binding of such polypeptides to mitochondria-active agents identified according to the present invention; or phage display screening approaches or dihybrid screening systems based on protein—protein interactions with known mitochondrial proteins, and the like, any of which may be adapted to screening for mitochondrially active cytosolic components provided by the present invention, using routine methodologies with which those having ordinary skill in the art will be familiar. (See, e.g., Bartel et al., In *Cellular Interactions in Development: A Practical Approach*, Ed. D. A. Harley, 1993 Oxford University Press, Oxford, United Kingdom, pp. 153–179, and references cited therein.) Preferably extracts of cultured cells, and in particularly preferred embodiments extracts of biological tissues or organs may be sources of novel mitochondrially active cytosolic proteins or other cytosolic factors. Preferred sources may include blood, brain, fibroblasts, myoblasts, liver cells or other cell types.

Briefly, for example, and based essentially on Fiskum et al. (1980 *Proc. Nat. Acad. Sci. USA* 77:3430–3434), for permeabilized assay cells in which cytosol is to be retained, aliquots of cell suspensions containing approximately $30 \times 10^6$ cells may be pelleted by centrifugation at 16,000×g for two minutes at room temperature, resuspended in basal incubation medium (125 mM KCl, 20 mM HEPES-KOH, pH7.0, 2 mM $K_2HPO_4$) and pelleted again. The intact cell pellet is transferred into a suitable reaction vessel and assayed at 20° C. in a respiratory medium such as a basal incubation medium containing either (i) 5 mM glutamate and 5 mM malate, or (ii) 5 mM succinate and 2 $\mu$M rotenone, as respiratory substrates.

For assay cells in which cytosol is to be depleted, cells are pelleted, resuspended and pelleted again as described above, then resuspended in basal incubation medium containing respiratory substrates and digitonin (e.g., 150 mM sucrose, 50 mM KCl, 20 mM Hepes, 2 mM $K_2HPO_4$, pH 7.0 containing 5 mM glutamate, 5 mM malate, 0.03% digitonin, 4 mM $MgCl_2$, 1 mM EGTA, 3.0 mM ATP). The cell suspension is incubated for 20 minutes at room temperature while being stirred in a disposable spectrophotometer cuvette to keep the cells in suspension. After the incubation period, cytosol is separated as the supernatant, following centrifugation at 20,800×g in a refrigerated microfuge for 10 minutes at 4° C., from the pellet (which comprises cytosol-depleted cells and contains mitochondria, other organelles and plasma membrane). The cytosol-depleted, digitonin permeabilized cells are resuspended again in basal medium, pelleted by centrifugation, and the supernatant fluid is removed. The pellet containing all cellular organelles (Fiskum et al., 1980) is transferred to a suitable reaction vessel and assayed in digitonin-free incubation medium with respiratory substrates (e.g., glutamate/malate).

A candidate agent for use according to the present invention may be any composition of matter that is suspected of altering mitochondrial function as provided herein, in a manner that detectably alters a signal generated by a calcium indicator molecule in a cell-based assay as described herein. Detectable alteration of a signal generated by a calcium indicator molecule typically refers to a statistically significant alteration (e.g., increase or decrease) of the signal detected at at least one of a plurality of time points. According to the present invention, a candidate agent that is identified as an agent that alters mitochondrial function as provided herein cannot be any of the following compounds, although such compounds may be present in any of the present screening assays: rotenone, oligomycin, succinate, Bcl-2, or cyclosporin A.

Preferably the candidate agent is provided in soluble form. Without wishing to be bound by theory, a candidate agent may directly alter the activity of a mitochondrial molecular component that regulates cytosolic free calcium levels, such as a calcium channel or uniporter (e.g., by physical contact with the calcium channel), or may do so indirectly (e.g., by interaction with one or more additional molecular components such as mitochondrial molecular components present in a sample, where such additional components alter mitochondrial calcium regulatory activity in response to contact with the agent). Typically, and in preferred embodiments such as for high throughput screening, candidate agents are provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons.

For example, members of a library of test compounds can be administered to a plurality of samples in each of a plurality of reaction vessels in a high throughput screening array as provided herein, each containing at least one cell containing cytosol, a mitochondrion and a calcium indicator molecule under conditions as provided herein. The samples are contacted with a source of calcium cations and then assayed for a detectable signal generated by the calcium indicator molecule at a plurality of time points, and the signal generated from each sample in the presence of the candidate agent is compared to the signal generated in the absence of the agent. Compounds so identified as capable of influencing mitochondrial function (e.g., alteration of calcium uniporter activity) are valuable for therapeutic and/or diagnostic purposes, since they permit treatment and/or detection of diseases associated with altered mitochondrial function. Such compounds are also valuable in research directed to molecular signaling mechanisms that involve a mitochondrial calcium uniporter, and to refinements in the discovery and development of future uniporter-specific compounds exhibiting greater specificity.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694 and PCT/US91/04666) or other compositions that may include small molecules as provided herein (see e.g., PCT/US94/08542, EP 0774464, U.S. Pat. No. 5,798,035, U.S. Pat. No. 5,789,172, U.S. Pat. No. 5,751,629). Those having ordinary skill in the art will appreciate that a diverse assortment of such libraries may be prepared according to established procedures, and tested using a biological sample according to the present disclosure.

An agent so identified as one that alters (e.g., increases or decreases) mitochondrial function is preferably part of a pharmaceutical composition when used in the methods of the present invention. The pharmaceutical composition will include at least one of a pharmaceutically acceptable carrier, diluent or excipient, in addition to one or more selected agent that alters mitochondrial function and, optionally, other components.

Therapeutic Applications

Agents identified using the above assays may have remedial, therapeutic, palliative, rehabilitative, preventative and/or prophylactic effects on patients suffering from, or potentially predisposed to developing, diseases and disorders associated with alterations in mitochondrial function. Such diseases may be characterized by abnormal, supernormal, inefficient, ineffective or deleterious calcium regulatory activity, for example, defects in uptake, release, activity, sequestration, transport, metabolism, catabolism, synthesis, storage or processing of calcium and/or directly or indirectly calcium-dependent biological molecules and macromolecules such as proteins and peptides and their derivatives, carbohydrates and oligosaccharides and their derivatives including glycoconjugates such as glycoproteins and glycolipids, lipids, nucleic acids and cofactors including ions, mediators, precursors, catabolites and the like.

Such diseases and disorders include, by way of example and not limitation, chronic neurodegenerative disorders such as Alzheimer's disease (AD) and Parkinson's disease (PD); auto-immune diseases; diabetes mellitus, including Type I and Type II; mitochondria associated diseases, including but not limited to congenital muscular dystrophy with mitochondrial structural abnormalities, fatal infantile myopathy with severe mtDNA depletion and benign "later-onset" myopathy with moderate reduction in mtDNA, MELAS (mitochondrial encephalopathy, lactic acidosis, and stroke) and MIDD (mitochondrial diabetes and deafness); MERFF (myoclonic epilepsy ragged red fiber syndrome); arthritis; NARP (Neuropathy; Ataxia; Retinitis Pigmentosa); MNGIE (Myopathy and external ophthalmoplegia; Neuropathy; Gastro-Intestinal; Encephalopathy), LHON (Leber's Hereditary Optic Neuropathy), Kearns-Sayre disease; Pearson's Syndrome; PEO (Progressive External Ophthalmoplegia); Wolfram syndrome; DIDMOAD (Diabetes Insipidus, Diabetes Mellitus, Optic Atrophy, Deafness); Leigh's Syndrome; dystonia; schizophrenia; and hyperproliferative disorders, such as cancer, tumors and psoriasis.

In contrast to chronic neurodegenerative diseases, neuronal death following stroke occurs in an acute manner. A vast amount of literature now documents the importance of mitochondrial function in neuronal death following ischemia/reperfusion injury that accompanies stroke, cardiac arrest and traumatic injury to the brain. Experimental support continues to accumulate for a central role of defective energy metabolism, alteration in mitochondrial function leading to increased oxygen radical production and impaired intracellular calcium homeostasis, and active mitochondrial participation in the apoptotic cascade in the pathogenesis of acute neurodegeneration.

A stroke occurs when a region of the brain loses perfusion and neurons die acutely or in a delayed manner as a result of this sudden ischemic event. Upon cessation of the blood supply to the brain, tissue ATP concentration drops to negligible levels within minutes. At the core of the infarct, lack of mitochondrial ATP production causes loss of ionic homeostasis, leading to osmotic cell lysis and necrotic death. A number of secondary changes can also contribute to cell death following the drop in mitochondrial ATP. Cell death in acute neuronal injury radiates from the center of an infarct where neurons die primarily by necrosis to the penumbra where neurons undergo apoptosis to the periphery where the tissue is still undamaged (Martin et al., *Brain Res. Bull.* 46:281–309, 1998).

Much of the injury to neurons in the penumbra is caused by excitotoxicity induced by glutamate released during cell lysis at the infarct focus, especially when exacerbated by bioenergetic failure of the mitochondria from oxygen deprivation (MacManus and Linnik, *J. Cerebral Blood Flow Metab.* 17:815–832, 1997). The initial trigger in excitotoxicity is the massive influx of $Ca^{2+}$ primarily through the NMDA receptors, resulting in increased uptake of $Ca^{2+}$ into the mitochondria (reviewed by Dykens, "Free radicals and mitochondrial dysfunction in excitotoxicity and neurodegenerative diseases" in *Cell Death and Diseases of the Nervous System*, V. E. Koliatos and R.R. Ratan, eds., Humana Press, New Jersey, pages 45–68, 1999). The $Ca^{2+}$ overload collapses the mitochondrial membrane potential ($\Delta\Psi m$) and induces increased production of reactive oxygen species (Dykens, *J. Neurochem.* 63:584–591, 1994; Dykens, "Mitochondrial radical production and mechanisms of oxidative excitotoxicity" in *The Oxygen Paradox*, K. J. A. Davies, and F. Ursini, eds., Cleup Press, U. of Padova, pages 453–467, 1995). If severe enough, $\Delta\Psi_m$ collapse and mitochondrial $Ca^{2+}$ sequestration can induce MPT, indirectly releasing cytochrome c and other proteins that initiate apoptosis (Bernardi et al., *J. Biol Chem* 267:2934–2939, 1994; Zoratti et al., *Biochim Biophys Acta* 1241:139–176, 1995; Ellerby et al., *J. Neurosci* 17:6165–6178, 1997). Consistent with these observations, glutamate-induced excitotoxicity can be inhibited by preventing mitochondrial $Ca^{2+}$ uptake or blocking MPT (Budd et al., *J. Neurochem* 66:403–411, 1996; White et al., *J. Neurosci* 16:5688–5697, 1996; Li et al., *Brain Res* 753:133–140, 1997; Stout et al., *Nat. Neurosci.* 1:366–373, 1998).

Agents and methods that maintain mitochondrial integrity during ischemia/reperfusion, traumatic tissue injury and/or seizures would be expected to be novel protective agents with utility in limiting any ischemia/reperfusion injury to bodily tissues. Given the limited therapeutic window for blockade of necrotic death at the core of an infarct, it may be particularly desirable to develop therapeutic strategies to limit neuronal death by preventing mitochondrial dysfunction in the non-necrotic regions of an infarct. As provided herein, such agents may be identified by screening collections of compounds for their ability to alter (e.g., increase or decrease) mitochondrial regulation of cytosolic calcium under excitotoxic conditions that mimic transient ischemia. Without wishing to be bound by theory, preferred agents for stroke may be those that lower or reduce mitochondrial calcium uptake. Such agents are expected to have remedial, therapeutic, palliative, rehabilitative, preventative, prophylactic or disease-impeditive effects on patients who have had, or who are thought to be predisposed to have, strokes. The cytosolic calcium-based assay of the present invention can also be used to estimate which agent(s) are most likely to be effective for a given individual, in that a patient having mitochondria that exhibit altered calcium regulation is expected to be more likely to respond to agents that modulate mitochondrial regulation of calcium than a patient having mitochondria with a normal calcium regulatory profile.

Conversely, in certain other disease indication areas, a desired property of an agent that alters mitochondrial function with respect to calcium regulatory activity may be promotion of calcium uptake or retention by mitochondria. For example, in certain types of cancer, or in certain cells that are transformed with genes known to be overexpressed in cancer cells, elevated cytosolic calcium levels may have deleterious effects that would be potentially overcome by sequestration of excess calcium in mitochondria. Accordingly, identification of agents according to the present invention that up-regulate mitochondrial uptake may therefore provide beneficial therapeutic agents. Similarly, in any number of other disease models, cell systems or other biological contexts, for example, in systems wherein cells are identified that are particularly sensitive to stresses from inappropriate calcium management (or that can be made so, for instance, by altering the expression of apoptosis pathway components such as Bcl-2, by exposure to apoptogens or by exposure to agents that alter intracellular calcium distribution), the present invention offers opportunities to identify agents that alter aberrant calcium regulation by altering mitochondrial function.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The pharmaceutical compositions that contain one or more agents that alter mitochondrial function as provided herein may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more agents that alter mitochondrial function, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of an agent that alters mitochondrial function as provided herein such that a suitable dosage will be obtained. Typically, this amount is at least 0.01 wt % of the agent in the composition. When intended for oral administration, this amount may be varied to be between 0.1 and about 70% of the weight of the composition. Preferred oral compositions contain between about 4% and about 50% of the agent(s) that alter mitochondrial function. Preferred compositions and preparations are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the agent that alters mitochondrial function of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. In the methods of the invention, the agent(s) that alter mitochondrial function identified as described herein may be administered through use of insert(s), bead(s), timed-release formulation(s), patch(es) or fast-release formulation(s).

It will be evident to those of ordinary skill in the art that the optimal dosage of the agent(s) that alter mitochondrial function may depend on the weight and physical condition of the patient; on the severity and longevity of the physical condition being treated; on the particular form of the active ingredient, the manner of administration and the composition employed. It is to be understood that use of an agent that alters mitochondrial function as disclosed herein in a chemotherapeutic composition can involve such an agent being bound to another compound, for example, a monoclonal or polyclonal antibody, a protein or a liposome, which assist the delivery of said agent.

Species-Specific Agents

In certain embodiments, the present invention provides screening assays for identifying species-specific agents. A "species-specific agent" refers to an agent that affects mitochondrial calcium regulation in one source (e.g., species) but that does not substantially affect the mitochondrial calcium regulation in a second source. In other words, the agent should have an effect on one species that is at least twice the effect on the other species. The screening assays provided herein may be used to identify such agents, using cells and/or mitochondria obtained from different biological sources.

This embodiment of the invention may be used, for example, to identify agents that selectively induce mitochondrial calcium-mediated apoptosis in different species, e.g., in trypanosomes (Ashkenazi et al., *Science* 281:1305–1308, 1998), and other eukaryotic pathogens and parasites, including but not limited to insects, but which do not induce apoptosis in the cells of their mammalian hosts. Such agents are expected to be useful for the prophylactic or therapeutic management of such pathogens and parasites. For example, Ridgley et al. (*Biochem. J.* 340:33–40, 1999) describe a $Ca^{2+}$-dependent cell death process in the unicellular organism *Trypanosoma brucei brucei*, a parasite of wild game animals in Africa that is related to the causative agents of "sleeping sickness" in humans. Following ROS (reactive oxygen species) production, mitochondrial $Ca^{2+}$ transport was impaired and the $Ca^{2+}$ barrier between the nuclear envelope and the cytosol was disrupted. As a consequence, mitochondria were unable to act as "$Ca^{2+}$ reservoirs" and $Ca^{2+}$ accumulated in the nucleus, where extensive DNA fragmentation took place. Trypanosomes expressing murine Bcl-2 were not protected from ROS (even though Bcl-2-mediated protection from ROS and mitochondrial dysfunction have been reported for mammalian cells).

The parasitic haemoflagellate *T. brucei brucei* thus seems to have, like metazoans, a $Ca^{2+}$-dependent cell death pathway which nonetheless has differences (e.g., in terms of its biochemistry) from metazoan $Ca^{2+}$-dependent cell death pathways. One goal of the present invention is to exploit such differences to find, using the screening assays of the disclosure, compounds that have an antibiotic effect because they induce the Trypanosomal, but not the mammalian, $Ca^{2+}$-dependent cell death pathway.

By way of another example, members of the phylum Apicomplexa (formerly called Sporozoa) comprise a large and diverse group of pathogenic protozoa that are intracellular parasites. Some members, including species of Babesia, Theileria and Eimeria, cause economically important animal diseases, and other members, such as *Toxoplasma gondii* and Cryptosporidium spp. also cause human disease, particularly in immunocompromised individuals. The acomplexicans are unusual in terms of their extrachromosomal DNA elements, as they comprise both a mitochondrial genome and a putative plastid genome (see Feagin, *Annu. Rev. Microbiol.* 48:81–104, 1994, for a review). Probably the most well-studied acomplexicans are species of Plasmodium, which cause malaria. Antimalarial agents include agents that specifically impact the function of Plasmodium mitochondria (Peters et al., *Ann. Trop. Med. Parsitol.* 78:567–579, 1984; Basco et al., *J. Eukaryot. Microbiol.* 41:179–183, 1994), and one such agent, atovaquone, collapses $\Delta\psi$ in mitochondria from *Plasmodium yoelii* but has no effect on $\Delta\psi$ of mammalian mitochondria (Srivastava et al., *J. Biol. Chem.* 272:3961–3966, 1997). Accordingly, the assays provided herein can be used to screen libraries of compounds for novel antimalarial agents, such as compounds that cause $\Delta\psi$ collapse in Plasmodium mitochondria but not in mammalian mitochondria.

As another example, screening methods provided herein may be used to identify agents that selectively induce $\Delta\psi$ collapse in mitochondria derived from undesirable plants (e.g., weeds) but not in desirable plants (e.g., crops), or in undesirable insects (in particular, members of the family Lepidoptera and other crop-damaging insects) but not in desirable insects (e.g., bees) or desirable plants. Such agents are expected to be useful for the management and control of such undesirable plants and insects. Cultured insect cells, including for example, the Sf9 and Sf21 cell lines derived from *Spodoptera frugiperda*, and the HIGH FIVE™ cell line from *Trichopolusia ni* (these three cell lines are available from Invitrogen, Carlsbad, Calif.) may be the source of mitochondria in certain such embodiments of the invention.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following Examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLES

As noted above, a variety of different types of samples containing mitochondria, or derivatives thereof such as submitochondrial particles (SMPs), can be used in the methods of the assay. Whole (nonpermeabealized) cells can be used, but have potential drawbacks relative to permeabilized cells as explained below.

A permeabilized cell is a cell that has been treated in a manner that results in a partial or complete loss of plasma membrane selective permeability. As a first example, it may be desirable to permeabilize a cell in a manner that permits calcium cations in the extracellular milieu to diffuse into permeabilized cells and contact mitochondria. Thus, in this instance, permeabilization serves as an alternative to the use of a calcium ionophore. As a second example, certain detectable molecules, such as calcium indicator molecules capable of generating a detectable signal as provided herein, may penetrate the plasma membrane at a moderate rate, or to a limited degree, unless their entry into the cytosol is facilitated in some manner. Permeabilization of cells is one manner by which the cytosolic entry of such detectable molecules can be facilitated. As a third example, some candidate agents being tested according to the method may penetrate the plasma membrane at a moderate rate, or to a limited degree, unless their entry into the cytosol is facilitated in some manner. Permeabilization of cells is one manner by which the entry of such candidate agents into the cytosolic space can be facilitated. Active agents that are identified under these conditions can subsequently be chemically modified to enhance their uptake by whole cells; active agents that are so modified are expected to serve as lead compounds for drug development and, in some instances, may themselves be used as drugs or as drug candidates.

As also described above, those having ordinary skill in the art are familiar with methods for permeabilizing cells, for example by way of illustration and not limitation, through the use of surfactants, detergents, phospholipids, phospholipid binding proteins, enzymes, viral membrane fusion proteins and the like; by exposure to certain bacterial toxins, such as ($\alpha$-hemolysin); by contact with hemolysins such as saponin (which is also a nonionic detergent, as is digitonin); through the use of osmotically active agents; by using chemical crosslinking agents; by physicochemical methods including electroporation and the like, or by other permeabilizing methodologies including, e.g., physical manipulations such as electroporation. Determination of the most appropriate permeabilizing agent in a particular context may be based on factors including toxicity of the agent to a specific chosen cell line, the molecular size of the agent that it is desired to have enter cells, and the like (see, e.g., Schulz, *Methods Enzymol.* 192:280–300, 1990).

Thus, cells may be permeabilized using any of a variety of known techniques, for instance, by the addition of permeabilizing agents such as the bacterial toxins streptolysin O or *Staphylococcus aureus* $\alpha$-toxin (a.k.a. $\alpha$-hemolysin); other hemolytic agents such as saponin; or exposure to one or more detergents (e.g., digitonin, Triton X-100, NP-40, n-Octyl $\beta$-D-glucoside and the like) at concentrations below those used to lyse cells and solubilize membranes (i.e., below the critical micelle concentration). Certain common transfection reagents, such as DOTAP, may also be used. ATP can also be used to permeabilize intact cells, as may be low concentrations of chemicals commonly used as fixatives (e.g., formaldehyde). All of the permeabilizing agents described in this paragraph are available from, e.g., Sigma Chemical Co., St. Louis, Mo. (see Sigma catalog entitled "Biochemicals and Reagents for Life Science Research," Anon., 1999, and references cited therein for these and other permeabilizing agents).

Permeabilized cells can be assayed for uniporter activity in the presence and/or absence of compounds of interest (e.g., candidate agents that alter mitochondrial functions, including uncouplers of oxidative phosphorylation from ATP production, respiratory inhibitors, or agents that alter mitochondrial calcium uniporter activity). A calcium-sensitive detectable reagent, which may be a fluorophore, is present in the media, and conditions are established in which the reagent is free to diffuse into the cytosolic space of permeabilized cells but does not enter one or more subcellular calcium reservoirs such as, for example, organelles such as the endoplasmic reticulum (ER) or mitochondria. $Ca^{2+}$ ions also freely enter permeabilized cells; however, in one embodiment of the invention, due to the presence of one or more intracellular $Ca^{2+}$ modulating agents (ICMAs), $Ca^{2+}$ ions do not enter and/or are released from certain intracellular calcium reservoirs such as, for example, the ER or mitochondria.

Isolated (i.e., physically separated from the cellular environment in which they are naturally present or biosynthesized) or semi-purified mitochondria, or submitochondrial particles, may also be used in the assays of the invention. Methods of purifying mitochondria from a variety of species, cells, tissues and organs are known in the art (see, for example, Glick et al., *Methods in Enzymology* 260:213–223, 1995; Scholte et al., *Mol. Cell. Biochem.* 174:61–66, 1997; Almeida et al., *Brain Res.* 764:167–172, 1997; Schild et al., *Acta Opthalmol. Scand.* 74:354–357, 1996). Thus, according to certain embodiments of the present invention a biological sample as provided herein may comprise one or more isolated mitochondria, preferably provided as a suspension in a liquid medium such as a suitable aqueous buffer. More preferably such a buffer is a "respiratory medium" capable of supporting mitochondrial respiratory activities (e.g., oxidative phosphorylation), and still more preferably such a respiratory medium permits maintenance of mitochondrial membrane potential as described herein.

In addition to the methods cited above, preparation of mitochondria in certain preferred embodiments may employ the methods and compositions (including respiratory media) described in Greenawalt et al. (1970 *J. Cell Biol.* 46:173), Greenawalt (1979 *Meths. Enzymol.* 55:88) or Pederson et al. (1978 *Meth. Cell Biol.* 20:411). Further according to the certain embodiments of the invention wherein the biological sample comprises one or more isolated mitochondria and a calcium indicator molecule in a medium (such as a respiratory medium), the calcium indicator molecule capable of generating a detectable signal that is proportional to the level of calcium in the sample is preferably an indicator of intramitochondrial calcium such as Rhod-2 or a derivative thereof (e.g., Rhod-2-AM), membrane permeable forms of Fura-2 or a derivative thereof (e.g., Fura-2-AM) or aequorin. These and other suitable indicators are available from Molecular Probes, Inc. (Eugene, Oreg.) and are described in Haugland, 1996 *Handbook of Fluorescent Probes and Research Chemicals—Sixth Ed.*, (Molecular Probes, Eugene, Oreg.) including the references cited therein. According to certain other embodiments of the invention wherein the biological sample comprises one or more isolated mitochondria and a calcium indicator molecule in a medium (such as a respiratory medium), the calcium indicator molecule capable of generating a detectable signal that is proportional to the level of calcium in the sample is preferably an indicator of extramitochondrial calcium such as Calcium Green™ 5N or a non-membrane permeable form of Fura-2 such as a Fura-2 salt, which indicators are also available from Molecular Probes, Inc. (Eugene, Oreg.), and which are also, along with other suitable indicators, described in Haugland (1996). As noted elsewhere herein, under certain conditions calcium cation transport across the mitochondrial inner membrane may be mediated by a known $Na^+/Ca^+$ antiporter (and/or by a $Ca^+/H^+$ exchanger), albeit at markedly lower kinetic rates than the mitochondrial calcium uniporter. It may therefore be desirable according to certain embodiments disclosed herein to perform the subject invention methods in the absence of any exogenously introduced sodium cations, which according to non-limiting theory should eliminate or reduce any detectable contribution by the $Na^+/Ca^+$ antiporter to the calcium signal level.

Methods are also known in the art for the preparation of submitochondrial particles (SMPs) from isolated or semi-purified mitochondria (see, for example, Walker et al., *Methods in Enzymology* 260:163–190, 1995; and Garlid et al., *Methods in Enzymology* 260:331–348, 1995). Although structurally distinct from the mitochondria from which they are isolated, SMPs remain many functions of intact mitochondria (see, for example, Muscari et al., *Biochim. Biophys. Acta* 1015:200–204, 1990; and Sastrasinh et al., *Am. J. Physiol.* 257:F1050–F1058, 1989).

Figure 2:
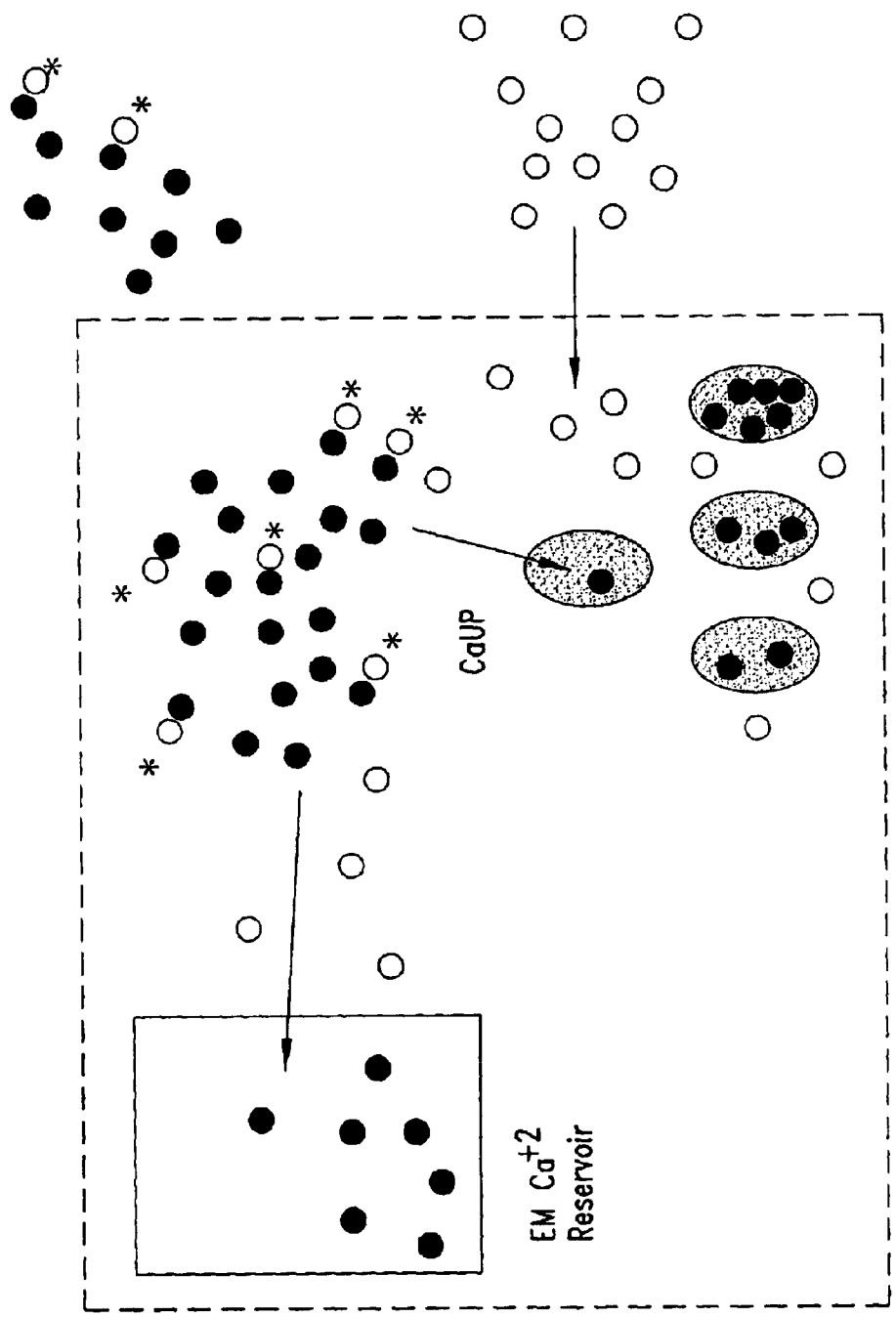
FIG. 2 depicts the entry of a reagent (represented as "○" in the figure) capable of providing a detectable signal in a calcium-sensitive manner into permeabilized cells. When a molecule of the calcium-sensitive reagent combines with a calcium ion, detectable signals (asterisks) are emitted. Other symbols and abbreviations, same as in FIG. 1. Calcium ions in the media and the cytosolic space are detected in this embodiment of the assay, but the calcium-sensitive detectable reagent cannot enter mitochondria and other (extramitochondrial) calcium reservoirs, and calcium ions sequestered in mitochondria or extramitochondrial calcium reservoirs are thus not detected.
Figure 3:
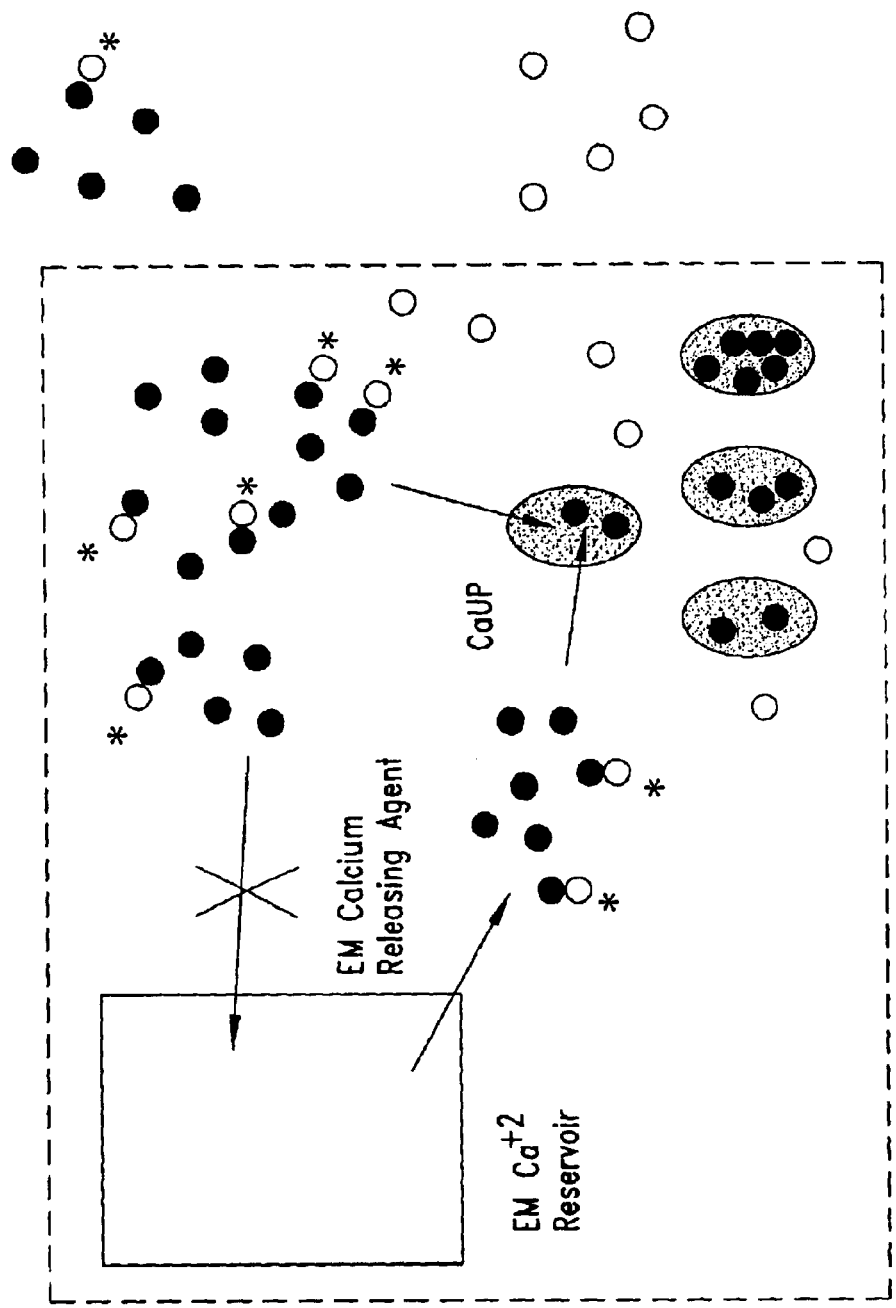
FIG. 3 depicts an embodiment of the assay of the invention in which an extramitochondrial (EM) calcium reservoir releasing agent is present. Symbols, same as in FIGS. 1 and 2. In this embodiment of the assay, calcium ions sequestered in EM calcium reservoirs are released therefrom and/or prevented from entering such reservoirs. As a result, mitochondria are a sole or main site of sequestration of calcium ions, and changes in the levels of detectable calcium ions correspond solely or at least mainly to the influx (or efflux) of $Ca^{2+}$ into (or from) mitochondria. In the figure, calcium ions are shown entering mitochondria due to the action of the calcium uniporter (CaUP).

In certain embodiments of the invention, by using the appropriate combination of calcium-sensitive detectable reagents and ICMAs, a signal that corresponds to the uptake or release of $Ca^{2+}$ from a particular intracellular $Ca^{2+}$ reservoir, such as the mitochondrion, is generated. For example, if ICMAs that are used to block uptake and/or promote release from the ER and other extramitochondrial $Ca^{2+}$ reservoirs, and a calcium-sensitive detectable reagent that does not enter mitochondria is used, any changes in the concentration of the detectable $Ca^{2+}$ signal is due to the uptake or release of $Ca^{2+}$ from mitochondria (see FIGS. 1–3).

In addition to mitochondria, known intracellular calcium reservoirs include other organelles such as the endoplasmic reticulum (ER). The ER is found in most cell types and is composed of a series of flattened sheets, tubes and sacs that enclose a large intracellular space. The membrane of the ER is in structural continuity with the nuclear membrane and extends throughout the cytoplasm. Some functions of the ER include the synthesis and transport of membrane proteins and lipids. Generally speaking, two types of ER may exist in a cell. Smooth ER are generally tubular in shape and are typically devoid of attached ribosomes; one major function of smooth ER is lipid metabolism. Rough ER typically occurs as flattened sheets, the cytosolic side of which is usually associated with many active (protein-synthesizing) ribosomes.

Thus, in one embodiment, the invention provides an assay for extramitochondrial calcium and factors, such as the calcium uniporter (CaUP), that influence levels of mitochondrial calcium, and methods of screening for agents (e.g., chemical compounds) that affect such factors or otherwise influence levels of mitochondrial calcium. In this embodiment, ICMAs (all from Calbiochem, San Diego, Calif., unless otherwise stated) that prevent the uptake by and/or promote the release of calcium from the ER and other extramitochondrial calcium reservoirs are used. Such agents include, by way of example and not limitation, for the ER, thapsigargin and thapsigaricin.

In another embodiment, the invention provides an assay for calcium excluded from the ER and factors that influence the level of $Ca^{2+}$ in the ER, and methods of screening for agents (e.g., chemical compounds) that influence levels of $Ca^{2+}$ in the ER. In this embodiment, ICMAs (all from Calbiochem, San Diego, Calif., unless otherwise stated) that prevent the uptake by and/or promote the release of calcium from mitochondria and other calcium reservoirs other than the ER are used; such agents include, by way of example and not limitation, for mitochondria, ruthenium red and Ru-360, and uncouplers such as CCCP and FCCP.

The invention solves the following problems or overcomes the following limitations. (1) Total extramitochondrial $Ca^{2+}$ can be measured (2) in a real-time kinetic assay thereof that (3) provides for high throughput screening (HTS) for compounds that influence the action of endogenous molecules, or molecules artificially introduced into cells, wherein such molecules regulate extramitochondrial calcium levels, either directly or indirectly. The invention provides the following advantages: (A) Assays can be done under conditions that allow the mitochondrial membrane potential to be the driving force for the calcium uniporter; (B) Conflicting signals from extramitochondrial calcium reservoirs can be reduced or eliminated; (C) Because of (A) and (B), the assays of the invention provides an assay specific for the mitochondrial calcium uniporter.

The $Ca^{2+}$ uniporter (Ca UP) is driven by the mitochondrial membrane potential (low affinity, high Vmax) and is competitively inhibited by $Sr^{2+}$, $Mn^{2+}$, $La^{3+}$; inhibited by $Mg^{2+}$, Ruthenium Red, Ru360; activated by ADP and inhibited by ATP; and is responsible for $Ca^{2+}$ sequestration that stimulates the mitochondrial permeability transition (MPT) Pore. Also, the $Ca^{2+}$ uniporter is clearly implicated in ischemia/reperfusion injury in a variety of tissues, as well as in the excitotoxic death of neurons and may play a role in chronic neurodegenerative diseases in which the ability of cells to cope with large $Ca^{2+}$ loads has been compromised. The CaUP has not been cloned.

Technical details relating to the performance of assays according to certain embodiments of the present invention are described herein, and examples of suitable conditions may be found, for instance, in Murphy et al. (*Proc. Natl. Acad. Sci USA*. 93:9893–9898, 1996). In brief, in some embodiments of the invention, cells are permeabilized in the presence of respiratory media (potassium chloride-based, containing mitochondrial respiratory substrates such as glutamate, malate, succinate, pyruvate plus malate, and numerous others) with a calcium-sensitive detectable reagent. This reagent can be, for example, Calcium-Green-5N (Molecular Probes, C-3737, hexapotassium salt) used at 0.1 to 1.0 micromolar. Other calcium-sensitive detectable reagents, including but not limited to those presented in Table 1, can be used. The cells are currently suspended in the medium, but they could potentially be attached to the surface of the 96-well plate. For the suspended cell assay, the cells are at a concentration of $\sim 1\times 10^7$ cells/ml, 0.1 ml per well). One skilled in the art can determine appropriate cell concentrations for different assay reagents, cell lines, instrumentation, etc.

TABLE 1

CALCIUM-SENSITIVE DETECTABLE REAGENTS

| Calcium-Sensitive Detectable Reagent | Commercial Source(s)[1] | Notes |
|---|---|---|
| Arsenazo III | Cal | useful for spectrophotometric measurements |
| Chlortetracyline | Cal | fluorescent |
| FF6 & AM ester[2] | Cal | fluorescent; properties similar to Fura-2 |
| Fluo-3 & AM ester | Cal, MP | fluoresces upon binding calcium |
| Fluo-3FF & AM ester | Cal | similar to Fluo-3, but lower affinity for calcium and insensitive to magnesium |
| Fura-2 & AM ester | Cal, MP | fluorescent |
| Fura-2FF & AM ester | Cal | similar to Fura-2, but lower affinity for calcium and insensitive to magnesium |
| Fura-PE3 & AM ester | Cal | resists rapid leakage & compartmentalization sometimes seen w/Fura-2 |
| Indo-1 & AM ester | Cal, MP | shift in fluorescence emission (482 → 398 nm) upon $Ca^{2+}$ binding |
| Indo-1FF & AM ester | Cal | similar to Indo-1, but lower affinity for calcium and insensitive to magnesium |
| Quin-2 & AM ester | Cal, MP | $Ca^{2+}$ binding causes major shift in uv absorption spectrum |
| Rhod-AM | MP | loads into mitochondrial matrix |
| Mitochondrially-directed aequorin | MP | luminescent in the presence of $Ca^{2+}$ when reconstituted with coelenterazine and $O_2$ |

[1]"Cal," Calbiochem, San Diego, CA; "MP," Molecular Probes, Eugene, OR;
[2]"AM ester," acetoxymethyl ester.

The media can contain a chelating agent including but not limited to, BAL (British Anti-Lewisite), DMPS (2,3-dimercapto-1-propanesulfonic acid), EDTA (ethylenediamine-tetraacetic acid), DMSA (meso-2,3-dimercaptosuccinic acid), Penicillamine, DTPA (diethylenepentaacetic acid, Desferrioxamine, DTC (dithiocarbamate), and the like. The purpose for adding chelating agents to is to remove potentially contaminating $Ca^{2+}$ which may be present in the cellular media or in other reagents used in the assays of the invention. At some level, contaminating calcium ions could lead to undesirable $Ca^{2+}$ sequestration by mitochondria prior to the beginning of the assay; this will in turn limit the amount of additional calcium that mitochondria can sequester. The appropriate concentration of a chelating agent is determined empirically, or atomic absorption can be done on media to examine the amount of calcium present therein, or different concentrations of the chelating agent can be added, in the presence of a calcium-sensitive detectable reagent, to the media or reagents, and fluorescent signal corresponding to calcium levels is measured. From the results of these determinations, it is possible to determine the minimum concentration of chelating agent beyond which no farther changes in fluorescence can be realized; this concentration of chelating agent is the minimum required to remove endogenous calcium from media and reagents if need be.

Additionally or alternatively, the media can contain the ICMA thapsigargin to prevent $Ca^{2+}$ uptake and retention by the endoplasmic reticulum (ER).

When Calcium-Green™-5N is used, fluorescence reading may be done in laser fluorometer such as Molecular devices' FLIPR at 488 um excitation, emission peak at 530±12.5 um. Once baseline fluorescence is established, a known quantity of $Ca^{2+}$ can be added (robotically by the FLIPR from a concentrated stock in respiratory media), resulting, in the immediate term, in an increase in signal (fluorescence).

The amount of $Ca^{2+}$ to be added is dependent upon the number of mitochondria in the assay. In general, the dose of $Ca^{2+}$ should be low enough so as to not induce opening of the MPT pore (Bernardi et al., *J. Biol. Chem.* 267:2934–2939, 1992; Bernardi et al., *J. Biol. Chem.* 268:1005–1010, 1993; Szabo et al., *J. Biol. Chem.* 267:2940–2946, 1992; Zoratti et al., *Biochem. Biophys. Acta—Rev. Biomemembranes* 1247:139–176, 1995).

Typically, a dose response curve for $Ca^{2+}$ is done for a cell line, with the output being a spontaneous release of $Ca^{2+}$ from $Ca^{2+}$-loaded mitochondria or a transition-like behavior, with $Ca^{2+}$ concentrations of, e.g., 0.1, 0.5, 1.0, 2.5, 5.0, 7.5, 10, 12.5, 15, 20.0, 25, 30, 50, 75 and 100 uM. The optimal concentration of $Ca^{2+}$ for a particular cell line is determined as a concentration well below the maximal $Ca^{2+}$ uptake capacity as determined by repeated pulses of known quantities of $Ca^{2+}$ (Murphy et al., *Proc. Natl. Acad. Sci. USA* 93:9893–9898, 1996). For Hep2 (human hepatoma) cells, an appropriate concentration of $Ca^{2+}$ is 6 to 20 micromolar $CaCl_2$ with 1×10 e7 cells/ml in 0.1 milliliter.

As the calcium uniporter functions, mitochondria take up calcium from the media, but the calcium-sensitive detectable reagent is not taken up into mitochondria; the signal thus decreases to basal or near-basal levels. Uniporter activity thus corresponds to a decrease in signal (due to mitochondrial sequestration of $Ca^{2+}$) following the initial "spike" immediately after calcium is added to the media.

In one form of the assay, following this initial sequestered pulse of $Ca^{2+}$, a test compound is added to the cells before a second $Ca^{2+}$ pulse is applied. A test compound is an agent that is being screened for its ability to influence mitochondrial $Ca^{2+}$ levels in a number of ways (see FIG. 4).

First, some agents will result in a rise in the signal from the calcium-sensitive detectable reagent even before the second $Ca^{2+}$ pulse is applied to the cells. For example, an agent that induces MPT uncouples respiration and/or causes a loss in the mitochondrial membrane potential or otherwise gross structural damage to mitochondria, will cause the $Ca^{2+}$ sequestered from the first $Ca^{2+}$ pulse to be rapidly released from mitochondria, causing an immediate rise in the signal from the detectable reagent. Similarly, an agent that stimulates the efflux of $Ca^{2+}$ from mitochondria by, for example, altering the activity of a mitochondrial divalent cation channel or transporter (including the calcium uniporter) will result in a rise in signal immediately or soon after the cells are contacted with the agent. For example, agents that uncouple respiration dissipate the mitochondrial membrane potential, which acts as the driving force for uptake and retention of $Ca^{2+}$. Moreover, dissipation of delta psi allows the uniporter to function in reverse, allowing $Ca^{2+}$ back out of the mitochondria down its concentration and electrical gradients. A respiratory inhibitor would behave similarly, although the increase in signal might not be as rapid.

Figure 4:
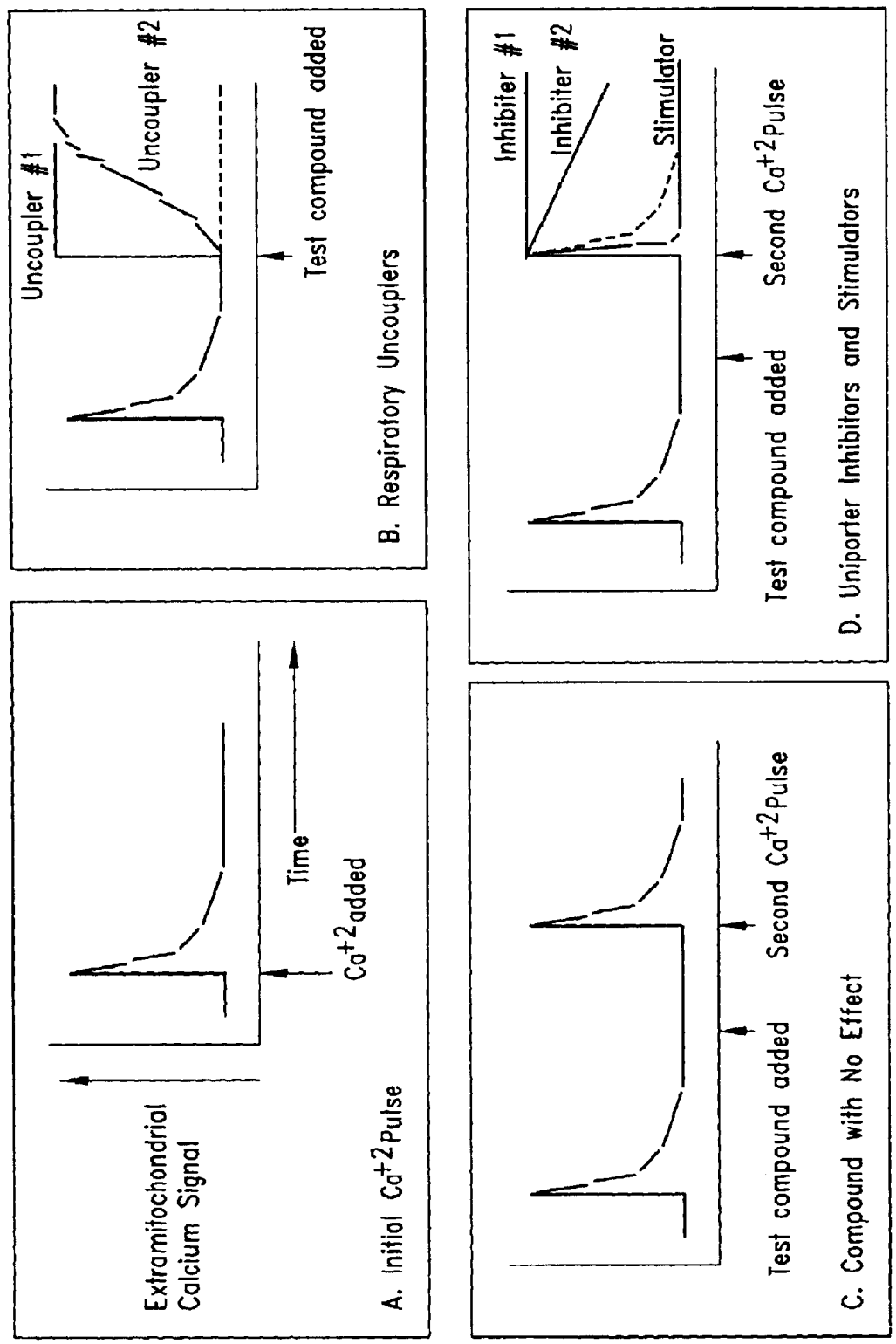
FIG. 4 is a schematic reflecting idealized results of an assay of the invention. The initial $Ca^{2+}$ pulse is shown in panel A, wherein the signal corresponding to extramitochondrial $Ca^{2+}$ decreases soon after calcium is added as the calcium uniporter (CaUP) acts to sequester $Ca^{2+}$ ions in mitochondria. In panel B, the test compounds added to the permeabilized cells are respiratory uncouplers or inhibitors, which causes the CaUP to act in reverse; that is, under these conditions, CaUP stimulates the release of Ca from, instead of uptake into, mitochondria. This release of mitochondrial $Ca^{2+}$ causes the signal corresponding to extramitochondrial $Ca^{2+}$ to increase immediately or soon after the test compound is added (dotted line indicates results in the absence of a test compound). In panel C, the test compound has no effect on respiration or the calcium uniporter, as shown by the fact that a second pulse of $Ca^{2+}$ is taken up by mitochondria with the same kinetic profile as in the initial $Ca^{2+}$ pulse; the same result would occur if no compound were added before the second pulse of $Ca^{2+}$. In panel D, the test compounds are, as indicated, either inhibitors or stimulators of the calcium uniporter, and the dotted line indicates the results expected in the absence of test compound.

Second, an agent that specifically influences uniporter activity may have little or no effect on the signal immediately after the agent is added, but will result in a second $Ca^{2+}$ pulse that has a different sequestration curve than the initial $Ca^{2+}$ pulse (some examples are shown in FIG. 4). For example, a less rapid loss of signal after application of the second $Ca^{2+}$ pulse, indicating a less rapid mitochondrial sequestration of $Ca^{2+}$, indicates that the test compound is an agent that inhibits activity of the calcium uniporter. In the extreme case, application of a sufficient amount of an agent that irreversibly inhibits the calcium uniporter would result in an increased signal that "plateaus" (i.e., does not decrease) after the second $Ca^{2+}$ pulse. As another example, a more rapid loss of signal after application of the second $Ca^{2+}$ pulse, indicating a more rapid mitochondrial sequestration of $Ca^{2+}$, indicates that the test compound is an agent that stimulates activity of the calcium uniporter or inhibits $Ca^{2+}$ efflux.

Example 1

General Assay Reagents, Other Components and Conditions

Calcium

Calcium chloride ($CaCl_2$) is commercially available (Sigma, St. Louis, Mo.; C3881). In initial experiments, atomic absorption was done on the stock calcium chloride solution in order to precisely determine its concentration. Autoclaved stock solutions of 0.025 mol/L are available (Sigma, St. Louis, Mo.). The concentration of $CaCl_2$ is important because a difference between 4 and 8 micromolar can be important with regard to inducing spontaneous $Ca^{2+}$ release from mitochondria.

Calcium-Sensitive Detectable Reagents

Calcium-Green-5N (potassium salt) is commercially available (Molecular Probes, Eugene, Oreg.; C-3737). Calcium-Green-5N is a low affinity $Ca^{2+}$ indicator (as is, for example, Oregon Green 488 BAPTA-5N). Low affinity indicators are preferred because of the $Ca^{2+}$ concentrations used in the assays. High affinity dyes require a lower $Ca^{2+}$ concentration and therefore a lower number of cells, and thus a lower number of mitochondria, would be required than the number used in the assays. Calcium-Green-5N can be frozen and thawed a limited number of times before it loses potency (as demonstrated by a decrease in the starting fluorescence and diminishing peak values). The stock is thus typically divided into aliquots that go through 10 or fewer freeze/thaw cycles before being discarded.

Other calcium-sensitive detectable reagents that can be used in the assay of the invention include Calcein, Calcein Blue, Calcium-Green-1, Calcium-Green-2, Calcium-Green-$C_{18}$, Calcium Orange, Calcium-Orange-5N, Calcium Crimson, Fluo-3, Fluo-3 AM ester, Fluo-4, Fura-2, Fura-2FF, Fura Red™, Fura-$C_{18}$, Indo-1, Bis-Fura-2, Mag-Fura-2, Mag-Fura-5, Mag-Indo-1, Magnesium Green™, Quin-2, Quin-2 AM (acetoxymethyl) ester, Methoxyquin MF, Methoxyquin MF AM ester, Rhod-2, Rhod-2 AM ester, Texas Red®-Calcium Green™, Oregon Green™ 488 BAPTA-1, Oregon Green™ 488 BAPTA-2, BTC, BTC AM ester, (all from Molecular Probes, Inc., Eugene, Oreg.), and aequorin (Molecular Probes).

Permeabilizing Agents and Methods

Those having ordinary skill in the art are familiar with methods for permeabilizing cells, for example by way of illustration and not limitation, through the use of surfactants, detergents, phospholipids, phospholipid binding proteins, enzymes, viral membrane fusion proteins and the like; by exposure to certain bacterial toxins, such as (α-hemolysin); by contact with hemolysins such as saponin (which is also a nonionic detergent, as is digitonin); through the use of osmotically active agents; by using chemical crosslinking agents; by physicochemical methods including electroporation and the like, or by other permeabilizing methodologies including, e.g., physical manipulations such as, e.g., electroporation. Those skilled in the art familiar with methods for permeabilizing cells will be able to determine the most appropriate permeabilizing agent based on factors including but not limited to toxicity of the agent to a specific chosen cell line, the molecular size of the agent that it is desired to have enter cells, and the like (see, e.g., Schulz, *Methods Enzymol.* 192:280–300, 1990).

Thus, for instance, cells may be permeabilized using any of a variety of known techniques, such as the addition of permeabilizing agents such bacterial toxins such as streptolysin O, *Staphylococcus aureus* α-toxin (a.k.a. α-hemolysin); other hemolytic agents such as saponin; or exposure to one or more detergents (e.g., digitonin, Triton X-100, NP-40, n-Octyl β-D-glucoside and the like) at concentrations below those used to lyse cells and solubilize membranes (i.e., below the critical micelle concentration). Certain common transfection reagents, such as DOTAP, may also be used. ATP can also be used to permeabilize intact cells, as may be low concentrations of chemicals commonly used as fixatives (e.g., formaldehyde). All of the permeabilizing agents described in this paragraph are available from, e.g., Sigma Chemical Co., St. Louis, Mo. (see Sigma catalog entitled "Biochemicals and Reagents for Life Science Research," Anon., 1999, and references cited therein for these and other permeabilizing agents). In many of the experiments described herein, digitonin (digitin) was used a cell permeabilizing agent. Typically, a 10% stock solution in DMSO was made and stored frozen. Table 2 describes optimal concentrations of digitonin for permeabilizing several cell lines.

TABLE 2

OPTIMAL DIGITONIN CONCENTRATIONS FOR SEVERAL CELL LINES

| Cell Line | Optimal Digitonin Concentration for Calcium-Green-5N Assay |
| --- | --- |
| SH-SY5Y (suspended at 1 × 10⁶ cells/well in 0.1 ml) | 0.007% |
| HepG2 (suspended at 1 × 10⁶ cells/well in 0.1 ml) | 0.007% |
| MixCon (adherent; 6 × 10⁵ cells/well for 48 hours) | 0.03% |
| Cybrid 1685 | 0.03% |

Chelating Agents

The assays of the invention can optionally comprise a chelating agent, particularly if supplies or reagents (such as, e.g., H$_2$O) needed to prepare components for the assay that are or may be contaminated by Ca$^{2+}$. EGTA (ethylene glycol bis(β-aminoethyl ether)-N,N,N',N'-tetraacetic acid) is commercially available (Sigma, St Louis, Mo.). EDTA is another agent that can be used to chelate Ca$^{2+}$, although it also chelates Mg$^{2+}$. Other calcium chelators can be used including 1–10 phenanthrolene. A 250 millimolar stock solution of EGTA (pH adjusted to 7.0 with KOH) was typically used in experiments described herein. Optimal concentration of EGTA, if found to be necessary in a given instance, may be influenced by the amount of contaminating Ca$^{2+}$ in a given laboratory supply. It may thus be necessary to do a dose response with both EGTA and the Ca$^{2+}$ pulse size. The pulse size of Ca$^{2+}$ used in the methods of the present invention, as described in, inter alia, FIG. 4, depends on factors such as mitochondrial number and mass, but the range of pulse size can be from one to hundreds of micromolar depending on the particular cell line used in the assay. Mitochondria prepared from different tissues will tolerate different concentrations of Ca$^{2+}$.

Extramitochondrial Calcium Releasing Agents

Thapsigargin is a Ca$^{2+}$ uptake inhibitor of the endoplasmic reticulum (ER) and is commercially available (Calbiochem, San Diego, Calif.). Other agents that release Ca$^{2+}$ from extramitochondrial reservoirs, and/or prevent the uptake of Ca$^{2+}$ into such extramitochondrial reservoirs, include without limitation inositol-1,4,5-triphosphate (Streb et al., *Nature* 306:67–69, 1983; Berridge et al., *FASEB J.* 2:3074–3082, 1988), okadaic acid (Hepworth et al., *Cell Calcium* 21:461–467, 1997), and caffeine.

Agents that Influence Mitochondrial Functions

Ruthenium Red is a cytological stain that inhibits the Ca$^{2+}$ uniporter and therefore uptake of Ca$^{2+}$ into mitochondria (Reed and Bygrave, *Bioch. J.* 140:143–155, 1974). It also blocks release of Ca$^{2+}$ from the sarcoplasmic reticulum (Antonius et al., *Biochem. Biophys. Acta* 816:9–17, 1985; Chiesi et al., *Biiochem. Biophys. Res. Commun.* 154:1–8, 1988) and the sequestering ability of the endoplasmic reticulum (Hurley, *Am. J. Physiol.* 23:621–627, 1988). Ru 360 (Calbiochem, San Diego, Calif.; 557440) is the dinuclear ruthenium amid portion of Ruthenium Red, proposed to be responsible for the inhibition effects of Ruthenium Red (Ying et al., *Biochemistry* 30:4949–4952, 1991; Emerson et al., *J. Am. Chem. Soc.* 115:11799–11805, 1993).

FCCP (carbonyl cyanide p-(trifluoromethoxy)phenyl-hydrazone; Sigma) is a potent uncoupler of oxidative phosphorylation in mitochondria (Heytler et al., *Biophys. Res. Commun.* 7:272, 1962; *Biochem. J.* 195:583, 1981). Other non-limiting examples of respiratory uncouplers include carbonyl cyanide m-chlorophenyl-hydrazone (Sigma) (Heytler et al., *Biophys. Res. Commun.* 7:272-etc., 1962), and those described by Heytler in, e.g., *Methods of Enzymology* 55:462, 1979, and *Pharmacol. Ther.* 10:461–472, 1980, both of which are hereby incorporated by reference.

Rotenone (Sigma) is an inhibitor of mitochondrial electron transport (Fukami et al., *Science* 155:713–716, 1967). Other non-limiting examples of inhibitors of mitochondrial ETC include cyanide, amytal and antimycin.

Oligomycin (Sigma) is an inhibitor of mitochondrial ATPase (Nagamune et al., *Biochim. Biophys. Acta* 1141:231–237, 1993). The combination of oligomycin and rotenone, or rotenone alone, can be used as a positive control to evaluate the effects of greatly reducing or essentially elimination of the membrane potential.

Ethacrynic acid (2,3-dichloro-4-(2methylene-butryl) phenoxylacetic acid; Sigma) removes the ability of cells to tolerate oxidative stress. Ethacrynic acid inhibits glu-atathione S-transferase and thus depletes cells of glutathione (Shen et al., *Biochem. Pharmacol.* 50:1233–1238, 1995). Experiments suggest that mitochondrially localized glutathione has a critical role in the maintenance of mitochondrial function (Seyfried et al., *Neurosci. Lett.* 264:1–4, 1999).

Apoptogens

In certain aspects of the invention, an altered mitochondrial state is induced by exposing a biological sample to compositions known as "apoptogens," agents that induce programmed cell death (PCD or "apoptosis"). For reviews of apoptosis, see Green et al. (*Science* 281:1309–1312, 1998), Raff (*Nature* 396:119–122, 1998), and Susin et al. (*Biochim. et. Biophys. Acta* 1366:151–165, 1998).

A variety of apoptogens are known to those familiar with the art and may include by way of illustration herbimycin A (Mancini et al., *J. Cell. Biol.* 138:449–469, 1997); paraquat (Costantini et al., *Toxicology* 99:1–2, 1995); ethylene glycols (www.ulaval.ca/vrr/rech/Proj/532866.html); protein kinase inhibitors such as, e.g.: staurosporine, calphostin C, caffeic acid phenethyl ester, chelerythrine chloride, 1-(5-isoquinolinesulfonyl)-2-methylpiperazine, N-[2-((p-bromocinnamyl)amino)ethyl]-5-5-isoquinolinesulfonamide, KN-93, genistein, quercitin and d-erythro-sphingosine derivatives; ultraviolet radiation; ionophores such as, e.g., ionomycin, valinomycin and other ionophores known in the art; MAP kinase inducers such as, e.g., anisomycin and anandamine; cell cycle blockers such as, e.g. aphidicolin, colcemid, 5-fluorouracil and homoharringtonine; acetylcholineesterase inhibitors such as, e.g., berberine; anti-estrogens such as, e.g., tamoxifen; pro-oxidants such as, e.g., tert-butyl peroxide and hydrogen peroxide; free radicals such as, e.g., nitrous oxide; inorganic metal ions, such as, e.g., cadmium; DNA synthesis inhibitors such as, e.g., actinomycin D, bleomycin sulfate, hydroxyurea, methotrexate, mitomycin C, camptothecin, daunorubicin and DNA intercalators such as, e.g., doxorubicin; protein synthesis inhibitors such as, e.g., cycloheximide, puromycin, and rapamycin; agents that effect microtubule formation or stability such as, e.g.: vinblastine, vincristine, colchicine, 4-hydroxyphenylretinamide and paclitaxel; gangliosides such as GD3 (Scorrano et al., *J. Biol. Chem.* 274:22581–22585, 1999); agents that may be contacted with cells having appropriate receptors including, by way of example and not limitation, tumor necrosis factor (TNF), FasL, glutamate, NMDA (the preceding are contacted with cells having receptors that mediate the uptake of the indicated agent), corticosterone [with cells having mineral corticoid or glucocorticoid receptor(s)]; agents that are withdrawn from the culture media of cells after some period of time such as, by way of non-limiting example, the withdrawal of IL-2 from lymphocytes; and agents that can be contacted with isolated mitochondria or permeabilized cells including, by way of example and not limitation, calcium and inorganic phosphate, (Kroemer et al., *Ann. Rev. Physiol.* 60:619–642, 1998) and members of the Bax/Bcl-2 family of proteins (Jurgenmeier et al., *Proc. Natl. Acad. Sci. U.S.A.* 95:4997–5002, 1998). Such agents are prepared according to methods known in the art or are commercially available from companies such as, for example, Calbiochem (San Diego, Calif.) and Sigma Chemical Company (St. Louis, Mo.).

Cell Lines

A variety of cells or cell lines or mitochondria isolated or prepared therefrom, can be used in the present invention. Preferably non-yeast eukaryotic cells, particularly differentiated or undifferentiated cells or stem cells of endodermic, ectodermic or mesodermic origin. Preferred examples include, but are not limited to, the following.

"SH-SY5Y" is a line of neuroblastoma cells (Biedler et al., *Cancer Res.*, 38:3751–3757, 1978; see also U.S. Pat. No. 5,888,498, Davis et al., issued Mar. 30, 1999, hereby incorporated by reference).

Cybrids are hybrid cells that include the nuclear genome of a cell and the mitochondria from platelets (U.S. Pat. No. 5,888,498).

"MixCon" refers to a mixture of cybrids derived from multiple patients. (U.S. Pat. No. 5,888,498).

"1685 cybrid" refers to a cybrid cell line that combines the nuclear background of the SH-SY5Y cell line with mitochondria prepared from platelets prepared from a patient tentatively diagnosed with Alzheimer's Disease. See copending U.S. patent application Ser. No. 60/124,673, hereby incorporated by reference.

"L6" is a cell line derived from skeletal muscle myoblasts from rat (*Proc. Natl. Acad. Sci. USA* 61:477–483, 1968; *Dev. Biol.* 23:1–22, 1970; ATCC CRL-1458).

"293" is a human kidney cell line that has been transformed with the transforming gene of adenovirus 5 (ATCC CRL-1573, 45504 and 45505).

"HEPG2" is a hepatocellular carcinoma, human (U.S. Pat. No. 4,393,133; Aden et al., *Nature* (Lond.) 282:615–616, 1979; ATCC HB-8065).

"Jurkat" refers to Jurkat, Clone E6-1, acute T cell leukemia from human (ATCC TIB-152).

Media

Standard cell media were typically from commercial sources as indicated with the Examples. The formula for Basic Respiratory Media (a.k.a. "BReM") is described in Table 3.

TABLE 3

| BASIC RESPIRATORY MEDIA (BREM) | |
|---|---|
| Component (Attribute) | Concentration (Value) |
| KCl | 125 mM |
| $K_2HPO_4$ | 2 mM |
| Hepes | 20 mM |
| (pH) | (adjusted to 7.0 at ambient temperature using KOH) |

In experiments wherein the respiratory media contains glutamate, malate, succinate, $MgCl_2$, Calcium-Green-5N, these additional components are added on the day of the assay. With the exception of Calcium-Green-5N, stock solutions of these additives are stable to freezing and thawing. In contrast, Calcium-Green-5N is a salt that degrades over time (about a month), even if stored at −80° C., and that multiple rounds of freezing and thawing enhances this degradation.

Instrumentation

Depending on the assay, a Fluorometric Imaging Plate Reader (FLIPR™) instrument (Molecular Devices, Sunnyvale, Calif.) is often the instrument of choice for the assays of the invention. The FLIPR™ (Molecular Devices, Sunnyvale, Calif.) has the following desirable features (see www.moleculardevices.com/pages/flipr.html): it uses a combination of a water-cooled, argon-ion laser illumination and cooled CCD camera as an integrating detector that accumulates signal over the period of time in which it is exposed to the image and, as a result, its signal-to-noise characteristics are generally superior to those of conventional imaging optics; it also makes use of a proprietary cell-layer isolation optics that allow signal discrimination on a cell monolayer, thus reducing undesirable extracellular background fluorescence; it provides data in real-time, and can also provide kinetic data (i.e., readings at a multitude of timepoints); it has the ability to simultaneously stimulate and read all 96 wells of a 96-well microplate; it provides for precise control of temperature and humidity of samples during analysis; it includes an integrated state-of-the-art 96-well pipettor, which uses dispensible tips to eliminate carryover between experiments, that can be used to aspirate, dispense and mix precise volumes of fluids from microplates; and, in the case of the FLIPR$^{384}$ instrument, it can be adapted to run sample assays in a robotic or semi-robotic fashion, thus providing for analysis of large numbers of samples in shortest amount of time (e.g., up to about a hundred 96-well microplates per day).

Example 2

General Assay Protocols

A master mix solution (MM Solution) was prepared by the addition of glutamate and malate to final concentrations of 5 millimolar each, MgCl$_2$ to a final concentration of 1 millimolar, EGTA to a final concentrations of 0 to 8 micromolar, and Calcium-Green-5N to a final concentration of 0.1 to 1.0 micromolar, to a basic KCl-based respiratory media ("BReM") that is described in Table 3. Alternative respiratory media can be prepared using sucrose and/or mannitol with or without phosphate buffer. The hexapotassiun salt Calcium-Green-5N (Molecular Probes, Eugene, Oreg.) in the MM Solution is a fluorescent dye that has low binding affinity to Ca$^{2+}$.

Thapsigargin (Calbiochem, San Diego, Calif.), a Ca$^{2+}$ uptake inhibitor of the endoplasmic reticulum (ER), was added to the MM Solution to a final concentration of 1 micromolar to yield a solution designated "MM-T" (i.e., Master Mix with Thapsigargin).

The cell membrane permeabilizing agent digitonin (Sigma, St. Louis, Mo.) was added to MM-T to a final concentration of from about 0.007% to about 0.03% to yield a solution referred to as "MM-TD" (i.e., Master Mix with Thapsigargin and digitonin. CaCl$_2$ was added to MM-T to provide a solution with a determined final concentration of Ca$^{2+}$ for the determination of intracellular Ca$^{2+}$ flux.

The range of appropriate digitonin concentrations for different cell lines varies and is titrated for each cell line as the cholesterol content of the plasma membrane varies with cell type. Therefore different quantities of digitonin are required to selectively permeabilize the plasma membrane of the different cell lines. If too little digitonin is used, the cells will not be sufficiently permeabilized to allow access of the dye and reagents to the extramitochondrial space. When too much digitonin is used, the outer mitochondrial membrane will become permeabilized and consequently release factors such as, for example, cytochrome c, thereby limiting respiration.

Titration of the optimal digitonin concentration for a given cell line can be accomplished by a variety of methods. For example cells can be suspended in an oxygen electrode chamber in BReM in the presence of succinate and the complex I inhibitor rotenone. Digitonin is titrated until a maximal rate of oxygen consumption is reached, thereby determining the optimal concentration of digitonin. In this approach, succinate does not readily cross the plasma membrane. Therefore, optimal permeabilization of the plasma membrane provides optimal levels of oxidizable substrate to the mitochondria.

Alternately the uptake of TTP$^+$ (tetraphenyl phosphonium ion) into the mitochondrial matrix can be monitored. TTP$^+$ is a cation that permeates the mitochondrial inner membrane and distributes across the membrane in a Nernstian manner and its distribution reflects the membrane potential. The TTP$^+$ concentration in the media is monitored using a TTP$^+$-selective electrode. TTP$^+$ does not readily cross the plasma membrane, therefore as the plasma membrane is titrated with digitonin the TTP$^+$ gains access to the mitochondria and is taken up as a function of the membrane potential. The maximal disappearance of TTP$^+$ from the medium is indicative of optimal digitonin concentration. Another, but less sensitive approach to titrating digitonin for an adherent cell line, involves the addition of basic respiratory media (BReM) containing from about 0.04% to about to 0.4% trypan blue to the cells, or a fluorescence plasma membrane impermeant dye such as propidium iodide (5 micrograms/milliliter), with increasing concentrations of digitonin. By light microscopy, or fluorescence microscopy when using propidium iodide, the minimal concentration of digitonin that permeabilizes 100% of the cells can be determined. For trypan blue essentially all of the cells become blue and for propidium iodide essentially all of the cells' nuclei become fluorescent. Table 2 describes results for optimization of digitonin for several different cell lines.

Example 3

Detection of CA$^{2+}$ Uniporter Activity

Assays were performed to optimize the Ca$^{2+}$ concentration whereby the concentration allows for Ca$^{2+}$ uniporter transport into mitochondria but is not high enough to induce permeability transition. Stock solutions (10x) of Ca$^{2+}$ were prepared by addition of CaCl$_2$ to MM-T at final concentrations of 0, 40, 80, 120, 160, and 200 micromolar Ca$^{2+}$. The cells used in this experiment were a mixture of control cybrids (MixCon) from multiple normal individuals (see U.S. Pat. No. 5,888,498). Cells were trypsinized in Dulbecco's modified Eagle's medium with 10% heat inactivated fetal bovine serum (FBS) and added to wells of a 96-well Costar 3603 microplate at a concentration of about 6x10$^4$ cells in 100 microliters per well 48 hours prior to performing assays. Prior to use of the cells, the growth media was aspirated from the wells. One hundred microliters of MM-TD was added to each well to permeabilize the cells. The plate was placed into a Fluorometric Imaging Plate Reader (FLIPR™; Molecular Devices Corporation, Sunnyvale, Calif.), heated to 37° C. and illuminated with a 488 nm excitation wavelength. Each of the 10x Ca stock solutions (i.e., 0, 40, 80, 120 and 160 micromolar Ca$^{2+}$, were dispensed in volumes of 11.1 microliters into wells containing the permeabilized cells to yield test samples having Ca$^{2+}$ concentrations of 0, 4, 8, 12, and 16 micromolar, respectively.

Figure 5:
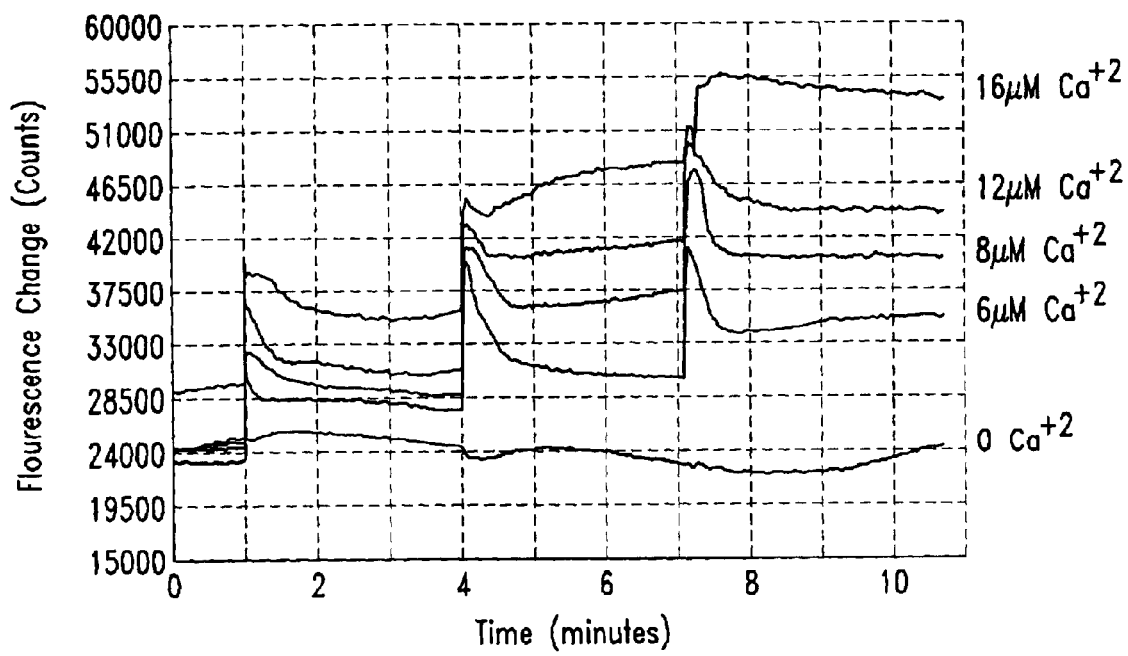
FIG. 5 shows results obtained with one of the assays of the invention wherein MixCon cells were challenged with increasing concentrations (0 to 16 uM) of calcium ions.

As intracellular Ca$^{2+}$ is bound to Calcium-Green-5N, the 531 nm emission increases. As intracellular Ca$^{2+}$ ions cease to be bound to the calcium-sensitive detectable reagent due to their transport into organelles of cells, the resulting emission signal decreases, resulting in a Ca$^{2+}$ 'spike' as monitored in the FLIPR™ (FIG. 4, panel A). Thapsigargin is present to inhibit the uptake of Ca$^{2+}$ into the ER and therefore decreasing cytosolic concentrations of Ca$^{2+}$ in the cytosol reflect the sequesteration of Ca$^{2+}$ in mitochondria. Two additional injections with the 10x CaMM solutions at 3 minute intervals in volumes of 12.3 and 13.7 microliters were performed by the FLIPR system. The results of these assays are shown in FIG. 5, from which it was determined that the appropriate Ca$^{2+}$ pulse size for MixCon cells ranges from about 4 to about 8 micromolar.

Example 4

Detection of Modulation of $Ca^{2+}$ Uniporter Activity

A. General Methods

The effects of several intracellular $Ca^{2+}$ modulating agents (ICMAs) on permeabilized HepG2 cells were examined as follows. The mitochondrial respiratory inhibitors oligomycin (Calbiochem, San Diego, Calif.) and rotenone (Calbiochem) were added to MM-T to final concentrations of 50 micrograms/milliliter and 20 micromolar, respectively. The uncoupler FCCP was similarly added to MM-T to a 10× concentration (10 micromolar) to yield a stock solution of FCCP, MM-TF (i.e., Master Mix with Thapsigargin and FCCP). The ICMA Ru360, which blocks $Ca^{2+}$ uptake into the mitochondria by the calcium uniporter, was added to MM-T to a concentration of 100 micromolar to yield MM-T360 (i.e., Master Mix with Thapsigragin and Ru360). $CaCl_2$ was added to MM-T to yield a 10× solution of $CaCl_2$ (120 micromolar) in MM-T.

HepG2 cells were cultured in Eagle's minimal essential medium (MEM) with non-essential amino acids, sodium pyruvate and Earle's balanced salt solution (BSS), 90%; fetal bovine serum (FBS), 10%. Cells were centrifuged (500×g) and the growth media was aspirated from the pellet. The HepG2 cells were resuspended in MM-TD at a concentration of $1 \times 10^7$ cells/milliliter, and 100 microliters of the resuspended permeabilized cells were dispensed into wells of a 96-well Costar 3603 microplate. The plate was placed into a FLIPR™ prewarmed to 37° C. MM-T, 120 micromolar $Ca^{2+}$, was dispensed into the cell-containing wells at a volume of 11.1 microliters, yielding a final assay concentration of 12 micromolar $Ca^{2+}$. The addition of $Ca^{2+}$ at this stage of the assay is referred to as the first calcium pulse and the time at which $Ca^{2+}$ is added is designated t=0.

After about three minutes (i.e., at about t=3 min.), 12.3 microliters of one of the ICMA solutions were dispensed into wells containing permeabilized cells to yield final assay concentrations of 5 micrograms/milliliter oligomycin, 2 micromolar rotenone, 1 micromolar FCCP, 1 micromolar RU360, and MM-T (no ICMA).

Cells were exposed to a second calcium pulse by the addition of 13.7 microliters of MM-T, 120 micromolar $Ca^{2+}$, to the cells after an additional 3 minutes (i.e., at about t=6 min.). The oxidative phosphorylation inhibitors oligomycin and rotenone, as well as the uncoupler FCCP, caused the release of $Ca^{2+}$ from mitochondria into the cytosol where the $Ca^{2+}$ associated with the $Ca^{2+}$ indicator and the increase in fluorescence was detected by the FLIPR. Upon addition of a the second $Ca^{2+}$ pulse the mitochondria could not sequester the added $Ca^{2+}$ in these cells. The cells in the presence of Ru360 prevented the uptake of $Ca^{2+}$ by the Ca Uniporter. This is reflected in increased levels of $Ca^{2+}$ associated with the calcium indicator in the cytosol. Cells assayed in absence of the ICMA show a decrease in $Ca^{2+}$ associated with the $Ca^{2+}$ indicator after each $Ca^{2+}$ pulse and reflects the uptake of $Ca^{2+}$ into the mitochondria.

B. Methods Using Adherent Cells

Optimization of the $Ca^{2+}$ response curve and time course of $Ca^{2+}$ pulses by the FLIPR™ using Calcium-Green-5N was performed in an adherent cell line. The cell line used was MixCon (see Example 1). $CaCl_2$ was added to MM-T to 10× final concentrations of 0, 40, 80, 100 and 200 micromolar. Immediately prior to the assay, 100 microliters ($2 \times 10^6$ cells/milliliter) of trypsinized MixCon cells in Dulbecco's modified Eagle's medium and 10% FBS growth media were transferred to wells of a 96-well Costar 3603 plate. Wells were coated with Cell-TAK essentially according to the manufacturer's (Becton Dickinson) instructions. The cells were centrifuged onto the plate and the growth media aspirated from the wells, leaving a layer of cells in each well. Cells were permeabilized with the addition of 80 microliters of MM-TD to each well. The digitonin in MM-TD permeabilizes the cells and the thapsigargin in MM-TD inhibits $Ca^{2+}$ uptake by the ER.

Figure 6:
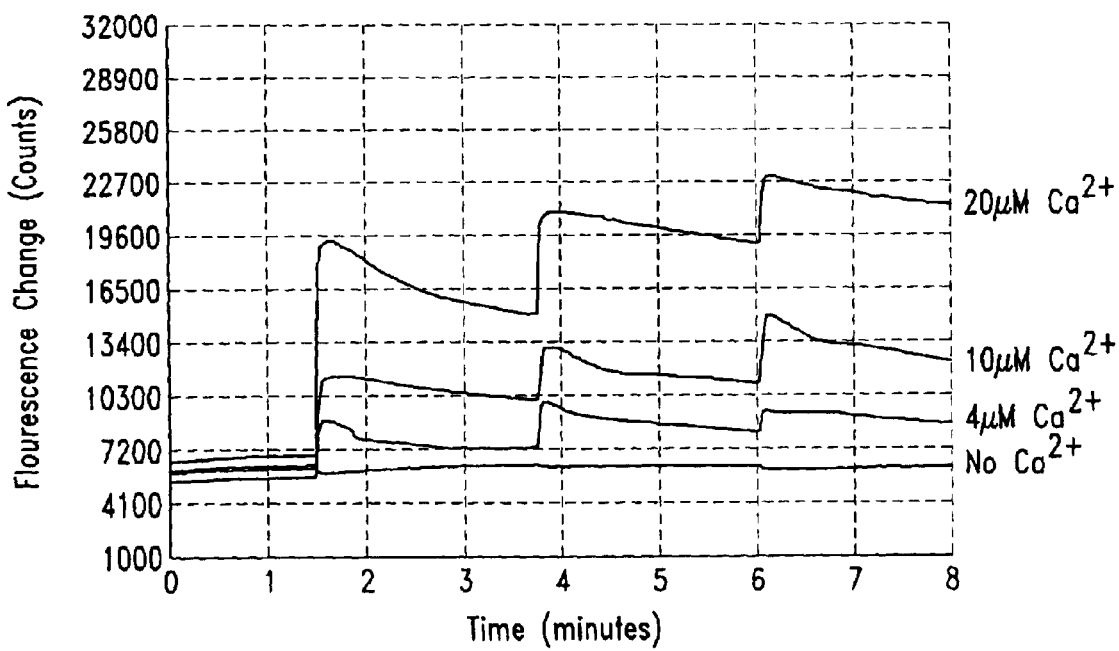
FIG. 6 shows results obtained with one of the assays of the invention wherein MixCon cells were challenged with increasing concentrations (0 to 20 uM) of calcium ions.

Plates were placed in the FLIPR™, and three doses of different 5× stock solutions of $Ca^{2+}$ in MM-T solutions of 0, 40, 80, 100 and 200 micromolar calcium in progressive volumes of 20, 25, and 30 microliters were dispensed into the wells at approximately 2 minute intervals so that concentrations of $Ca^{2+}$ remained at constant levels of 0, 4, 10 or 20 micromolar. Fluorescent emission was monitored at the appropriate wavelength was monitored and cytosolic $Ca^{2+}$ determined throughout assay by the association of $Ca^{2+}$ with the $Ca^{2+}$ indicator. The results with the adherent cell line is presented in FIG. 6.

Figure 7:
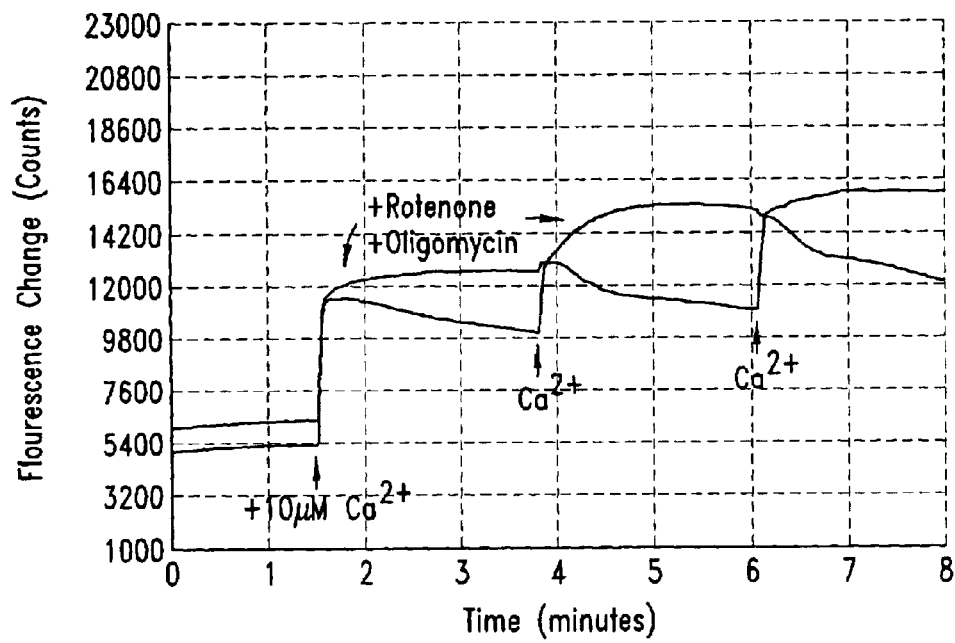
FIG. 7 shows the effect of two compounds, rotenone and oligomycin, that are known to impact mitochondrial functions, on the assay of the invention.

Mitochondrial inhibitors of oxidative phosphorylation, oligomycin and rotenone, were used to observe the effect of decreased membrane potential of mitochondria on cytosol $Ca^{2+}$ levels in the adherent cell line MixCon. The adherent MixCon cells in Dulbecco's modified Eagle's medium and 10% FBS growth media were dispensed into wells of a 96-well microtiter plate at a concentration of about $6 \times 10^4$ cells in 100 microliters per well 48 hours prior to assay. Just prior to their use the growth media was aspirated from the wells. Ninety (90) microliters of MM-TD with oligomycin (5 micrograms/milliliter) or rotenone (2 micromolar), or MM-TD without either inhibitor, were added to the cells. The plate was placed in a FLIPR™ system, and three doses of the 10× stock (100 micromolar) solution of calcium were dispensed into the different wells at approximately 2 minute intervals with increasing volumes (10, 11.1, and 12.3 microliters respectively), resulting in a constant concentration of 10 micomolar $Ca^{2+}$ throughout the course of the assay. Emissions at the 531 nm wavelength were monitored by a FLIPR™ as a measure of extramitochondrial $Ca^{2+}$-Green-5N fluorescence. The signal corresponding to extramitochondrial calcium increased after each pulse and, in samples when remained high when in the presence of the two inhibitors. Alternatively, $Ca^{2+}$ is sequestered in mitochondria of cells not exposed to inhibitors (FIG. 7).

Another assay was performed to examine the effect by the respiratory inhibitors oligomycin and rotenone and subsequent release of $Ca^{2+}$ from mitochondria in the presence or absence of succinate in MixCon cells. Two different master mixes (MM and MM-GMS) were prepared with MM prepared as previously described. MM-GMS was prepared by the addition of glutamate, malate and succinate to final concentrations of 5 millimolar each, $MgCl_2$ to a final concentration of 1 millimolar, EGTA to a final concentration of 10 micromolar, and Calcium-Green-5N to a final concentration of 0.1 micromolar, to a basic KCl-based respiratory media (BReM, Table 3). Thapsigargin was added to the MM and MM-GMS to a final concentration of 1 micromolar to yield MM-T and MM-GMS-T (where "T" indicates Thapsigargin and "GMS" indicates glutamate, malate and succinate. The cell permeabilizing agent digitonin was added to MM-T and MM-GMS-T to a final concentration of 0.03% to yield solutions designated as MM-TD and MM-GMS-TD. As indicated in some instances, the mitochondrial inhibitors oligomycin and rotenone (Calbiochem) were each added to solutions of MM-TD and MM-GMS-TD to final concentrations of 5 micrograms/milliliter and 2 micromolar, respectively.

$CaCl_2$ was added to MM-T and MM-GMS-T to a concentration of 50 micromolar $Ca^{2+}$ to yield 5× $Ca^{2+}$ solutions in MM-T and MM-GMS-T, respectively. Versions of the 5× $Ca^{2+}$ stock solutions comprising respiratory inhibitors were also prepared (oligomycin, final concentration of 50 micrograms/milliliter; rotenone, 20 micromolar).

The MixCon cells, in Dulbecco's modified Eagle's medium and 10% FBS growth media, were dispensed into wells of a 96-well Costar 3603 microtiter plate at a concentration of $6 \times 10^4$ cells in one hundred microliters per well, 48 hours prior to the assay. Just prior to their use the growth media was aspirated from the wells. Eighty (80) microliters of MM-TD, MM-GMS-TD, MM-TD-O, MM-TD-R, and MM-GMS-TD-OR (where "O" oligomycin and "R" signifies rotenone) were dispensed into wells containing the cells. The microtiter plate was placed in a FLIPR™ preheated to 37° C. and an initial injection of 20 microliters of the 5× stock solutions (50 micromolar) of $Ca^{2+}$, with olygomycin, rotenone or no additions, were dispensed into the appropriate wells such that the $Ca^{2+}$ concentration in the assay is 10 micromolar and wells with the inhibitors remain at constant assay concentrations.

Figure 8:
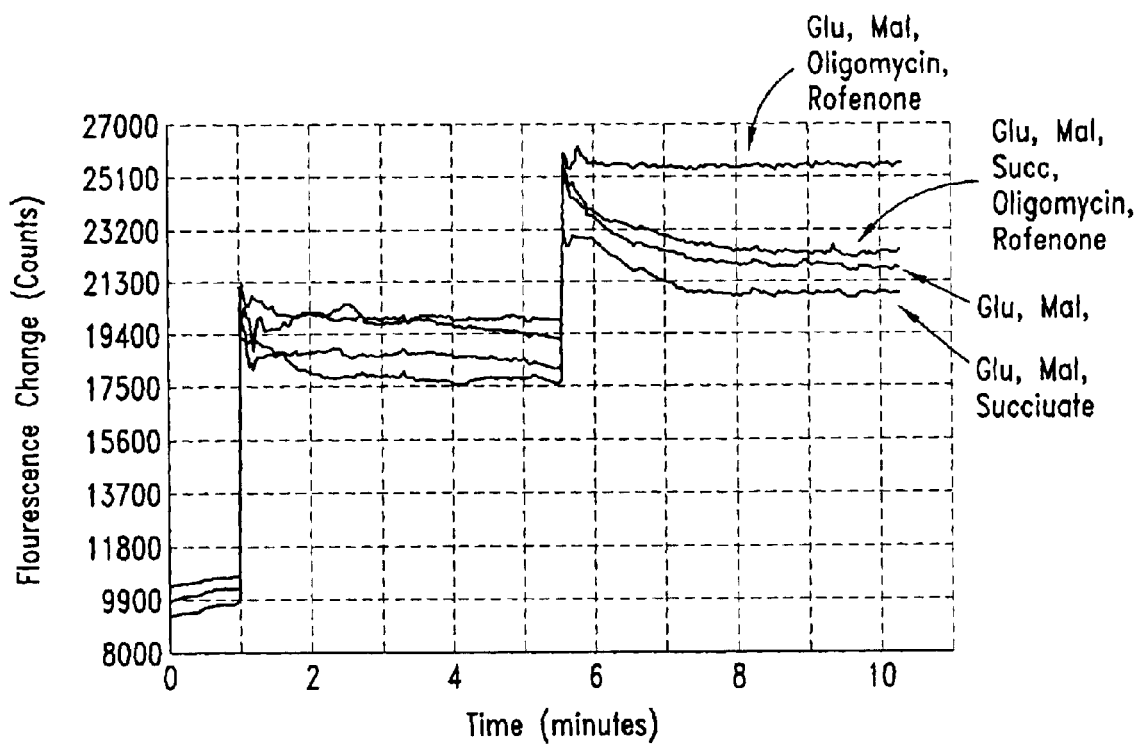
FIG. 8 shows the effects of different optional media components (malate, succinate and glutamate), in various combinations with rotenone and oligomycin.

A second pulse of 25 microliters of the 5× solution was supplied after approximately 5 minutes. The emission wavelength was monitored and intracellular $Ca^{2+}$ determined throughout assay in the FLIPR System. Adherent cells subjected to oligomycin and rotenone in the absence of succinate displayed elevated levels of $Ca^{2+}$-5N fluorescence after the second $Ca^{2+}$ pulse indicative of respiratory inhibition and therefore inhibition of uniporter activity. Alternatively, adherent cells subjected to oligomycin and rotenone in the presence of succinate show a reduction of $Ca^{2+}$-5N fluorescence after the second $Ca^{2+}$ pulse indicating that succinate interferes with the respiratory inhibitors by energizing the mitochondria and providing the driving force for uniporter activity (FIG. 8).

C. Methods Using Suspended Cells

A series of functional assays were performed on non-adherent cell lines in order to optimize the mitochondria Ca—UP assay on FLIPR using Calcium-Green-5N and digitonin permeabilized cells. A dose response of $Ca^{2+}$ pulses with and without the addition of mitochondria oxidative respiration uncouplers were performed utilizing cells from HepG2, a cell line derived from a human hepatocellular carcinoma. MM with thapsigarin, MM-T, and digitonin, MM-TD, are prepared as previously described. Ten times (10×) $Ca^{2+}$ media is prepared by adding $CaCl_2$ (160 micromolar) to MM-T. The L6 cells were suspended in the cell permeabilizing respiratory media MM-TD at a concentration of $1 \times 10^7$ cells per milliliter. One hundred microliters of the suspension were added to each well of a 96-well CoStar 3603 microtiter plate. Digitonin ("D") in MM-TD permeabilizes cells and thapsigargin ("T") in MM-TD inhibits $Ca^{2+}$ uptake by the endoplasmic reticulum (ER). The plates was placed in the a FLIPR™, heated to 37° C.; then, 11.1 microliters of a stock calcium solution (160 micromolar $CaCl_2$ in MM-TD) were dispensed into the 96 different wells containing the L6 cells, resulting in an assay concentration of 16 micromolar of $Ca^{2+}$. After about 3 minutes a second dose (12.5 microliters) of the MM-TD, 160 micromolar $CaCl_2$ solution was dispensed into the wells, thereby maintaining the concentration of $Ca^{2+}$ throughout the assay at 16 micromolar. Emissions resulting from [$Ca^{2+}$:Calcium-Green-5N] complexes were monitored at the appropriate wavelength so as to follow changes in intracellular $Ca^{2+}$ levels throughout the assay. The results are presented in FIG. 9.

Figure 9:
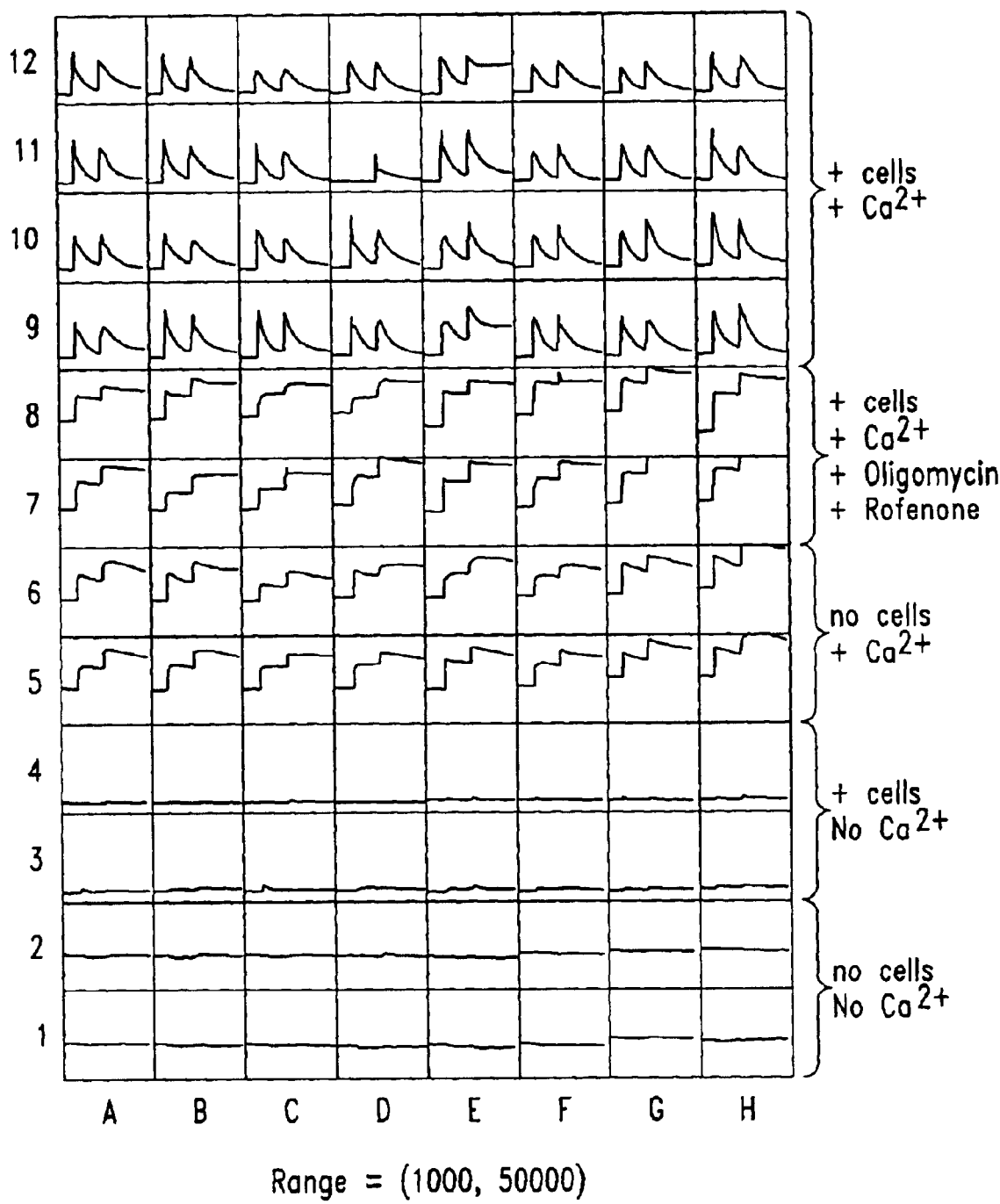
FIG. 9 shows the results of efforts to optimize the concentrations of calcium ions, rotenone and oligomycin for the assay.

Functional assays of the calcium uniporter (CaUP) were similarly performed on non-adherent L6 cells, as described above, with respiratory inhibitors oligomycin and rotenone in order to observe the effects of elimination of the membrane potential using this high throughput FLIPR. Oligomycin and rotenone were added to the MM, 160 uM $CaCl_2$ (see previous example) to concentrations of 50 microgram/milliliter and 20 micromolar, respectively. Cells were prepared and permeabilized as described above, in wells of a 96-well CoStar 3603 microtiter plate. Controls were prepared by the addition of 100 microliters of the permeabilizing solution into wells lacking cells. The plate was placed in a FLIPR and 111 microliters of the MM, 160 uM $CaCl_2$ with inhibitors were dispensed into wells with L6 cells resulting in assay concentrations of 16 micromolar $Ca^{2+}$, 5 microgram/milliliter oligomycin, and 2 micromolar rotenone. MM, 160 uM $CaCl_2$ with no inhibitors was dispensed into the wells lacking cells and having an assay $Ca^{2+}$ concentration of 16 micromolar. After approximately 3 minutes a second dose was dispensed into the wells. The emission wavelength was monitored and intracellular $Ca^{2+}$ levels observed throughout assay. The profiles for cells subjected to addition of $Ca^{2+}$ in the presence of the respiratory inhibitors reflect the profiles of the wells that had $Ca^{2+}$ and possessed no cells illustrating that $Ca^{2+}$ is not sequestered in the mitochondria. When media with no $Ca^{2+}$ is added, the fluorescence changes only minimally (rows 3 and 4)] (FIG. 9).

D. Screening for Modulators of $Ca^{2+}$ Uniporter Activity

Figure 11:
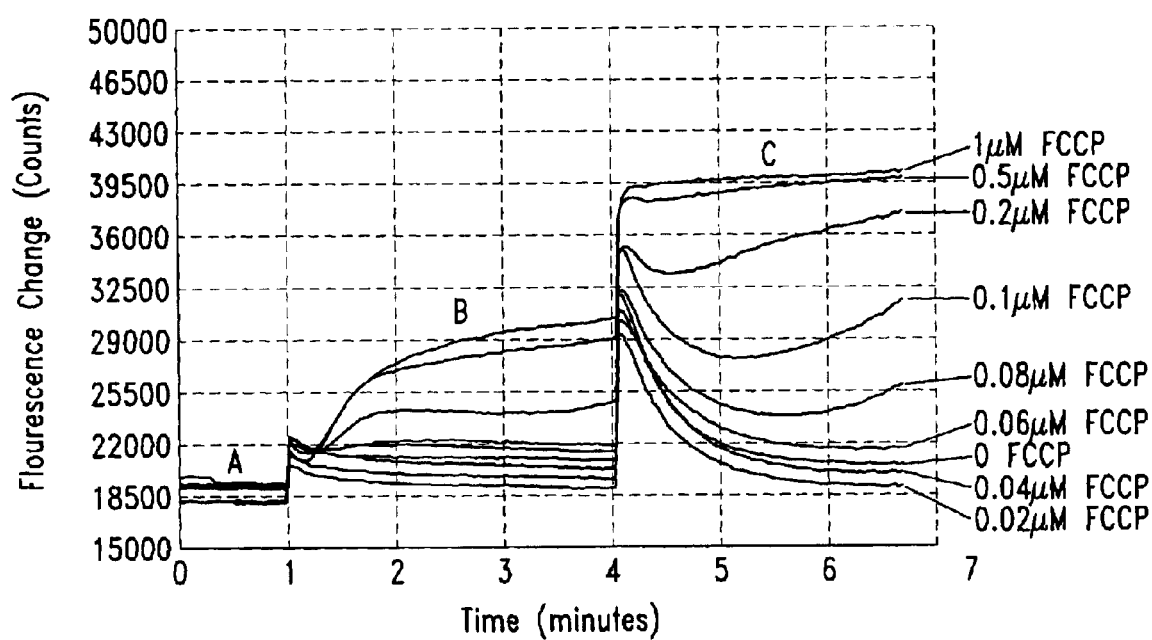
FIG. 11 shows the data presented in FIG. 10 plotted as a function of time.
Figure 12:
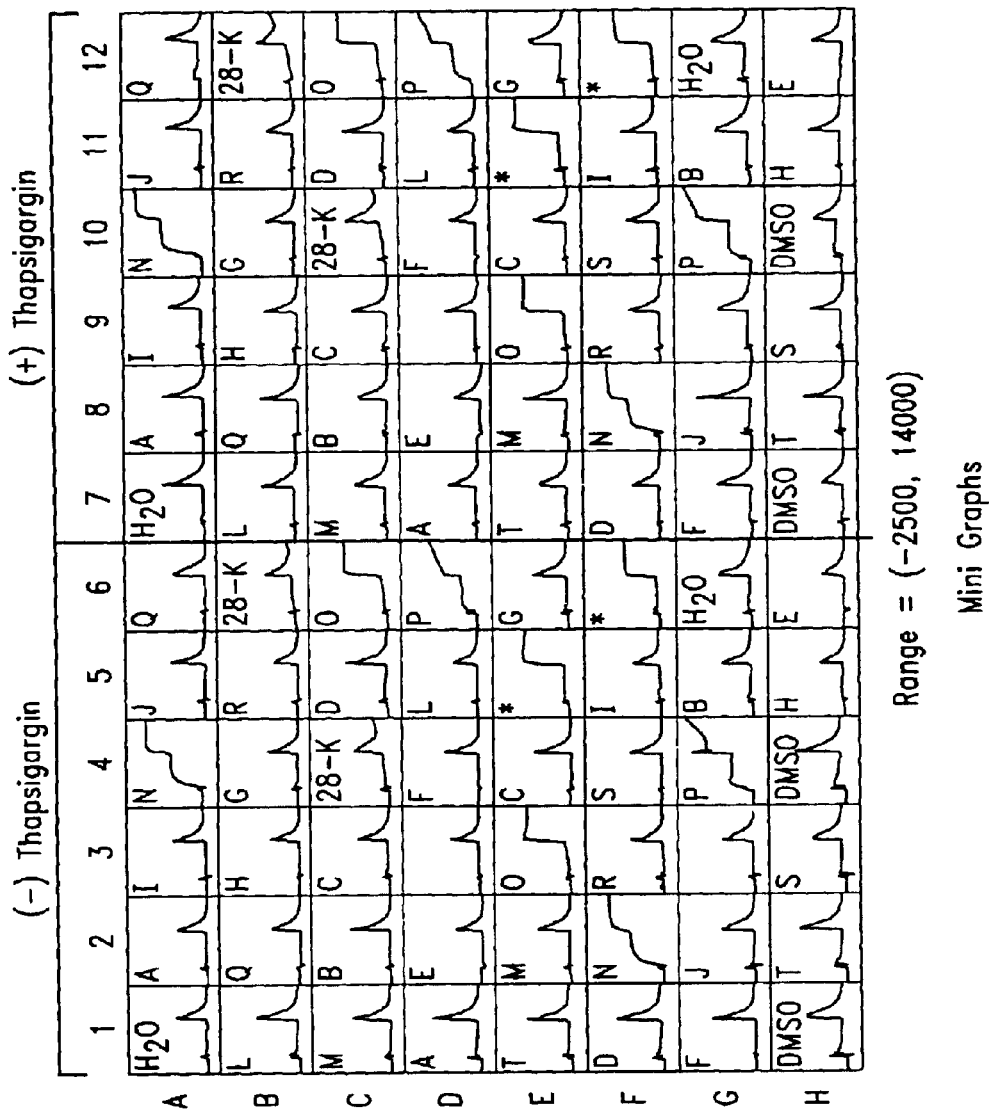
FIG. 12 shows the impact of various agents on calcium levels with (columns 7–12) and without (1–6) thapsigargin.

A uniporter assay was performed in order to observe the inhibitory effect produced by the FCCP (carbonyl cyanide p-(trifluoromethoxy)phenyl-hydrazone; Sigma), a highly effective uncoupler of oxidative phosphorylation in mitochondria. FIGS. 11 and 12 depict dose response experiments wherein FCCP is used as an uncoupler. Such experiments demonstrate the ability of the assays of the invention to detect uncouplers as mitochondrial $Ca^{2+}$ releasing agents and inhibitors of uniporter activity. For drug screening purposes the assay is designed to identify agents that inhibit uniporter activity, but would also identify respiratory uncouplers. In some embodiments, however, it may be preferable to establish a system by which one could screen for molecules that specifically inhibit uniporter activity but have little or no effect on mitochondrial effects.

The basic respiratory media was prepared as described in Table 3, and stored at 4° C., as were stock solutions of 0.5 molar glutamate and malate (Sigma, St. Louis, Mo.; each brought to a pH of 7.0 with KOH) and 1 molar $MgCl_2$ (Sigma). On the day of the assay a master mix solution (MM) was prepared by the addition of glutamate and malate from the stock solutions to final concentrations of 5 millimolar each, 1 millimolar $MgCl_2$, and 0.5 micromolar Calcium-Green-5N (Molecular Probes, Eugene, Oreg.). The hexapotassium salt Calcium-Green-5N (Molecular Probes, Eugene, Oreg.) in the MM is a fluorescent dye that has low binding affinity to $Ca^{2+}$. The cell membrane permeabilizing agent digitonin (Sigma, St. Louis, Mo.) was added to MM to a final concentration of 0.007% to yield a solution designated MM-D. To this mixture $CaCl_2$ was added to a final concentration of 6 micromolar $Ca^{2+}$ to yield a solution designated MM-D, 6 uM Ca. A 10× $Ca^{2+}$ stock solution was prepared by addition of $CaCl_2$ to a final concentration of 200 micromolar in MM (no digitonin), and 10× solutions of FCCP were also prepared in MM to give concentrations of 0, 0.2, 0.4, 0.6, 0.8, 1.0, 2.0, 5.0, and 10.0 micromolar.

HepG2 cells (human hepatocellular carcinoma, ATCC HB-8065) were trypsinized from near-confluent flasks in growth media, Eagle's minimum essential medium (MEM) with non-essential amino acids, sodium pyruvate and Earle's balanced salt solution (BSS), 90%; FBS 10%. Cells were centrifuged, growth media aspirated, and resuspended in the permeabilizing solution MM-D, 6 uM $CaCl_2$. The concentration of cells was adjusted to $1\times10^7$ cells per milliliter in solution. One hundred (100) microliters of the cell suspension ($1\times10^6$ cells) were delivered to the 96 well microtiter plate. The plate was placed in the FLIPR™ unit warmed to 37° C. essentially according to the manufacturer's instructions. An 11.1 microliter aliquot of 10× stock solutions of MM-FCCP, having different concentrations of FCCP, were dispensed into each of 8 wells with cells to yield FCCP assay concentrations of 0, 0.02, 0.04, 0.06, 0.08, 0.1, 0.2, 0.5, and 1.0 micromolar. In like fashion, 11.1 microliters of the 10× stock solutions were added into 8 wells with no cells. FCCP stock solutions were robotically administered one minute after the beginning of the experiment.

Figure 10:
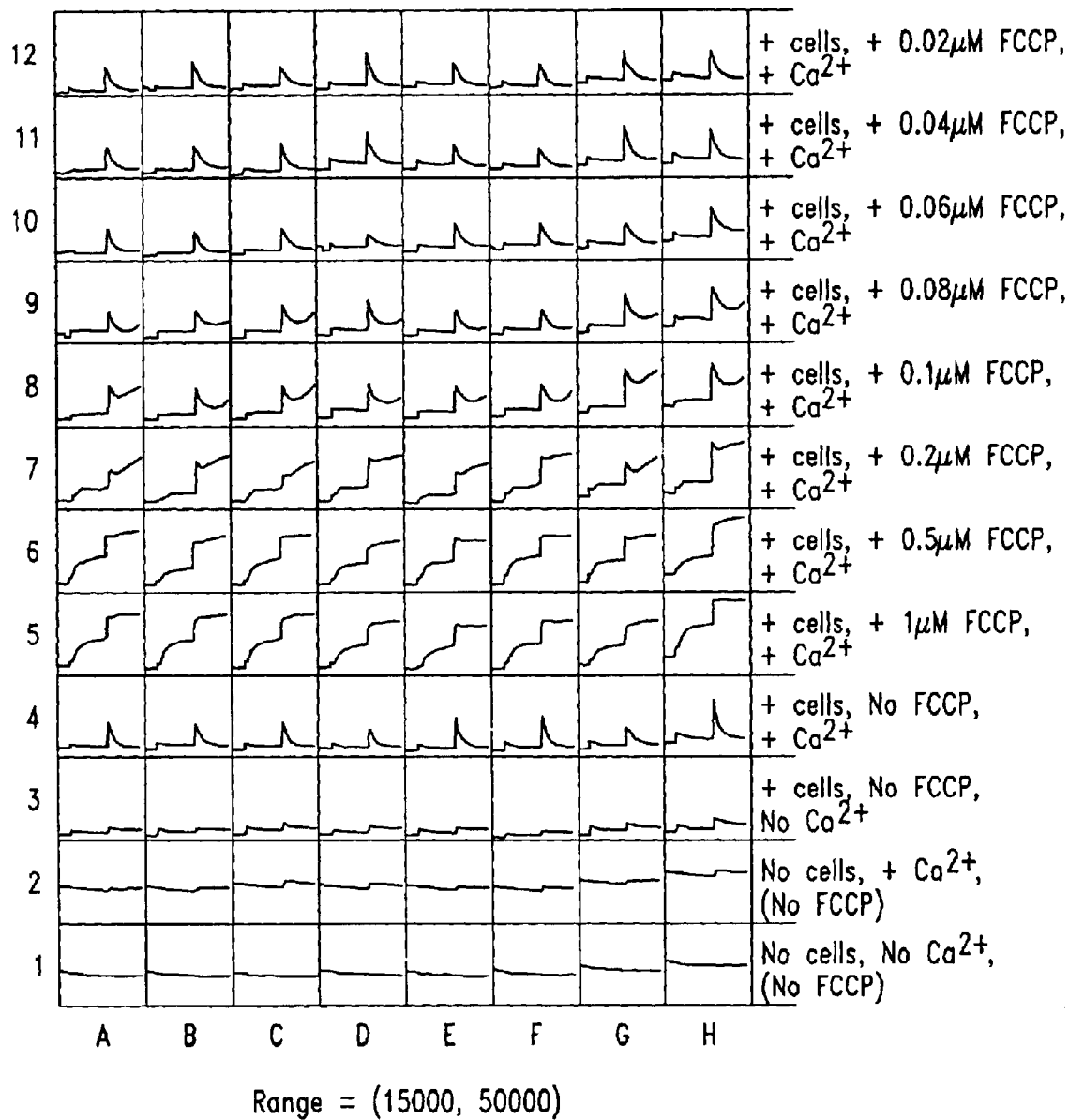
FIG. 10 shows the effect of increasing concentrations of FCCP on the assay of the invention.

A pulse of 12.3 microliters of the 10× stock $CaCl_2$ solution was introduced into each of the wells of the microtiter plates after about four minutes. Emissions resulting from the binding of extramitochondrial $Ca^{2+}$ to the calcium indicator dye were monitored throughout the assay. The emissions from each well of the 12 different assays (8 wells per each assay) were graphed as a function of time (FIG. 10). Row 4 in FIG. 10 shows the results from 8 wells (A–H) when cells and calcium are present. In rows 5 to 12 of FIG. 10, the uncoupler FCCP was present in addition to cells and calcium. The concentration of FCCP decreases as one progresses from Row 5 (1.0 uM) to Row 12 (0.02 uM), and the effect of the uncoupler on CaUP activity decreases in a corresponding manner. The results obtained when 0.02 or 0.04 uM FCCP was present (Rows 12 and 11, respectively) are difficult to distinguish from the results obtained when no FCCP was present (Row 4).

The average of the changes of fluorescence for the assays (1–12) versus time course where FCCP was added at one minute, and calcium was pulsed into the assay media at approximately 4 minutes, were determined and graphed as a function of time (FIG. 11). The fluorescence rises slightly upon addition of FCCP at t=1 min.; without wishing to be bound by theory, this probably occurs as a result of $Ca^{2+}$ that was loaded into the mitochondria when they were first resuspended in MM-D containing 6 micromolar $Ca^{2+}$.

The high-throughput uniporter assay protocol, carried out as described above for suspension cells, was used to determine the effect of different compounds on mitochondria and extramitochondrial $Ca^{2+}$ concentrations in the presence or absence of the $Ca^{2+}$ uptake inhibitor of the endoplasmic reticulum, thapsigargin (Calbiochem). Agents examined in this assay include calcium channel inhibitors, pro- and anti-oxidants, mitochondrial inhibitors and uncouplers, and the Ca—UP inhibitor Ru360. On the day of the assay, solutions of the respiratory/cell permeabilizing media containing digitonin with thapsigarin (MM-TD) and without thapsigarin (MM-D) were prepared as previously described. Calcium chloride was added to each to a final concentration of 6 micromolar $Ca^{2+}$, resulting in MM-TD, 6 uM Ca and MM-D, 6 uM Ca. A MM solution was prepared with a 10× $Ca^{2+}$ concentration of 200 micromolar for the second $Ca^{2+}$ pulse. The $Ca^{2+}$-uniporter inhibitor Ru360 was prepared at a 10× concentration of 100 microliters in MM. Ten times (10×) stock solutions of the other agents were prepared for the assay by the addition of the compounds to final concentrations of 10 micromolar into MM. The agents assayed included: inhibitors of $Ca^{2+}$ channels (not including the uniporter), amiloride (Research Biochemicals International, RBI), nicardipine (RBI), nifedipine (RBI), nimodipine (RBI), trifluoroperazine (RBI), and verapamil (RBI); a calcineurin inhibitor/immunosuppressant drug, FK506 (tacrolimus) (Calbiochem); diltiazem (RBI), an effector of some $Ca^{2+}$ channels; the pro-oxidant diamide (azodicarboxylic acid bis[dimethylamide]) (Sigma, St. Louis, Mo.), and the anti-oxidant N-acetyl cysteine (Sigma); mitochondria uncouplers of oxidative phosphorylation such as CCCP (carbonyl cyanide m-chlorophenyl-hydrazone) (Sigma) and respiratory inhibitor such as rotenone (Sigma); the a $Ca^{2+}$ ionophore, ionomycin (Calbiochem); dantrolene (RBI), an inhibitor of the endoplasmic reticulum $Ca^{2+}$ channel; a $K^+$-channel inhibitor, glyburide (glibenclamide) (Calbiochem); an inhibitor of mitochondrial electron transport, PK-11195 (RBI); a peripheral benzodiaepine receptor antagonist; and the metabolite, creatine (Aldrich, Milwaukee, Wis.). Controls include water and 10% DMSO (Sigma) in MM.

Cells of the HepG2 cell line (hepatocellular carcinoma, ATCC HB-8065) were trypsinized from near-confluent flasks in growth media (Eagle's MEM with non-essential amino acids, sodium pyruvate and Earle's BSS, 90%; FBS 10%). Cells were centrifuged, growth media was aspirated, and cells were resuspended to a concentration of $1\times10^7$ cells per milliliter in MM-TD, 6 uM Ca, or MM-D, 6 uM Ca. One hundred (100) microliters of the cell suspension (about $1\times10^6$ cells) were delivered to wells of a microtiter plate. The plate was placed in a FLIPR™ II (used in 96-well format) warmed to 37° C. An 11.1 microliter aliquot of the 10× stock solutions with water or DMSO (controls), Ru360 (Ca—UP inhibitor), or the test compounds, were dispensed into designated wells such that the assay concentration of DMSO is 0.1%, Ru360 is 10 micromolar, and each of the test compounds are at 1 micromolar concentrations. After an additional three minutes, a second addition of 12.3 microliters of the 10× $CaCl_2$ (200 micromolar $Ca^{2+}$), was dispensed into the wells of the microtiter plate resulting in assay concentrations of 20 micromolar $Ca^2$ (Extramitochondrial $Ca^{2+}$ bound to the calcium indicator dye was monitored throughout and profiles of each assay; the results are presented in FIG. 12, with all thapsigargin minus (thaps–) assays in wells corresponding to columns 1–6 and thapsigargin plus (thaps+) assays in wells corresponding to columns 7–12.

Figure 13A:
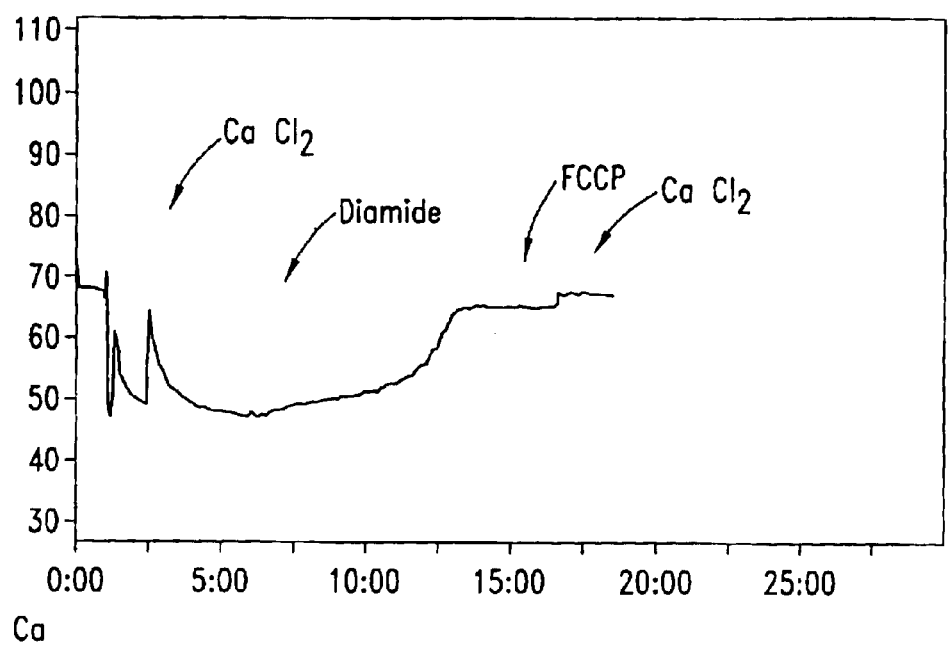
FIG. 13 shows the impact of an MPT effector, diamide, on results obtained using the assay of the invention in the absence (FIG. 13A) and presence (FIG. 13B) of CsA.
Figure 13B:
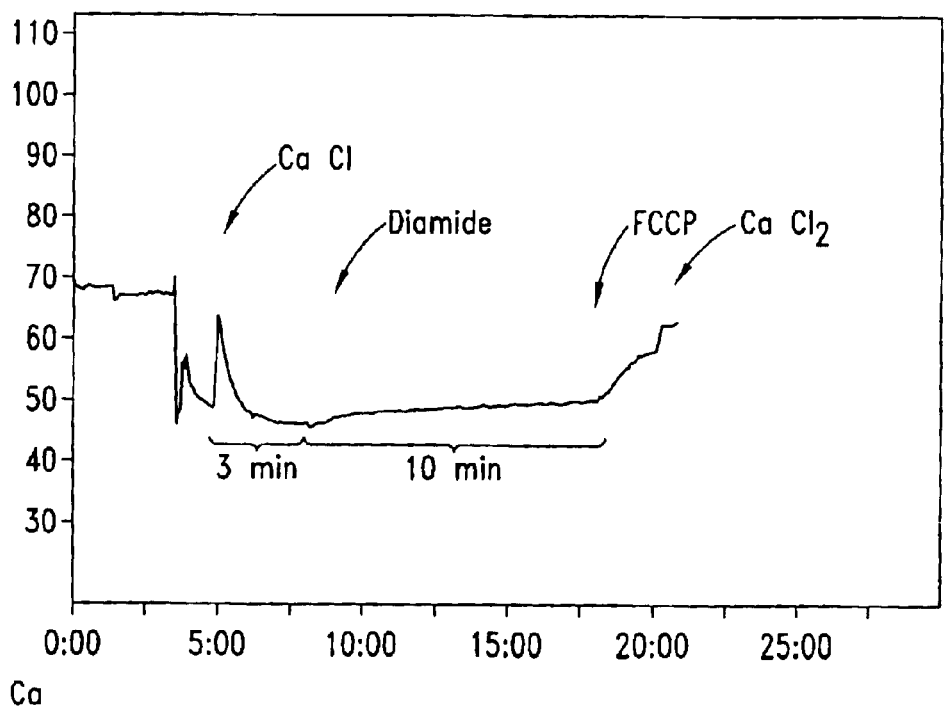

Profiles of all assays are referred to by their location in the microtiter plate, column vs row, of FIG. 13. Upon addition of test compounds, most of the wells indicate little or no change in the fluorescence signal over the ensuing 3 minutes. This indicates little or no effect on the ability of the mitochondria to retain the 6 micromolar $Ca^{2+}$ that was accumulated upon permeabilization. The exception to this is the effect of the uncoupler CCCP (A4, F2, A10, F8) and ionomycin ($Ca^{2+}$ ionophore D6, G4, D12 and G10). There is also a slight indication of $Ca^{2+}$ release in response to atractyloside (B6, C4, B12, C10), an inducer of the permeability transition which induces $Ca^{2+}$ release through opening of a large conductance pore in the inner mitochondrial membrane. Control assays having no affect on uniporter activity are water (A1, G6, A7, G12), and DMSO (H1, H4, H7, H10). The $Ca^{2+}$ 'spike' reflects uptake of $Ca^{2+}$ into the mitochondria and exhibit $Ca^{2+}$-UP activity. Similar profiles are observed for the non-uniporter inhibitors: amiloride (A2, D1, A7, D7); nicardipine (C2, G5, C8, G11); nifidipine (C3, E4, C9, E10); nimodipine (C5, F1, C11, F7); trifluoroperazine (D2, H6, D8, H12); verapamil (D4, G1, D10, G7); and diltiazem (B3, H5, B9, H11), reflecting that they do not possess uniporter inhibitory activity at one micromolar. The uniporter non-inhibitory profile is also observed for: FK506 (B4, E6, B10, E12); diamide (B1, D5, B7, D11);

N-acetylcysteine (C1, E2, C7, E8); dantrolene (A6, B2, A12, B8); glyburide (glibenclamide) (B5, F3, B11, F9); PK-11195 (E1, H2, E7, H8); and creatine (F4, H3, F10, H9). Alternatively, the Ca—UP inhibitor Ru360 shows no uptake of $Ca^{2+}$ by the uniporter upon the $Ca^{2+}$ addition and is reflected in a plateau of $Ca^{2+}$-calcium indicator in the extramitochondrial medium (E5, F6, E11, F12). A similar profile is observed for the respiratory inhibitor rotenone (C6, E3, C12, E9), probably indicating that upon addition of $Ca^{2+}$ the ETC complex I is disabled, the membrane potential is dissipated, and $Ca^{2+}$ can no longer be sequestered by the mitochondria. The uncoupler CCCP (A4, F2, A10, F8; release $Ca^{2+}$ from mitochondria) and $Ca^{2+}$ ionophore (D6, G4, D12, G10; release $Ca^{2+}$ from cell stores) reflect profiles of agents that prevent $Ca^{2+}$ uptake and retention by the mitochondria.

Example 5

Detection of Modulation of Mitochondria Permeability Transition (MPT)

A. General Method

An assay was performed in order to observe the transition induction effect on MPT by the MPT effector, diamide (a thiol oxidizing agent and pro-oxidant). The assay was performed in a digitonin-permeabilized cell line of mixed cybrids, MixCon in the presence of $Ca^{2+}$ and Ca-Green-5N and monitored in an LS50B Perkin Elmer Spectrofluorimeter, but is adaptable to the FLIPR system. Initially, ethacrynic acid was added to the MixCon cells in Dulbecco's modified Eagle's medium and 10% FBS, to a final concentration of 100 micromolar and preincubated for 5 minutes to remove the ability of cells to deal with oxidative stress making cells susceptible to the pro-oxidant. The cells were then centrifuged, growth media was aspirated, and cells resuspended, at $1.1 \times 10^7$ cells/milliliter, in 2 milliliters of respiratory media containing digitonin (MM-D) whereupon the digitonin (dig) permeabilizes the cells. The suspension was then transferred to a spectrofluorimetric cuvette. The cuvette was placed in the fluorimeter and 0.3 microliters of a 254 millimolar $CaCl_2$ stock was added to the cuvette (final $CaCl_2$ concentration of 40 micromolar). After approximately three minutes diamide was added to the cuvette to a final concentration of 500 micromolar]. Within approximately 6 minutes, the mitochondria released the sequestered $Ca^{2+}$ supposedly via the effect of the pro-oxidant on the MPT. Addition of the uncoupler FCCP at an assay concentration of 0.1 micromolar characterizes no further release of $Ca^{2+}$ from the mitochondria. Addition of $CaCl_2$ to 40 micromolar in the assay resulted in increased fluorescence, thus the $Ca^{2+}$-sensitive dye was demonstrated not no to have been saturated with $Ca^{2+}$ under assay conditions (FIG. 13).

To further scrutinize modulation of the MPT the same experiment was performed on MixCon cells, as described above, with the exception that after the cells were permeabilized 10 micromolar of the permeabilty transition blocker, cyclosporin A (CsA), was added. Upon addition of diamide only a slight increase in fluorescence was observed. Supposedly the CsA prevented the pro-oxidant from inducing the MPT as reflected by the maintenance of the reduced level of $Ca^{2+}$ in the extramitochondria medium. Only upon addition of the uncoupler FCCP was $Ca^{2+}$ released from the mitochondria as reflected by the elevated level of $Ca^{2+}$ associated with the $Ca^{2+}$ indicator (FIG. 13).

The transition induction effect on MPT by the MPT effector, diamide (a thiol oxidizing agent and pro-oxidant) were performed with a second cell line, 293T. The 293T cells were suspended in 2 milliliters of growth media, DMEN and 10% FBS, with 100 micromolar of ethacrynic acid ($1 \times 10^7$ cells/ml) and preincubated for 14 minutes to remove ability of cells to deal with oxidative stress making them susceptible to the pro-oxidant. The cells were centrifuged, media aspirated, resuspended in 2 milliliters of respiratory media containing digitonin (MM-D), and transferred into a cuvette. The digitonin (dig) in MM-TD permeabilizes the cells. The cuvette was placed in a LS50B Perkin Elmer Spectrofluorimeter and 40 micromolar $CaCl_2$ in $H_2O$ was added into the suspension. After approximately three minutes 500 micromolar diamide was dispensed into the cuvette. The mitochondria immediately began to slowly release $Ca^{2+}$ to the medium, and this rate substantially increased after about 7.5 minutes, reflecting the pro-oxidant's effect on the MPT. Addition of the uncoupler FCCP at an assay concentration of 0.1 micromolar resulted in no increased level of fluorescence and gave evidence that no additional $Ca^{2+}$ was released from the mitochondria, therefore all $Ca^{2+}$ had been freed into the cytosol by the effect of diamide.

B. Screening for Modulation of MPT Activity Using Adherent Cells or Non-adherent Cells (Cuvettes or FLIPR)

A high-throughput assay with a FLIPR™ 384 was used to observe the modulation of MPT when permeabilized cells were subjected to the mitochondria permeability transition inducer atractyloside (Sigma), permeability transition blockers bongkrekic acid (Calbiochem) and cyclosporin A (CsA), and the pro-oxidant, diamide. HepG2 cells (hepatocellular carcinoma, ATCC HB-8065), in suspension, were used to determine the effect of these compounds on mitochondria $Ca^{2+}$ sequestration by monitoring extramitochondrial $Ca^{2+}$ concentrations in the presence or absence of the $Ca^{2+}$ uptake inhibitor of the endoplasmic reticulum, thapsigargin (Calbiochem, San Diego, Calif.). On the day of the assay solutions of the respiratory media containing digitonin with thapsigarin (MM-TD) and without thapsigarin (MM-D) were prepared as previously described. Calcium chloride was added to each to a final concentration of 6 micromolar $Ca^{2+}$, to yield MM-TD, 6 uM Ca, and MM-D, 6 uM Ca. Ten times (10x) stock solutions were prepared for the assay by the addition of each of the compounds to final concentrations of 10 micromolar in MM. Ten times (10x) solutions of $CaCl_2$ was prepared in MM or MM-T to concentrations of 200 micromolar, for the second addition.

The HepG2 cells were trypsinized from near-confluent flasks in growth media (Eagle's MEM with non-essential amino acids, sodium pyruvate and Earle's BSS, 90%; FBS 10%). Cells were centrifuged, media was aspirated, and the cells were resuspended to $1 \times 10^7$ cells per milliliter in MM-TD, 6 uM Ca and MM-D, 6 uM Ca, whereby $Ca^{2+}$ and the indicator dye enter the cells and $Ca^{2+}$ becomes sequestered in mitochondria. One hundred (100) microliters of the cell suspension was delivered to each well of a microtiter plate. The plate was placed in the FLIPR 384 warmed to 37° C. An 11.1 microliter volume of the 10x stock solutions with the test compounds were dispensed into designated wells such that the assay concentration are 1 micromolar. After a three minute interval, a $Ca^{2+}$ pulse of 20 micromolar was delivered by adding 12.3 microliters of the 10x $CaCl_2$ solutions containing 200 micromolar $Ca^{2+}$. Extraorganelle $Ca^{2+}$ bound to the calcium indicator dye was monitored throughout and profiles of each assay are presented in FIG. 13, with all thapsigargin minus (thaps-) assays in wells corresponding to columns 1–6 and thapsigargin plus (thaps+) assays in wells corresponding to columns 7–12.

Profiles of all assays are referred to by their location in microtiter plate, column vs row, of FIG. 13. Assay activity profiles of most of the compounds, including inhibitors of permeability transition, bongkrekic acid and CsA show that upon addition of the $Ca^{2+}$ pulse the sudden increase in cytosolic $Ca^{2+}$ is observed to decrease resulting in the 'spike' indicative of normal mitochondria sequestration of $Ca^{2+}$. The assay profile of the permeability inducer atractyloside (B6, C4, B12 and C10) show initial uptake of $Ca^{2+}$ into mitochondria with the slow release of the $Ca^{2+}$ into the cytosol, probably through the MPT pore. The pro-oxidant diamide, B1, D5, B7 and 11, reflects sequestering of $Ca^{2+}$ by mitochondria after the $Ca^{2+}$ pulse. This last result differs with that of a similar assay in cuvettes (see above) where diamide had caused the release of $Ca^{2+}$ from mitochondria. The difference is attributed to the diamide concentrations of each experiment where is in cuvettes the assay concentration of diamide was 0.5 millimolar, and in the FLIPR assay the use of 1 micromolar diamide was too low to affect $Ca^{2+}$ sequestration in mitochondria.

Hypothetically, to screen for inhibitors of the mitochondrial membrane permeability transition, the quantity of $Ca^{2+}$ added to the cells following the addition of the test compound could be increased to a level that induces spontaneous $Ca^{2+}$ release. In the absence of any test compound, a tracing indicative of the transition would appear as an increase followed by an inability of the mitochondria to return the extramitochondrial $Ca^{2+}$ concentration back down to baseline. For instance, the $Ca^{2+}$ addition could be increased to approximately 400 micromolar, which would result in mitochondrial $Ca^{2+}$ uptake, followed by stimulation of the opening of this non-specific pore, allowing $Ca^{2+}$ to efflux from the mitochondria. Addition of permeability transition inhibitors such as bongkrekic acid (at 1 micromolar) or cyclosporin A (at 1 micromolar) would inhibit the transition and allow mitochondria to continue $Ca^{2+}$ accumulation to bring the fluorescence level back to baseline.

Example 6

Detection of Modulation of $CA^{2+}$ out of Mitochondria

General Method (cuvettes or FLIPR)

This fluorescence-based assay could be modified to allow screening for compounds that alter the mitochondrial buffer or set point (the concentration of $Ca^{2+}$ outside the mitochondria following activation of uniporter and $Ca^{2+}$ efflux activities). Mitochondrial efflux is normally mediated by either the $Na^+/Ca^{2+}$ exchanger or a $Ca^{2+}/H^+$ antiporter, depending upon the mitochondrial type. To carry out the assay, all the same media and cell and/or mitochondrial preparations could remain as previously described with the exception that no $Ca^{2+}$ would be added to the permeabilization medium, and permeabilization medium would have no added $Ca^{2+}$. The cells could then be dispensed to the microtiter wells, and the first addition could be the addition of $Ca^{2+}$ (approximately 4 to 15 micromolar, but empirically determined to be well below a concentration that induces the permeability transition) followed by 0.1–5 $\mu$M ruthenium Red along with 30 micromolar NaCl to the medium (to enhance the rate of the $Na^+/Ca^{2+}$ exchanger if necessary). The addition of $Na^+$ to cells in which the mitochondria exhibit $Na^+/Ca^{2+}$ exchange activity will result in a return of the fluorescence to a level above the original baseline. The test compound would be added after approximately 3 minutes, and the tracing would be evaluated for either an increase or decrease in the fluorescence compared to the equilibrium established prior to the addition of test compound. A decrease in the steady-state level would be indicative of an efflux inhibitor. An increase in the steady-state level would be indicative of an efflux accelerator. A second pulse of $Ca^{2+}$ of the same magnitude as the first addition could be added. A compound that either speeds influx or inhibits efflux would result in a sharper $Ca^{2+}$ peak and a more rapid return to the previous level of $Ca^{2+}$. An accelerator of $Ca^{2+}$ efflux would broaden the spike and slow the return to baseline.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of identifying an agent that alters mitochondrial function, comprising:
    (a) contacting, in each of a plurality of reaction vessels in a high throughput screening array,
        (i) a biological sample comprising a cell containing cytosol, a mitochondrion and a calcium indicator molecule, under conditions that permit maintenance of mitochondrial membrane potential, with
        (ii) a source of calcium cations,
        wherein the calcium indicator molecule is capable of generating a detectable signal that is proportional to the level of calcium in the cytosol;
    (b) detecting in each reaction vessel the signal generated by the calcium indicator molecule at a plurality of time points, under conditions that permit identification of (i) mitochondrial calcium uniporter activity, wherein a decrease over time in the signal that is proportional to the level of calcium in the cytosol indicates mitochondrial calcium uniporter activity, and (ii) mitochondrial uncoupler or respiratory inhibitor activity, wherein an increase over time in the signal that is proportional to the level of calcium in the cytosol without repeating step (a) indicates mitochondrial uncoupler or respiratory activity; and
    (c) comparing the signal generated by the calcium indicator molecule at one or more of said time points in the absence of a candidate agent, to the signal generated by the calcium indicator molecule at one or more of said time points in the presence of the candidate agent, and therefrom identifying an agent that alters mitochondrial function.

2. The method of claim 1 wherein the step of contacting is repeated at least once.

3. The method of claim 1 wherein the sample contains at least one compound that alters intracellular distribution of a calcium cation.

4. The method of claim 3 wherein the compound that alters intracellular calcium cation distribution is selected from the group consisting of thapsigargin and Ru360.

5. The method of claim 3 wherein the compound that alters intracellular calcium cation distribution is selected from the group consisting of a calcium ionophore and a membrane permeable compound that alters intracellular calcium distribution.

6. The method of claim 3 wherein the sample contains at least one compound that uncouples oxidative phosphorylation from ATP production.

7. The method of claim 1 wherein the candidate agent is membrane permeable.

8. The method of claim 1 wherein the calcium indicator molecule is membrane permeable.

9. The method of claim 1 wherein the source of calcium cations is exogenous to the cell.

10. The method of claim 1 wherein the sample contains at least one compound that uncouples oxidative phosphorylation from ATP production.

11. The method of claim 1 wherein the cell comprises at least one polypeptide that is a Bcl-2 family member.

12. The method of claim 1 wherein the cell expresses a gene encoding a polypeptide that regulates cytosolic calcium.

13. The method of claim 12 wherein the gene encodes a mitochondrial calcium uniporter.

14. The method of claim 12 wherein the gene is a transfected gene.

15. The method of claim 14 wherein the gene encodes a mitochondrial calcium uniporter.

16. The method of claim 1 wherein the cell is a permeabilized cell.

17. The method of claim 1 wherein the cell adheres to a solid substrate.

18. The method of claim 1 wherein the cell is a non-adherent cell.

19. A method of identifying an agent that uncouples oxidative phosphorylation from ATP production, comprising:
   (a) contacting, in each of a plurality of reaction vessels in a high throughput screening array,
      (i) a biological sample comprising a cell containing cytosol, a mitochondrion and a calcium indicator molecule, under conditions that permit maintenance of mitochondrial membrane potential, with
      (ii) a source of calcium cations,
      wherein the calcium indicator molecule is capable of generating a detectable signal that is proportional to the level of calcium in the cytosol;
   (b) detecting in each reaction vessel the signal generated by the calcium indicator molecule at a plurality of time points, under conditions that permit identification of (i) mitochondrial calcium uniporter activity, wherein a decrease over time in the signal that is proportional to the level of calcium in the cytosol indicates mitochondrial calcium uniporter activity, and (ii) mitochondrial uncoupler or respiratory inhibitor activity, wherein an increase over time in the signal that is proportional to the level of calcium in the cytosol without repeating step (a) indicates mitochondrial uncoupler or respiratory activity;
   (c) repeating steps (a) and (b) at least once; and
   (d) comparing (i) the signal generated by the calcium indicator molecule at one or more of said time points prior to and following at least one of the contacting steps in the absence of the candidate agent, to (ii) the signal generated by the calcium indicator molecule at one or more of said time points prior to and following at least one of the contacting steps in the presence of the candidate agent, wherein an increased level of calcium in the cytosol at a time point prior to a contacting step in the presence of the agent, compared to the level of calcium in the cytosol prior to a contacting step in the absence of the agent, indicates an agent that uncouples oxidative phosphorylation from ATP production.

20. A method of identifying an agent that that is a respiratory inhibitor, comprising:
   (a) contacting, in each of a plurality of reaction vessels in a high throughput screening array,
      (i) a biological sample comprising a cell containing cytosol, a mitochondrion and a calcium indicator molecule, under conditions that permit maintenance of mitochondrial membrane potential, with
      (ii) a source of calcium cations,
      wherein the calcium indicator molecule is capable of generating a detectable signal that is proportional to the level of calcium in the cytosol;
   (b) detecting in each reaction vessel the signal generated by the calcium indicator molecule at a plurality of time points, under conditions that permit identification of (i) mitochondrial calcium uniporter activity, wherein a decrease over time in the signal that is proportional to the level of calcium in the cytosol indicates mitochondrial calcium uniporter activity, and (ii) mitochondrial uncoupler or respiratory inhibitor activity, wherein an increase over time in the signal that is proportional to the level of calcium in the cytosol without repeating step (a) indicates mitochondrial uncoupler or respiratory activity;
   (c) repeating steps (a) and (b) at least once; and
   (d) comparing (i) the signal generated by the calcium indicator molecule at one or more of said time points prior to and following at least one of the contacting steps in the absence of the candidate agent, to (ii) the signal generated by the calcium indicator molecule at one or more of said time points prior to and following at least one of the contacting steps in the presence of the candidate agent, wherein an increased level of calcium in the cytosol at a time point prior to a contacting step in the presence of the agent, compared to the level of calcium in the cytosol prior to a contacting step in the absence of the agent, indicates an agent that is a respiratory inhibitor.

21. A method of identifying an agent that alters a mitochondrial calcium uniporter, comprising:
   (a) contacting, in each of a plurality of reaction vessels in a high throughput screening array,
      (i) a biological sample comprising a cell containing cytosol, a mitochondrion and a calcium indicator molecule, under conditions that permit maintenance of mitochondrial membrane potential, with
      (ii) a source of calcium cations,
      wherein the calcium indicator molecule is capable of generating a detectable signal that is proportional to the level of calcium in the cytosol;
   (b) detecting in each reaction vessel the signal generated by the calcium indicator molecule at a plurality of time points, under conditions that permit identification of (i) mitochondrial calcium uniporter activity, wherein a decrease over time in the signal that is proportional to the level of calcium in the cytosol indicates mitochondrial calcium uniporter activity, and (ii) mitochondrial uncoupler or respiratory inhibitor activity, wherein an increase over time in the signal that is proportional to the level of calcium in the cytosol without repeating step (a) indicates mitochondrial uncoupler or respiratory activity;
   (c) repeating steps (a) and (b) at least once; and
   (d) comparing (i) the signal generated by the calcium indicator molecule at one or more of said time points prior to and following at least one of the contacting steps in the absence of the candidate agent, to (ii) the signal generated by the calcium indicator molecule at one or more of said time points prior to and following at least one of the contacting steps in the presence of the candidate agent, wherein an increased level of calcium in the cytosol at a time point following a contacting step in the presence of the agent, compared to the level of calcium in the cytosol following a contacting step in the absence of the agent, indicates that the agent alters a mitochondrial calcium uniporter.

22. A method of identifying an agent that alters mitochondrial function, comprising:
(a) contacting, in each of a plurality of reaction vessels in a high throughput screening array,
   (i) a biological sample comprising a cell containing a mitochondrion, cytosol and a calcium indicator molecule, under conditions that permit maintenance of mitochondrial membrane potential, and wherein the calcium indicator molecule is membrane permeable and capable of generating a detectable signal that is proportional to the level of calcium in the cytosol, with
   (ii) a calcium ionophore, under conditions and for a time sufficient to increase calcium levels within the cell;
(b) detecting in each reaction vessel the signal generated by the calcium indicator molecule at a plurality of time points, under conditions that permit identification of (i) mitochondrial calcium uniporter activity, wherein a decrease over time in the signal that is proportional to the level of calcium in the cytosol indicates mitochondrial calcium uniporter activity, and (ii) mitochondrial uncoupler or respiratory inhibitor activity, wherein an increase over time in the signal that is proportional to the level of calcium in the cytosol without repeating step (a) indicates mitochondrial uncoupler or respiratory activity; and
(c) comparing the signal generated by the calcium indicator molecule at one or more of said time points in the absence of the candidate agent, to the signal generated by the calcium indicator molecule at one or more of said time points in the presence of the candidate agent, and therefrom identifying an agent that alters mitochondrial function.

23. The method of claim 22 wherein the calcium ionophore is selected from the group consisting of ionomycin, A23187, NMDA and a cell depolarization signal.

24. The method of claim 22 wherein the step of contacting is repeated at least once.

25. The method of claim 22 wherein the sample contains at least one compound that alters intracellular distribution of a calcium cation.

26. The method of claim 25 wherein the compound that alters intracellular calcium cation distribution is selected from the group consisting of thapsigargin and Ru360.

27. The method of claim 25 wherein the compound that alters intracellular calcium cation distribution is selected from the group consisting of a calcium ionophore and a membrane permeable compound that alters intracellular calcium distribution.

28. The method of claim 25 wherein the sample contains at least one compound that uncouples oxidative phosphorylation from ATP production.

29. The method of claim 22 wherein the candidate agent is membrane permeable.

30. The method of claim 22 wherein the source of calcium cations is exogenous to the cell.

31. The method of claim 22 wherein the sample contains at least one compound that uncouples oxidative phosphorylation from ATP production.

32. The method of claim 22 wherein the cell comprises at least one polypeptide that is a Bcl-2 family member.

33. The method of claim 22 wherein the cell expresses a gene encoding a polypeptide that regulates cytosolic calcium.

34. The method of claim 33 wherein the gene encodes a mitochondrial calcium uniporter.

35. The method of claim 33 wherein the gene is a transfected gene.

36. The method of claim 35 wherein the gene encodes a mitochondrial calcium uniporter.

37. The method of claim 22 wherein the cell adheres to a solid substrate.

38. The method of claim 22 wherein the cell is a non-adherent cell.

39. A method of identifying an agent that alters mitochondrial function, comprising:
(a) contacting, in each of a plurality of reaction vessels in a high throughput screening array,
   (i) a biological sample comprising a permeabilized cell depleted of cytosol, a mitochondrion and a calcium indicator molecule, under conditions that permit maintenance of mitochondrial membrane potential, with
   (ii) a source of calcium cations,
   wherein the calcium indicator molecule is capable of generating a detectable signal that is proportional to the level of calcium in the cell;
(b) detecting in each reaction vessel the signal generated by the calcium indicator molecule at a plurality of time points, under conditions that permit identification of (i) mitochondrial calcium uniporter activity, wherein a decrease over time in the signal that is proportional to the level of calcium in the cytosol indicates mitochondrial calcium uniporter activity, and (ii) mitochondrial uncoupler or respiratory inhibitor activity, wherein an increase over time in the signal that is proportional to the level of calcium in the cytosol without repeating step (a) indicates mitochondrial uncoupler or respiratory activity; and
(c) comparing the signal generated by the calcium indicator molecule at one or more of said time points in the absence of a candidate agent, to the signal generated by the calcium indicator molecule at one or more of said time points in the presence of the candidate agent, and therefrom identifying an agent that alters mitochondrial function.

40. The method of claim 39 wherein the calcium indicator molecule is capable of generating a detectable signal that is proportional to the level of calcium in the mitochondrion.

41. The method of claim 39 wherein the calcium indicator molecule is capable of generating a detectable signal that is proportional to the level of calcium outside of the mitochondrion.

42. The method of claim 39 wherein the step of contacting is repeated at least once.

43. The method of claim 39 wherein the sample contains at least one compound that alters intracellular distribution of a calcium cation.

44. The method of claim 43 wherein the compound that alters intracellular calcium cation distribution is selected from the group consisting of thapsigargin and Ru 360.

45. The method of claim 43 wherein the sample contains at least one compound that uncouples oxidative phosphorylation from ATP production.

46. The method of claim 39 wherein the source of calcium cations is exogenous to the cell.

47. The method of claim 39 wherein the sample contains at least one compound that uncouples oxidative phosphorylation from ATP production.

48. The method of claim 39 wherein the cell comprises at least one polypeptide that is a Bcl-2 family member.

49. The method of claim 39 wherein the cell expresses a gene coding a polypeptide that regulates cytosolic calcium.

50. The method of claim 49 wherein the gene encodes a mitochondrial calcium uniporter.

51. The method of claim 49 wherein the gene is a transfected gene.

52. The method of claim 51 wherein the gene encodes a mitochondrial calcium uniporter.

53. The method of claim 39 wherein the cell adheres to a solid substrate.

54. The method of claim 39 wherein the cell is a non-adherent cell.

55. A method of identifying an agent that alters mitochondrial function, comprising:
  (a) contacting, in each of a plurality of reaction vessels in a high throughput screening array,
    (i) a biological sample comprising one or more isolated mitochondria and a calcium indicator molecule in a medium, under conditions that permit maintenance of mitochondrial membrane potential, with
    (ii) a source of calcium cations,
    wherein the calcium indicator molecule is capable of generating a detectable signal that is proportional to the level of calcium in the biological sample;
  (b) detecting in each reaction vessel the signal generated by the calcium indicator molecule at a plurality of time points, under conditions that permit identification of (i) mitochondrial calcium uniporter activity, wherein a decrease over time in the signal that is proportional to the level of calcium in the cytosol indicates mitochondrial calcium uniporter activity, and (ii) mitochondrial uncoupler or respiratory inhibitor activity, wherein an increase over time in the signal that is proportional to the level of calcium in the cytosol without repeating step (a) indicates mitochondrial uncoupler or respiratory activity; and
  (c) comparing the signal generated by the calcium indicator molecule at one or more of said time points in the absence of a candidate agent, to the signal generated by the calcium indicator molecule at one or more of said time points in the presence of the candidate agent, and therefrom identifying an agent that alters mitochondrial function.

56. A method of identifying an agent that alters mitochondrial function, comprising:
  (a) contacting
    (i) a biological sample comprising one or more isolated mitochondria and a calcium indicator molecule in a medium, under conditions that permit maintenance of mitochondrial membrane potential, with
    (ii) a source of calcium cations,
    wherein the calcium indicator molecule is capable of generating a detectable signal that is proportional to the level of calcium in the biological sample;
  (b) detecting the signal generated by the calcium indicator molecule at a plurality of time points, under conditions that permit identification of (i) mitochondrial calcium uniporter activity, wherein a decrease over time in the signal that is proportional to the level of calcium in the cytosol indicates mitochondrial calcium uniporter activity, and (ii) mitochondrial uncoupler or respiratory inhibitor activity, wherein an increase over time in the signal that is proportional to the level of calcium in the cytosol without repeating step (a) indicates mitochondrial uncoupler or respiratory activity; and
  (c) comparing the signal generated by the calcium indicator molecule at one or more of said time points in the absence of a candidate agent, to the signal generated by the calcium indicator molecule at one or more of said time points in the presence of the candidate agent, and therefrom identifying an agent that alters mitochondrial function.

57. The method of either claim 55 or claim 56 wherein the calcium indicator molecule is capable of generating a detectable signal that is proportional to the level of calcium in the mitochondrion.

58. The method of either claim 55 or claim 56 wherein the calcium indicator molecule is capable of generating a detectable signal that is proportional to the level of calcium outside of the mitochondrion.

59. The method of either claim 55 or claim 56 wherein the step of contacting is repeated at least once.

60. The method of either claim 55 or claim 56 wherein the sample contains at least one compound that alters distribution of a calcium cation in the sample.

61. The method of claim 60 wherein the compound that alters calcium cation distribution is selected from the group consisting of thapsigargin and Ru360.

62. The method of claim 60 wherein the sample contains at least one compound that uncouples oxidative phosphorylation from ATP production.

63. The method of either claim 55 or claim 56 wherein the isolated mitochondria are derived from a cell that comprises at least one polypeptide that is a Bcl-2 family member.

64. The method of either claim 55 or claim 56 wherein the isolated mitochondria are derived from a cell that expresses a gene encoding a polypeptide that regulates cytosolic calcium.

65. The method of claim 64 wherein the gene encodes a mitochondrial calcium uniporter.

66. The method of claim 64 wherein the gene is a transfected gene.

67. The method of claim 66 wherein the gene encodes a mitochondrial calcium uniporter.

68. The method of any one of claims 1, 21, 39, 55 or 56 wherein subsequent to the step of contacting the biological sample with the source of calcium cations and prior to the step of comparing signals, the biological sample is contacted (i) with at least one compound that uncouples oxidative phosphorylation from ATP production, and (ii) with at least on agent that alters mitochondrial function.

69. The method of claim 68 wherein the agent that alters mitochondrial function is cyclosporin A.

70. The method of claim 68 wherein the agent that alters mitochondrial function is selected from the group consisting of cyclosporin A, rotenone, oligomycin, succinate and Bcl-2.

71. The method of claim 68 wherein the compound that uncouples oxidative phosphorylation from ATP production is selected from the group consisting of FCCP and CCCP.

* * * * *